(12) United States Patent
Myung et al.

(10) Patent No.: US 12,102,667 B2
(45) Date of Patent: Oct. 1, 2024

(54) POLYPEPTIDES AND ANTIBIOTICS AGAINST GRAM-NEGATIVE BACTERIUM COMPRISING THE SAME

(71) Applicants: LyseNTech Co., Ltd., Seongnam-si (KR); Hankuk University OF Foreign Studies Research & Business Foundation, Yongin-si (KR)

(72) Inventors: Heejoon Myung, Yongin-si (KR); Min Soo Kim, Seongnam-si (KR); Hye-Won Hong, Seongnam-si (KR); Young Deuk Kim, Seongnam-si (KR); Jaeyeon Jang, Seongnam-si (KR)

(73) Assignees: LYSENTECH CO., LTD., Seongnam-si (KR); HANKUK UNIVERSITY OF FOREIGN STUDIES RESEARCH & BUSINESS FOUNDATION, Yongin-si (KR)

( * ) Notice: Subject to any disclaimer, the term of this patent is extended or adjusted under 35 U.S.C. 154(b) by 0 days.

(21) Appl. No.: 17/820,316

(22) Filed: Aug. 17, 2022

(65) Prior Publication Data
US 2022/0387563 A1 Dec. 8, 2022

(30) Foreign Application Priority Data

Aug. 19, 2021 (KR) .................. 10-2021-0109266
Jan. 27, 2022 (KR) .................. 10-2022-0012566
Jun. 9, 2022 (KR) .................. 10-2022-0070371

(51) Int. Cl.
| A61K 38/47 | (2006.01) |
| A61K 38/12 | (2006.01) |
| A61P 31/04 | (2006.01) |
| C12N 7/00 | (2006.01) |
| C12N 9/36 | (2006.01) |

(52) U.S. Cl.
CPC ............. *A61K 38/47* (2013.01); *A61K 38/12* (2013.01); *A61P 31/04* (2018.01); *C12N 7/00* (2013.01); *C12N 9/2462* (2013.01); *C12Y 302/01017* (2013.01); *C12N 2795/00042* (2013.01)

(58) Field of Classification Search
None
See application file for complete search history.

(56) References Cited

FOREIGN PATENT DOCUMENTS

| CN | 108486089 | 9/2018 |
| CN | 110651044 | 1/2020 |
| CN | 111254121 | 6/2020 |
| CN | 111269893 | 6/2020 |
| KR | 10-2014-0093403 | 7/2014 |
| KR | 10-2019-0085549 | 7/2019 |
| KR | 10-2021-0014673 | 2/2021 |
| KR | 10-2224897 | 3/2021 |
| KR | 102286544 | 8/2021 |
| WO | 2017-203471 | 11/2017 |
| WO | 2018-185634 | 10/2018 |
| WO | 2019-039826 | 2/2019 |
| WO | WO 2019/229184 | * 5/2019 |
| WO | 2019-212244 | 11/2019 |

OTHER PUBLICATIONS

Lee et al., "Structure-activity relationships of cecropin-like peptides and their interactions with phospholipid membrane", BMB Reports 2013; 46(5): 282-287.*
KIPO, PCT Search Report & Written Opinion of PCT/KR2022/012373 dated Nov. 23, 2022.
EPO, Search Report of EP 22191276.9 dated Jan. 10, 2023.
Karlin, Samuel, et al. "Applications and statistics for multiple high-scoring segments in molecular sequences." Proceedings of the National Academy of Sciences 90.12 (1993): 5873-5877, Jun. 1993.
Pearson, William R. "[5] Rapid and sensitive sequence comparison with FASTP and FASTA." Methods in Enzymology, vol. 183 (1990): 63-98, Academic Press.
Luepke, Katherine H., et al. "Past, present, and future of antibacterial economics: increasing bacterial resistance, limited antibiotic pipeline, and societal implications." Pharmacotherapy, 37.1 (2017): 71-84, retrieved from https://doi. org/10.1002/phar.1868.
Rahmouni, Oumaïra, et al. "High carriage of adherent invasive E. coli in wildlife and healthy individuals." Gut pathogens 10.1 (2018): 1-11, Jun. 14, 2018.
Schmelcher, Mathias, et al. "Bacteriophage endolysins as novel antimicrobials." Future microbiology 7.10 (2012): 1147-1171.
Tacconelli, Evelina, et al. "Discovery, research, and development of new antibiotics: the WHO priority list of antibiotic-resistant bacteria and tuberculosis.", Dec. 21, 2017, Retrieved from http://dx.doi.org/10.1016/S1473-3099(17)30753-3.
Wang, Ing-Nang, et al. "Holins: the protein clocks of bacteriophage infections." Annual Reviews in Microbiology 54.1 (2000): 799-825.
CBI GenBank: No. QNO11629.1, endolysin [*Escherichia* phage vB_EcoS_fFiEco02], Sep. 8, 2020.

* cited by examiner

*Primary Examiner* — Suzanne M Noakes
(74) *Attorney, Agent, or Firm* — LEX IP MEISTER, PLLC

(57) ABSTRACT

Provided are a novel polypeptide having endolysin activity, a fusion protein comprising the polypeptide and an antibiotic active protein, and an antibiotic use against a gram-negative pathogen of the polypeptide and/or fusion protein and/or a use for prevention and/or treatment of gram-negative pathogen infection and/or disease or symptoms related to gram negative pathogen infection.

19 Claims, 19 Drawing Sheets
Specification includes a Sequence Listing.

FIG. 9

Sequence Listing
YP_009113200.1 (SEQ ID NO: 14)
QIG59335.1 (SEQ ID NO: 15)
YP_009168880.1 (SEQ ID NO: 16)
QBJ02951.1 (SEQ ID NO: 17)
QNO11629.1 (SEQ ID NO: 18)
EC340 (SEQ ID NO: 2)
HAM52077861 (SEQ ID NO: 19)
QNO11705.1 (SEQ ID NO: 20)
QNO11777.1 (SEQ ID NO: 21)

*E. coli* ATCC 8739

POLYPEPTIDES AND ANTIBIOTICS AGAINST GRAM-NEGATIVE BACTERIUM COMPRISING THE SAME

STATEMENT REGARDING GOVERNMENT SPONSORED RESEARCH

This invention was made with government support under Ref No: 1465034674 awarded by Korean Health Industry Development Institute, Ministry of Health and Welfare.

REFERENCE TO AN ELECTRONIC SEQUENCE LISTING

The contents of the electronic sequence listing (LPP20222632US SEQ.xml; Size: 77 K bytes; and Date of Creation: Nov. 8, 2023) is herein incorporated by reference in its entirety. The contents of the electronic sequence listing in no way introduces new matter into the specification.

TECHNICAL FIELD

The present disclosure provides a novel polypeptide having endolysin activity, a fusion protein comprising an endolysin peptide and an antibiotic active protein, and an antibiotic against a gram-negative pathogen of the polypeptide and/or fusion protein and/or a use as a pharmaceutical composition for prevention and/or treatment of gram-negative pathogen infection and/or disease or symptoms related to gram negative pathogen infection.

BACKGROUND ART

Bacteriophage refers to a bacterium-specific virus that infects a specific bacterium and inhibits and impedes growth of the infected bacterium. Bacteriophages have the ability to gram-negative kill bacterium in the manner of proliferating inside bacterial cells after infection with their host bacterium, and when progeny bacteriophages come out of the bacterium after proliferation, using endolysin, a protein of the bacteriophage, to destroy the cell wall of the host bacterium. Therefore, a substance having an endolysin activity of the bacteriophage can be usefully applied as an antibiotic candidate.

Recently, antibiotic-resistant bacterium are rapidly increasing, and multidrug-resistant bacterium that cannot be treated with any antibiotic are also increasing. In particular, *Pseudomonas aeruginosa*, one of gram-negative bacterium, is one of ESKAPE (*Enterococcus faecium, Staphylococcus aureus, Klebsiella pneumoniae, Acinetobacter baumannii, Pseudomonas aeruginosa*, and *Enterobacter* species) bacterium that urgently need development of a new treatment method worldwide, and *Escherichia coli* is a bacterium involved in various infections. Therefore, it is required to develop a treatment method that is differentiated from conventional antibiotics.

DISCLOSURE

Technical Problem

One aspect provides a mutant polypeptide, in which a mutation in which amino acids corresponding to at least one position selected from the group consisting of the 39th, 43rd, 45th, 73th, 81th, 101th, and 113th in the amino acid sequence of SEQ ID NO: 2 is substituted with amino acids different from the original is introduced.

Another aspect, provides a fusion polypeptide, comprising a polypeptide comprising the amino acid sequence of Cecropin A and SEQ ID NO: 2 or comprising the mutant polypeptide.

Other aspect, provides a polynucleotide encoding the mutant polypeptide or the fusion polypeptide.

Other aspect, provides a recombinant vector comprising the polynucleotide.

Other aspect, provides a recombinant cell comprising the polynucleotide or a recombinant vector comprising the same.

Other aspect, provides an antibiotic comprising one or more kinds selected from the group consisting of
- a polynucleotide encoding the mutant polypeptide or the fusion polypeptide,
- a recombinant vector comprising the polynucleotide, and
- a recombinant cell comprising the polynucleotide or recombinant vector.

Other aspect, provides a pharmaceutical composition for prevention or treatment of infection of gram-negative bacterium or disease caused by gram-negative bacterium, comprising at least one selected from the group consisting of
- a polynucleotide encoding the mutant polypeptide or the fusion polypeptide,
- a recombinant vector comprising the polynucleotide, and
- a recombinant cell comprising the polynucleotide or the recombinant vector.

Other aspect, provides a feed additive comprising the antibiotic.

Other aspect, provides a disinfectant comprising the antibiotic.

Other aspect, provides a detergen, comprising the antibiotic.

Technical Solution

Engineered endolysin having enhanced antibacterial activity against a gram-negative pathogen as well as a synergistic effect observed when used with a standard treatment antibiotic is provided.

One aspect provides a polypeptide of SEQ ID NO: 2 or 6. The polypeptide may act as endolysin for gram-negative bacterium, and may be useful as an antibiotic. When a polypeptide is synthesized by recombination, methionine (M) may be added as the first amino acid residue at the N-terminus of the amino acid sequence of SEQ ID NO: 2 or 6.

Another aspect provides a fusion polypeptide comprising a polypeptide of SEQ ID NO: 2 or 6 and an antibiotic protein, for example, Cecropin A (for example, SEQ ID NO: 8, or SEQ ID NO: 9). In the fusion polypeptide, the polypeptide and antibiotic protein may be fused each other directly (without a linker) or by a peptide linker. For example, the fusion polypeptide may comprise the amino acid sequence of SEQ ID NO: 10.

(EC340)

SEQ ID NO: 2

VSRNISNNGIKFTAAFEGFRGTAYRATPNEKYLTIGYGHYGPDVTPGKT

ITPGQGLLLLNRDMAKAVAAVDAAAHHSLTQAQFDAVCDLVYNAGAGVI

AATTGTGKALRSGDIATLRAKLALFINQNGKPLLGLRRRTAGRLALFDG

KPWQEAEAIGRAVKG

-continued (mtEC340)
SEQ ID NO: 6
VSRNISNNGIKFTAAFEGFRGTAYRATPNEKYLTIGYGSYGPHVEPGKT

ITPGQGLLLLNRDMAKAVAAVDAVAHHSLTQSQFDAVCDLVYNAGAGVI

AAATGTGKALRSGDVATLRAKLALFINQNGKPLLGLRRRTAGRLALFDG

KPWQEAEAIGRAVKG (LNT113; Cecropin A-GGGGSx3 linker-mtEC340)
SEQ ID NO: 10
MKWKLFKKIEKVGQNIRDGIIKAGPAVAVVGQATQIAKGGGGSGGGGSG

GGGSVSRNISNNGIKFTAAFEGFRGTAYRATPNEKYLTIGYGSYGPHVE

PGKTITPGQGLLLLNRDMAKAVAAVDAVAHHSLTQSQFDAVCDLVYNAG

AGVIAAATGTGKALRSGDVATLRAKLALFINQNGKPLLGLRRRTAGRLA

LFDGKPWQEAEAIGRAVKG (Cecropin A)
SEQ ID NO: 8
KWKLFKKIEKVGQNIRDGIIKAGPAVAVVGQATQIAK (Cecropin A, M is added to N-terminus of SEQ ID NO: 8)
SEQ ID NO: 9
MKWKLFKKIEKVGQNIRDGIIKAGPAVAVVGQATQIAK Other aspect provides a polynucleotide encoding the polypeptide or fusion polypeptide.

Other aspect provides a recombinant vector comprising the polynucleotide. The recombinant vector may be an expression vector.

Other aspect provides a recombinant cell comprising the polynucleotide or the recombinant vector. The recombinant cell may be used for expression of the polynucleotide.

Other aspect provides an antibiotic comprising at least one selected from the group consisting of the followings:
  the polypeptide, for example, SEQ ID NO: 2 or 6;
  the fusion polypeptide, for example, SEQ ID NO: 10;
  a polynucleotide encoding the polypeptide or the fusion polypeptide;
  a recombinant vector comprising the polynucleotide; and
  a recombinant cell comprising the polynucleotide or the recombinant vector.

The antibiotic may have an antibiotic effect against one or a plurality of (e.g.: 2, 3, 4, 5, 6, 7, 8, 9, 10, 11, 12, 13, 14, 15, 16, 17, 18, 19, or 20) gram-negative bacterium.

Other aspect provides a pharmaceutical composition for preventing and/or treating infection of gram-negative bacterium and/or symptoms or disease related to infection of gram-negative bacterium (caused thereby), and the pharmaceutical composition may comprise one or more kinds selected from the group consisting of the followings:
  the aforementioned polypeptide, for example, SEQ ID NO: 2 or 6;
  the aforementioned fusion polypeptide, for example, SEQ ID NO: 10;
  a polynucleotide encoding the polypeptide or the fusion polypeptide;
  a recombinant vector comprising the polynucleotide; and
  a recombinant cell comprising the polynucleotide or the recombinant vector.

The pharmaceutical composition may further comprise one or more of pharmaceutically acceptable carriers.

Other aspect provides a method for preventing and/or treating infection of gram-negative bacterium and/or symptoms or disease related to infection of gram-negative bacterium (caused thereby), comprising administering a pharmaceutical composition comprising one or more kinds selected from the group consisting of the followings orally or parenterally (for example, intravenously, subcutaneously, intraperitoneally or intramuscularly, or the like):
  the aforementioned polypeptide, for example, SEQ ID NO: 2 or 6;
  the aforementioned fusion polypeptide, for example, SEQ ID NO: 10;
  a polynucleotide encoding the polypeptide or the fusion polypeptide;
  a recombinant vector comprising the polynucleotide; and
  a recombinant cell comprising the polynucleotide or the recombinant vector.

Hereinafter, the present invention will be described in more detail.

When a bacteriophage that can be used as a natural antibiotic by proliferating bacterium into a host penetrates the bacterium and finishes proliferation inside, the completed phage particles are released to the outside of the bacterium, and then, an enzyme that creates a pathway for release to the outside by attacking and decomposing the cell wall of the bacterium is endolysin. All bacteriophages have this endolysin gene in their genome and use endolysin protein expressed during proliferation. The bacteriophage that proliferates using bacterium as a host and endolysin derived from the bacteriophage having the property of decomposing the cell wall can be used as natural antibiotics. In the present description, a novel bacteriophage is isolated, and an antibiotic effect of the bacteriophage and endolysin derived therefrom is determined, thereby providing an antibiotic of the bacteriophage and endolysin derived therefrom and/or a use related thereto.

In case of gram-positive bacterium, since the cell wall is located on the outermost wall, when endolysin is added from the outside, the cell wall is immediately attacked and decomposed. On the other hand, in case of gram-negative bacterium, the outer cell membrane exists at the outermost part, and the cell wall is located inside it, and therefore, even if endolysin is added from the outside, it must first pass through the outer cell membrane to meet the cell wall. Therefore, it has been known that basically endolysin has no effect on gram-negative bacterium. The polypeptide having endolysin activity provided in the present description is characterized by having an effect of killing gram-negative bacterium.

Bacteriophage lysine, also called endolysin or murein hydrolase, is a hydrolytic enzyme produced by a bacteriophage at the last stage of the lysis cycle and can cleave through the host cell wall, so that the phage proliferates inside and then bursts in the host bacterium. When applied as a recombinant protein to gram-negative bacterium from the outside, lysin cannot easily reach the cell wall due to presence of the outer membrane. In the present application, endolysin EC340 obtained from phage PBEC131 infecting *E. coli* was engineered to improve outer membrane permeability and increase activity against gram-negative bacterium. The engineered endolysin, LNT113, was tested for a potential synergistic effect with a standard-of-care antibiotic. An additive effect was observed with meropenem, tigecycline, chloramphenicol, azithromycin and ciprofloxacin, whereas a synergistic effect was demonstrated with colistin. Neither ceftazidime and kanamycin showed a synergistic or additive effect with LNT113 endolysin. Moreover, the synergistic effect and additive effect could not be generalized by antibiotic type, outer membrane transmembrane, molecular weight or bactericidal properties of each antibiotic tested.

Cecropin A, isolated from hemolymph of *Hyalophora cecropia*, is a 37 amino acid peptide with an amphipathic alpha-helix structure and exhibits antibacterial activity by interacting with the outer membrane of gram-negative bacterium. In the present application, fusion of cecropin A and mtEC340 increased cell membrane permeability by 1.8 times and increased antimicrobial activity by 2-4 log. Cecropin A has been reported to induce membrane disruption, but a generally agreed action mode has not yet been elucidated. It is proposed that cecropin A causes distortion across the outer membrane by self-promoted absorption. As demonstrated in the present application, the distortion of the outer membrane can promote the absorption of cecropin-fused endolysin and cecropin itself, thereby further improving the antibacterial efficacy of the fusion protein.

Since the 1990s, colistin has been used as a last resort against the rapid increase in multidrug-resistant pathogens. LNT113 was confirmed to have a synergistic effect with colistin in a checkerboard assay. Colistin directly interacts with lipid A of lipopolysaccharide (PLS), and plays an important role in antimicrobial activity by forming LPS-colistin clusters in the synthetic LPS/phospholipid bilayer. Mutation in genes involved in lipid A biosynthesis produces LPS-deficient bacterium, leading to colistin resistance. Another resistance mechanism adds phosphoethanolamine to lipid A and interferes with adhesion of colistin, in relation to MCR-1, a member of the phosphoethanolamine transferase enzyme family. This interaction of colistin and lipid A may enable more efficient absorption of endolysin, resulting in higher antimicrobial efficacy of the fusion protein. No synergistic effect was observed between LNT113 and antibiotics other than colistin. The additional effect is also showed differently depending on the target strain, consistent with the previous report. This difference was independent of antibiotic susceptibility. MDR strain CCARM 1A746 (Table 1) showed a higher FICI value due to presence of multiple resistance mechanisms that inhibit the antibacterial effect of LNT113 in several ways. It was not possible to generalize the combined effect of different types of antibiotics. For example, ceftazidime, one of the two beta-lactam antibiotics tested, showed little additive effect with LNT113, while the other beta-lactam antibiotic, meropenem, had a slight additive effect. According to the outer membrane transmembrane mechanism, macrolide such as azithromycin and aminoglycoside such as kanamycin use a lipid-mediated pathway, whereas beta-lactam uses porin-mediated diffusion. In other words, no consistent pattern was observed between groups in the present application. In addition, the molecular weight of each antibiotic tested or bacteriostatic or bactericidal action mechanism did not show a consistent pattern.

In summary, in the present application, the engineered endolysin LNT113 was produced and the antibacterial efficacy was confirmed in vitro. Since this endolysin has a synergistic effect with colistin and some additional effects with standard-of-care antibiotics, it could be used in a new way to overcome the current problem of antibiotic resistance.

Definition of Terms

In the present description, that a polynucleotide (can be interchangeably used with "gene") or a polypeptide (can be interchangeably used with "protein") "comprises a specific nucleic acid sequence or amino acid sequence" or "consists of a specific nucleic acid sequence or amino acid sequence" may mean that the polynucleotide or polypeptide essentially comprises the specific nucleic acid sequence or amino acid sequence, and may be interpreted as comprising "a substantially equivalent sequence" in which a mutation (deletion, substitution, modification and/or addition) is added to the specific nucleic acid sequence or amino acid sequence within the range of maintaining the original function and/or desired function of the polynucleotide or polypeptide (or not excluding the mutation).

In one embodiment, that a polynucleotide or polypeptide "comprises a specific nucleic acid sequence or amino acid sequence" or "consists of or is expressed as a specific nucleic acid sequence or amino acid sequence" may mean that the polynucleotide or polypeptide (i) essentially comprises the specific nucleic acid sequence or amino acid sequence, or (ii) consists of an amino acid sequence having homology (identity) of 96% or more, 96.3% or more, 97% or more, 97.7% or more, 98% or more, 98.5% or more, 99% or more, 99.2% or more, 99.5% or more, or 99.9% or more to the specific nucleic acid sequence or amino acid sequence or essentially comprises thereof, and maintains the original function and/or desired function. In the present description, the original function may be endolysin enzymatic function (for example, peptidoglycan hydrolytic activity), cecropin A activity (for example, cell membrane lytic activity) and/or antibiotic action, (in case of amino acid sequence), or function of encoding protein having endolysin enzymatic function, cecropin A activity and/or antibiotic action (in case of nucleic acid sequence), and the desired function may mean the antibiotic activity against gram-negative bacterium.

In the present invention, the term "homology (identity)" refers to a degree of correspondence with a given nucleic acid or amino acid sequence and can be expressed as a percentage (%). In case of homology for a nucleic acid sequence, for example, it may be determined using algorithm BLAST by a document (See: Karlin and Altschul, Pro. Natl. Acad. Sci. USA, 90, 5873, 1993) or FASTA by Pearson (See: Methods Enzymol., 183, 63, 1990). Based on this algorithm BLAST, programs called BLASTN or BLASTX have been developed.

The protein or polypeptide provided in the present description may be isolated and/or purified from nature, or synthesized recombinantly or chemically. When the amino acid sequence of the protein or polypeptide provided in the present description comprises a methionine (Met, M) or Met-Ala-Ser (MAS) sequence as the first amino acid residue, the protein or polypeptide may be recombinantly produced, and the methionine at the first amino acid position from the N-terminus may be encoded by an initiation codon. Accordingly, when the amino acid sequence of the protein or polypeptide provided in the present description comprises methionine by recombinant production at the N-terminus, in case that the protein or polypeptide is obtained by other methods (for example, chemical synthesis or isolation from nature), it can be interpreted as comprising an amino acid sequence starting from the second amino acid residue excluding methionine at the first position of the N-terminus by recombinant production or an amino acid sequence starting from an amino acid residue following the MAS sequence (for example, the 4th amino acid residue).

The endolysin refers to peptidoglycan hydrolase encoded by a bacteriophage. Endolysin is synthesized during late gene expression in the lytic cycle of bacteriophage proliferation and mediates the release of progeny virions from infected cells through degradation of bacterial peptidoglycan. In terms of enzymatic activity, endolysin may have at least one activity selected from the group consisting of glucosaminidase, muramidase (one kind of lysozyme), transglycosylase, amidase, endopeptidase and the like.

In the present description, that a polynucleotide (can be interchangeably used with "gene") or polypeptide (can be interchangeably used with "protein") "comprises a specific nucleic acid sequence or amino acid sequence" or "consists of a specific nucleic acid sequence or amino acid sequence" may mean that the polynucleotide or polypeptide consists of the specific nucleic acid sequence or amino acid sequence or essentially comprises thereof, and may be interpreted as comprising "a substantially equivalent sequence" in which a mutation (deletion, substitution, modification and/or addition) is added to the specific nucleic acid sequence or amino acid sequence within the range of maintaining the original function an/or desired function of the polynucleotide or polypeptide.

In the present description, the original function may be endolysin enzymatic function (for example, peptidoglycan hydrolysis activity) (in case of amino acid sequence), or function of encoding protein having endolysin enzymatic function (in case of nucleic acid sequence), and the desired function may mean antibiotic activity against *Pseudomonas* sp. bacterium, for example, *Pseudomonas aeruginosa*.

The polypeptide provided in the present description may be not derived from nature, and may be recombinantly or chemically synthesized. When the polypeptide is recombinantly produced, it may be in a form in which a common signal peptide, cleavage site, tag, or the like is combined for purification. Therefore, in one non-limitative embodiment, the polypeptide provided in the present description, the polypeptide provided in the present description may be in a form in which one or more selected from the group consisting of a signal peptide, cleavage site, tag (for example, His tag, GST (glutathione-s-transferase) tag, MBP (maltose binding protein) tag, etc.), or the like commonly available in the recombinant production process of protein, or in a form in which they are removed.

Bacteriophage

One embodiment provides a novel bacteriophage.

The bacteriophage may comprise a polynucleotide comprising the nucleic acid sequence of SEQ ID NO: 1 or consisting of the sequence, or, a polynucleotide comprising the nucleic acid sequence having homology or identity of 96.5% or more, 97% or more, 97.5% or more, 98% or more, 98.5% or more, 99% or more, 99.5% or more, or 99.9% or more to the nucleic acid sequence of SEQ ID NO: 1, or consisting of the sequence.

The bacteriophage may comprise one or more kinds selected from the group consisting of a wild-type polypeptide, a polynucleotide encoding the wild-type polypeptide, a mutant polypeptide, a polynucleotide encoding the mutant polypeptide, a fusion polypeptide, and a polynucleotide encoding the fusion polypeptide, which will be described below.

Hereinafter, the polypeptide and polynucleotide will be described in detail.

Wild-Type Polypeptide and Polynucleotide Encoding the Same

One embodiment provides a novel polypeptide. The polypeptide may comprise the amino acid sequence of SEQ ID NO: 2.

The polypeptide may be derived from a bacteriophage. The polypeptide may have endolysin activity derived from the bacteriophage. The polypeptide may have a molecular weight of about 19 kDa (19 kDa±2). In one embodiment, the polypeptide may be derived from a bacteriophage comprising the nucleic acid sequence of SEQ ID NO: 1. The polypeptide may have antibiotic activity against gram-negative bacterium.

Other embodiment provides a polynucleotide encoding the polypeptide. The polynucleotide may comprise the nucleic acid sequence of SEQ ID NO: 3.

In the present description, unless otherwise described, the polypeptide having endolysin activity as a polypeptide comprising the amino acid sequence of SEQ ID NO: 2 may mean (1) a polypeptide consisting of the amino acid sequence of SEQ ID NO: 2 or essentially comprising thereof, and/or (2) a polypeptide consisting of the amino acid having homology of 98.8% or more, 99% or more, 99.2% or more, 99.4% or more, 99.6% or more, or 99.9% or more to the amino acid sequence of SEQ ID NO: 2 or essentially comprising thereof, which has (maintains) endolysin enzyme function (for example, peptidoglycan hydrolysis activity) and/or antibiotic activity against *Pseudomonas* sp. bacterium, for example, *Pseudomonas aeruginosa*.

In addition, in the present description, unless otherwise described, a polynucleotide encoding a polypeptide comprising the amino acid sequence of SEQ ID NO: 2 or consisting of the amino acid sequence of SEQ ID NO: 2, may mean (a) a polynucleotide encoding a polypeptide consisting of the amino acid sequence of SEQ ID NO: 2 or essentially comprising the same, and/or (b) a polynucleotide consisting of the amino acid sequence having homology of 98.8% or more, 99% or more, 99.2% or more, 99.4% or more, 99.6% or more, or 99.9% or more to the amino acid sequence of SEQ ID NO: 2, which has (maintains) endolysin enzyme function (for example, peptidoglycan hydrolysis activity) and/or antibiotic activity against *Pseudomonas* sp. bacterium, for example, *Pseudomonas aeruginosa*, and/or (c) a polynucleotide comprising the nucleic acid sequence of SEQ ID NO: 3, and the polynucleotide comprising the nucleic acid sequence of SEQ ID NO: 3 may mean (d) a polynucleotide consisting of the nucleic acid sequence of SEQ ID NO: 3 or essentially comprising the same.

Mutant Polypeptide and Polynucleotide Encoding Thereof

One embodiment provides a novel mutant polypeptide. The mutant polypeptide may be a mutant polypeptide in which a mutation is introduced to a polypeptide of the amino acid sequence of SEQ ID NO: 2. The polypeptide may be derived from a bacteriophage. The polypeptide may have endolysin activity derived from a bacteriophage. The polypeptide may have antibiotic activity against gram-negative bacterium.

The mutant polypeptide may be a mutant polypeptide in which at least one amino acid residues is substituted, deleted or inserted to a polypeptide comprising the amino acid sequence of SEQ ID NO: 2. The polypeptide may be prepared recombinantly or synthetically (for example, chemical synthesis).

The polypeptide to be a subject of mutation introduction of the present application may consist of the amino acid sequence of SEQ ID NO: 2 or comprise the amino acid sequence of SEQ ID NO: 2, and have endolysin activity, but not limited thereto. In other words, it does not exclude meaningless sequence addition before or after the amino acid sequence of SEQ ID NO: 2 or mutation that may occur naturally, or silent mutation thereof, and when having the same or corresponding activity to protein comprising the amino acid sequence of SEQ ID NO: 2, it may correspond to the protein to be a subject for mutation introduction of the present application. For example, the protein to be a subject for mutation introduction of the present application may be a protein composed of the amino acid sequence of SEQ ID NO: 2 or an amino acid sequence having homology or identity of 98.8% or more, 99% or more, 99.2% or more, 99.4% or more, 99.6% or more, or 99.9% or more thereto. In addition, as long as it is an amino acid sequence having this homology or identity and showing efficacy corresponding to the protein, a protein having an amino acid sequence in which some sequences are deleted, modified, substituted or added may be comprised within the range of the protein to be a subject of the present application.

In another embodiment, the polypeptide may be a mutant polypeptide in which an amino acid corresponding to at least one (for example, 2 or more, 3 or more, 4 or more, 5 or more, 6 or more, or all of 7) positions selected from the group consisting of the 39th, 43th, 45th, 73th, 81th, 101th, and 113th from the N-terminus of the amino acid sequence of SEQ ID NO: 2 is substituted to another amino acid different from the original amino acid to the amino acid sequence of SEQ ID NO: 2.

Specifically, the polypeptide may be a mutant polypeptide in which at least one (for example, 2 or more, 3 or more, 4 or more, 5 or more, 6 or more, or all of 7) of mutations selected from the following 1) to 7) is introduced to the amino acid sequence of SEQ ID NO: 2:

1) a substitution of the amino acid corresponding to the 39th residue from the N-terminus in the amino acid sequence of SEQ ID NO: 2 with other amino acid, that is, serine, arginine, lysine, aspartic acid, glutamic acid, threonine, asparagine, glutamine, cysteine, glycine, proline, alanine, valine, isoleucine, leucine, methionine, phenylalanine, tyrosine, or tryptophan;
2) a substitution of the amino acid corresponding to the 43th residue from the N-terminus in the amino acid sequence of SEQ ID NO: 2 with other amino acid, that is, histidine, arginine, lysine, glutamic acid, serine, threonine, asparagine, glutamine, cysteine, glycine, proline, alanine, valine, isoleucine, leucine, methionine, phenylalanine, tyrosine, or tryptophan;
3) a substitution of the amino acid corresponding to the 45th residue from the N-terminus in the amino acid sequence of SEQ ID NO: 2 with other amino acid, that is, glutamic acid, arginine, histidine, lysine, aspartic acid, serine, asparagine, glutamine, cysteine, glycine, proline, alanine, valine, isoleucine, leucine, methionine, phenylalanine, tyrosine, or tryptophan;
4) a substitution of the amino acid corresponding to the 73th residue from the N-terminus in the amino acid sequence of SEQ ID NO: 2 with other amino acid, that is, valine, arginine, histidine, lysine, aspartic acid, glutamic acid, serine, threonine, asparagine, glutamine, cysteine, glycine, proline, isoleucine, leucine, methionine, phenylalanine, tyrosine, or tryptophan;
5) a substitution of the amino acid corresponding to the 81th residue from the N-terminus in the amino acid sequence of SEQ ID NO: 2 with other amino acid, that is, serine, arginine, histidine, lysine, aspartic acid, glutamic acid, threonine, asparagine, glutamine, cysteine, glycine, proline, valine, isoleucine, leucine, methionine, phenylalanine, tyrosine, or tryptophan;
6) a substitution of the amino acid corresponding to the 101th residue from the N-terminus in the amino acid sequence of SEQ ID NO: 2 with other amino acid, that is, alanine, arginine, histidine, lysine, aspartic acid, glutamic acid, serine, asparagine, glutamine, cysteine, glycine, proline, valine, isoleucine, leucine, methionine, phenylalanine, tyrosine, or tryptophan; and
7) a substitution of the amino acid corresponding to the 113th residue from the N-terminus in the amino acid sequence of SEQ ID NO: 2 with other amino acid, that is, valine, arginine, histidine, lysine, aspartic acid, glutamic acid, serine, threonine, asparagine, glutamine, cysteine, glycine, proline, alanine, leucine, methionine, phenylalanine, tyrosine, or tryptophan.

In one embodiment, in the mutant polypeptide, at least one of amino acids selected from the group consisting of amino acids corresponding to the 39th residue, 43th residue, 45th residue, 73th residue, 101th residue and 113th residue from the N-terminus of the amino acid sequence of SEQ ID NO: 2 is substituted with amino acids different from the original amino acids, in the amino acid sequence of SEQ ID NO: 2.

In one embodiment, in the mutant polypeptide, at least one of amino acids selected from the group consisting of amino acids corresponding to the 39th residue, 72th residue, 101th residue and 113th residue from the N-terminus of the amino acid sequence of SEQ ID NO: 2 is substituted with amino acids different from the original amino acids, in the amino acid sequence of SEQ ID NO: 2.

In one embodiment, in the mutant polypeptide, at least one of amino acids selected from the group consisting of amino acids corresponding to the 43th residue and 45th residue from the N-terminus of the amino acid sequence of SEQ ID NO: 2 is substituted with amino acids different from the original amino acids, in the amino acid sequence of SEQ ID NO: 2.

In one embodiment, in the mutant polypeptide,
(1) at least one of amino acids selected from the group consisting of amino acids corresponding to the 39th residue, 72th residue, 101th residue and 113th residue from the N-terminus of the amino acid sequence of SEQ ID NO: 2 is substituted with amino acids different from the original amino acids, and
(2) at least one of amino acids selected from the group consisting of amino acids corresponding to the 43th residue, 45th residue and 81th residue from the N-terminus of the amino acid sequence of SEQ ID NO: 2 is further substituted with amino acids different from the original amino acids in the amino acid sequence of SEQ ID NO: 2.

In one embodiment, in the mutant polypeptide,
(1) at least one of amino acids selected from the group consisting of amino acids corresponding to the 43th residue and 45th residue from the N-terminus of the amino acid sequence of SEQ ID NO: 2 is substituted with amino acids different from the original amino acids, and
(2) at least one of amino acids selected from the group consisting of amino acids corresponding to the 39th residue, 73th residue, 81th residue and 101th residue from the N-terminus of the amino acid sequence of SEQ ID NO: 2 is further substituted with amino acids different from the original amino acids in the amino acid sequence of SEQ ID NO: 2.

In one embodiment, in the mutant polypeptide,
(1) at least one of amino acids selected from the group consisting of amino acids corresponding to the 39th residue, 43th residue, 35th residue, 72th residue, 101th residue, and 113th residue from the N-terminus of the amino acid sequence of SEQ ID NO: 2 is substituted with amino acids different from the original amino acids, and (2) at least one of amino acids selected from the group consisting of amino acids corresponding to the 81th residue from the N-terminus of the amino acid sequence of SEQ ID NO: 2 is further substituted with amino acids different from the original amino acids in the amino acid sequence of SEQ ID NO: 2.

In one specific embodiment, the mutation may comprise:
a substitution of the amino acid corresponding to the 39th residue from the N-terminus of the amino acid sequence of SEQ ID NO: 2 with serine,
a substitution of the amino acid corresponding to the 43th residue from the N-terminus of the amino acid sequence of SEQ ID NO: 2 with histidine,
a substitution of the amino acid corresponding to the 45th residue from the N-terminus of the amino acid sequence of SEQ ID NO: 2 with glutamic acid,
a substitution of the amino acid corresponding to the 73th residue from the N-terminus of the amino acid sequence of SEQ ID NO: 2 with valine,
a substitution of the amino acid corresponding to the 81th residue from the N-terminus of the amino acid sequence of SEQ ID NO: 2 with serine,
a substitution of the amino acid corresponding to the 101th residue from the N-terminus of the amino acid sequence of SEQ ID NO: 2 with alanine, and
a substitution of the amino acid corresponding to the 113th residue from the N-terminus of the amino acid sequence of SEQ ID NO: 2 with valine, may be introduced to the amino acid sequence of SEQ ID NO: 2.

In one specific embodiment, the mutant polypeptide may,
(1) comprise the amino acid sequence of SEQ ID NO: 6, or consist of the amino acid sequence of SEQ ID NO: 6, or
(2) comprise the amino acid sequence having homology or identity of 96% or more, 96.3% or more, 97% or more, 97.7% or more, 98% or more, 98.5% or more, 99% or more, 99.2% or more, 99.5% or more, or 99.9% or more to the amino acid sequence of SEQ ID NO: 6, or consist of the amino acid sequence.

It is obvious that as long as it shows endolysin activity even if some amino acid sequences except for at least one of amino acids selected from the group consisting of amino acids corresponding to the 39th, 43th, 45th, 73th, 81th, 101th, and 113th amino acid residues from the N-terminus of the amino acid sequence of SEQ ID NO: 2 in the mutant polypeptide is deleted, modified, substituted or added, it may be comprised in the mutant polypeptide of the present application.

For example, it is a case of having addition or deletion of a sequence which does not change the function of the mutant polypeptide of the present application, mutation capable of naturally occurring, silent mutation or conservative substitution in the N-terminus, C-terminus and/or inside of the amino acid sequence.

The "conservative substitution" means substituting one amino acid with another amino acid having similar structural and/or chemical properties. This amino acid substitution may generally occur based on the similarity in polarity, charge, solubility, hydrophobicity, hydrophilicity and/or amphipathic nature of resides. Commonly, conservative substitution may hardly affect or not affect the activity of the protein or polypeptide.

In other words, the mutant polypeptide of the present application may have or comprise an amino acid sequence having homology or identity of 96% or more, 96.3% or more, 97% or more, 97.7% or more, 98% or more, 98.5% or more, 99% or more, 99.2% or more, 99.5% or more, or 99.9% or more to the amino acid sequence of SEQ ID NO: 6, in which amino acid corresponding to at least one (for example, 2 or more, 3 or more, 4 or more, 5 or more, 6 or more, or all of 7) of positions selected from the group consisting of the 39th, 43th, 45th, 73th, 81th, 101th, and 113th from the N-terminus of the amino acid sequence of SEQ ID NO: 2 is substituted with other amino acids different from the original amino acids, or consist of or essentially consist of the amino acid sequence with 96% or more, 96.3% or more, 97% or more, 97.7% or more, 98% or more, 98.5% or more, 99% or more, 99.2% or more, 99.5% or more, or 99.9% to the amino acid sequence of SEQ ID NO: 6, but not limited thereto.

In addition, in one embodiment, the mutant polypeptide of the present application may have or comprise a sequence in which amino acids corresponding to at least one (for example, 2 or more, 3 or more, 4 or more, 5 or more, 6 or more, or all of 7) of positions selected from the group consisting of the 39th, 43th, 45th, 73th, 81th, 101th, and 113th from the N-terminus of the amino acid sequence of SEQ ID NO: 2 is substituted with other amino acids different from the original amino acids, in the amino acid sequence having homology or identity of 98.8% or more, 99% or more, 99.2% or more, 99.4% or more, 99.6% or more, or 99.9% or more to the amino acid sequence of SEQ ID NO: 2, or may consist of or essentially consist of a sequence in which amino acids corresponding to at least one (for example, 2 or more, 3 or more, 4 or more, 5 or more, 6 or more, or all of 7) of positions selected from the group consisting of the 39th, 43th, 45th, 73th, 81th, 101th, and 113th from the N-terminus of the amino acid sequence of SEQ ID NO: 2 is substituted with other amino acids different from the original amino acids, in the amino acid sequence having homology or identity of 98.8% or more, 99% or more, 99.2% or more, 99.4% or more, 99.6% or more, or 99.9% or more to the amino acid sequence of SEQ ID NO: 2, but not limited thereto.

In one embodiment, the mutant polypeptide may
(1) comprise the amino acid sequence of SEQ ID NO: 6 or SEQ ID NO: 7, or consist of the amino acid sequence, or
(2) comprise an amino acid sequence having homology or identity of 96% or more, 96.3% or more, 97% or more, 97.7% or more, 98% or more, 98.5% or more, 99% or more, 99.2% or more, 99.5% or more, or 99.9% or more to the amino acid sequence of SEQ ID NO: 6.

In another embodiment, provides a polynucleotide encoding the mutant polypeptide.

The polynucleotide may comprise the nucleic acid sequence of SEQ ID NO: 12.

In the present description, unless otherwise described, a polynucleotide encoding a polypeptide comprising the amino acid sequence of SEQ ID NO: 6 or SEQ ID NO: 7, or consisting of the amino acid sequence of SEQ ID NO: 6 or SEQ ID NO: 7, may mean
(a) a polynucleotide encoding a polypeptide consisting of the amino acid sequence of SEQ ID NO: 6 or SEQ ID NO: 7 or essentially comprising thereof, and/or
(b) a polynucleotide encoding a polypeptide consisting of the amino acid sequence having homology of 98.5% or more, 99% or more, 99.5% or more, or 99.9% or more to the amino acid sequence of SEQ ID NO: 6 or SEQ ID NO: 7 or essentially comprising thereof, and having (maintaining) endolysin enzymatic function (for example, peptidoglycan hydrolysis activity) and/or antibiotic activity against *Pseudomonas* sp. bacterium, for example, *Pseudomonas aeruginosa*, and/or (c) a polynucleotide comprising the nucleic acid sequence of SEQ ID NO: 12, and a polynucleotide comprising the nucleic acid sequence of SEQ ID NO: 12 may mean (d) a polynucleotide consisting of the nucleic acid sequence of SEQ ID NO: 12 or essentially comprising thereof.

Fusion Polypeptide and Polynucleotide Encoding Thereof

Other embodiment provides a novel fusion polypeptide. The fusion polypeptide may comprise the wild-type polypeptide or the mutant polypeptide (hereinafter, described as "wild-type or mutant polypeptide"), and Cecropin A. The cecropin A may be derived from a moth (*Hyalophora cecropia*), and for example, may comprise the amino acid sequence of SEQ ID NO: 8 or SEQ ID NO: 9, or consist of the amino acid sequence. The polypeptide may have antibiotic activity against gram-negative bacterium.

In one embodiment, the fusion polypeptide may further comprise the wild-type polypeptide or mutant polypeptide, and the cecropin A.

In the fusion polypeptide, the cecropin A (for example, SEQ ID NO: 8 or SEQ ID NO: 9) and the wild-type or mutant polypeptide (for example, a polypeptide comprising the amino acid sequence of SEQ ID NO: 2, SEQ ID NO: 6, or SEQ ID NO: 7) may be linked regardless of the order. In other words, in the fusion polypeptide, the cecropin A and the wild-type or mutant polypeptide may be linked in order of cecropin A and the polypeptide or in order of the polypeptide and cecropin A, from the N-terminus, and for example, it may be linked in order of cecropin A and the polypeptide.

Furthermore, the cecropin A (for example, SEQ ID NO: 8 or SEQ ID NO: 9) and the polypeptide (for example, SEQ ID NO: 2, SEQ ID NO: 6, or SEQ ID NO: 7) may be linked by a peptide linker or be directly linked without a linker.

In one embodiment, the fusion polypeptide may (1) comprise the amino acid sequence of SEQ ID NO: 10 or SEQ ID NO: 11, or consist of the amino acid sequence, or (2) comprise an amino acid sequence having homology or identity of 96% or more, 96.3% or more, 97% or more, 97.7% or more, 98% or more, 98.5% or more, 99% or more, 99.2% or more, 99.5% or more, or 99.9% or more to the amino acid sequence of SEQ ID NO: 10 or consist of the amino acid sequence.

The fusion polypeptide may have excellent antibiotic activity against gram-negative bacterium and/or excellent outer membrane permeabilization, compared to the polypeptide or cecropin A. The fusion polypeptide, polypeptide or cecropin A may be prepared recombinantly or synthetically (for example, chemical synthesis).

In the fusion polypeptide provided in the present description, cecropin A and the polypeptide may be linked by a peptide linker or be directly linked without a peptide linker. The peptide linker may be a polypeptide consisting of any amino acids of 1 to 100, 2 to 50, 1 to 30, 2 to 20, or 2 to 10, and the kind of the amino acid comprised is not limited. The peptide linker may comprise, for example, at least one of amino acid residues selected from the group consisting of Gly, Ser, Leu, Gln, Asn, Thr and Ala, respectively. The amino acid sequence suitable for the peptide linker is known in the art. On the other hand, the length of the linker may be variously determined, within the limit which does not affect the structure and/or function of the fusion protein. For example, the peptide linker may be composed by comprising at least one selected from the group consisting of Gly, Ser, Leu, Gln, Asn, Thr and Ala of 1 to 100, 2 to 50, 1 to 30, 2 to 20, or 2 to 10.

In one embodiment, the peptide linker may be expressed as GSGSGS (SEQ ID NO: 22), $(G)_{4-10}$ (SEQ ID NO: 23), $(GGGGS)_{1-5}$ (SEQ ID NO: 24), $(EAAAK)_{1-5}$ (SEQ ID NO: 25), $(EAAAK)_4(GGGGS)_1$ (SEQ ID NO: 26), etc., but not limited thereto.

Other embodiment provides a polynucleotide encoding the fusion polypeptide.

The polynucleotide may comprise the nucleic acid sequence of SEQ ID NO: 13.

Other embodiment provides a polynucleotide encoding the wild-type or mutant polypeptide, or the fusion polypeptide (for example, SEQ ID NO: 3, SEQ ID NO: 12, or SEQ ID NO: 13).

Recombinant Vector and Recombinant Cell

Other embodiment provides a recombinant vector comprising a polynucleotide encoding the aforementioned wild-type or mutant polypeptide (for example, a polypeptide comprising the amino acid sequence of SEQ ID NO: 2, SEQ ID NO: 6, or SEQ ID NO: 7) or the aforementioned fusion polypeptide (for example, SEQ ID NO: 10 or SEQ ID NO: 11). The recombinant vector may be used as an expression vector.

Other embodiment provides a method for preparation of the wild-type or mutant polypeptide or the fusion polypeptide, comprising expressing the wild-type or mutant polypeptide or fusion polypeptide in an appropriate host cell. The expressing the wild-type or mutant polypeptide or fusion polypeptide in an appropriate host cell may be performed by culturing a recombinant cell comprising the polynucleotide or a recombinant vector comprising the same. The method for preparation of endolysin may further comprise isolating and/or purifying the expressed endolysin, after the expressing.

Introduction of the polynucleotide or vector into a host cell may be performed by appropriately selecting a known transformation method by those skilled in the art. In the present description, the term "transformation" refers to introducing a vector comprising a polynucleotide encoding the polypeptide (the wild-type or mutant polypeptide, or the fusion polypeptide, hereinafter, same) into a host cell to allow a polypeptide encoded by the polynucleotide to be expressed. All of transformed polynucleotides may be included whether inserted and positioned in chromosome of the host cell or positioned extrachromosomally, as long as they can be expressed in the host cell. As long as the polynucleotide can be introduced and expressed into a host cell, the form in which it is introduced is not limited. For example, the polynucleotide may be introduced in a form of an expression cassette which is a gene structure comprising all elements necessary for expressing by itself into a host cell. The expression cassette may comprise expression regulating elements such as an operably linked promoter, a transcription termination signal, a ribosome binding site and/or a translation termination signal, and the like. The expression cassette may be in a form of an expression vector capable of self-replicating. In addition, the polynucleotide may be introduced to a host cell in its own form and be operably linked to a sequence necessary for expression in the host cell. As used herein, the term "operably linked" may mean that an expression regulating element (e.g., promoter) and a polynucleotide are functionally linked to perform transcription regulation (e.g., transcription initiation) of the polynucleotide. Operable linking may be performed using a gene recombination technique known in the art.

The method for transforming the polynucleotide into a host cell may be performed by any method for introducing a nucleic acid into a cell (microorganism), and may be performed by appropriately selecting a transformation technique known in the art depending on the host cell. As the known transformation method, electroporation, calcium phosphate (CaPO₄) precipitation, calcium chloride (CaCl₂) precipitation, microinjection, polyethylene glycol (PEG) precipitation (polyethylene glycol-mediated uptake), DEAE-dextran method, cation liposome method, lipofection, lithium acetate-DMSO method, and the like may be exemplified, but not limited thereto.

In the present description, the term "vector" refers to a DNA structure containing a nucleotide sequence of a polynucleotide operably linked to an appropriate regulatory sequence so as to express a target protein in a suitable host. The regulatory sequence may comprise a promoter capable initiating transcription, any operator sequence for regulating transcription, a sequence encoding a suitable mRNA ribosome binding site, and/or a sequence regulating termination of transcription and/or translation. The vector may be expressed regardless of genome of the host cell, or be integrated in the genome of the host cell, after transformed into an appropriate host cell.

The vector usable in the present description is not particularly limited as long as it can replicate in a host cell, and may be selected among all the commonly used vectors. The example of the commonly used vector may include a natural or recombinant plasmid, cosmid, virus, bacteriophage, or the like. For example, as the vector, pWE15, M13, MBL3, MBL4, IXII, ASHII, APII, t10, t11, Charon4A, and Charon21A and the like may be used as the phage vector or cosmid vector, and pBR-based, pUC-based, pBluescriptII-based, pGEM-based, pTZ-based, pCL-based and pET-based and the like may be used as the plasmid vector. Specifically, pDZ, pACYC177, pACYC184, pCL, pECCG117, pUC19, pBR322, pMW118, pCC1BAC vectors, and the like may be exemplified, but not limited thereto.

The vector may further comprise a selection marker to confirm insertion in the chromosome. The selection marker is to select a cell transformed with a vector, that is, to confirm insertion of the polynucleotide, and it may be used by selecting in genes giving a selectable phenotype such as drug resistance, auxotrophy, resistance to a cytotoxic agent or expression of a surface protein. As only cells expressing a selection marker are survived or different phenotypic characteristics are shown under the environment in which a selective agent is treated, transformed cells can be selected.

Antibiotic

Other embodiment provides an antibiotic, comprising at least one selected from the group consisting of the wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11), a polynucleotide encoding the wild-type or mutant polypeptide, or the fusion polypeptide, a recombinant vector comprising the polynucleotide, and a recombinant cell comprising the polynucleotide or recombinant vector.

Other embodiment, provides a use for using in antibiosis against gram-negative bacterium (impediment (inhibition) of growth (or growth and development) of gram-negative bacterium, sterilization and pest control of gram-negative bacterium, etc.) of at least one selected from the group consisting of the wild-type or mutant polypeptide or the fusion polypeptide, a polynucleotide encoding the wild-type or mutant polypeptide, or the fusion polypeptide, a recombinant vector comprising the polynucleotide, and a recombinant cell comprising the polynucleotide or recombinant vector.

Other embodiment, provides a sterilization method (or pest control method, growth inhibition method) of gram-negative bacterium, comprising applying (or administering) an effective dose of at least one selected from the group consisting of the wild-type or mutant polypeptide or the fusion polypeptide, a polynucleotide encoding the wild-type or mutant polypeptide, or the fusion polypeptide, a recombinant vector comprising the polynucleotide, and a recombinant cell comprising the polynucleotide or recombinant vector to a subject in need of antibiosis against gram-negative bacterium (or sterilization, pest control of gram-negative bacterium, etc.).

Other embodiment, provides a use for using in preparation of an antibiotics, or a use for the manufacture of an antibiotic of at least one selected from the group consisting of the wild-type or mutant polypeptide or the fusion polypeptide, a polynucleotide encoding the wild-type or mutant polypeptide, or the fusion polypeptide, a recombinant vector comprising the polynucleotide, and a recombinant cell comprising the polynucleotide or recombinant vector.

The antibiotic may have an antibiotic effect against gram-negative bacterium.

The gram-negative bacterium may be at least one (for example, 1, 2, 3, 4 or 5) selected from the group consisting of *Pseudomonas* sp. bacterium, *Acinetobacter* sp. bacterium, *Escherichia* sp. bacterium, *Enterobacter* sp. bacterium, *Klebsiella* sp. bacterium and the like.

For example, the *Pseudomonas* sp. bacterium may be *Pseudomonas aeruginosa*, and the *Acinetobacter* sp. bacterium may be *Acinetobacter baumannii*, and the *Escherichia* sp. bacterium may be *E. coli* (*Escherichia coli*), and the *Enterobacter* sp. bacterium may be *Enterobacter aerogenes* (or also known as *Klebsiella aerogenes*) or *Enterobacter cloacae*, and the *Klebsiella* sp. bacterium may *Klebsiella pneumoniae*, but not limited thereto.

In one embodiment, the *E. coli* may be adherent-invasive *E. coli* (or *E. coli* AIEC (Adherent-invasive *E. coli*) strain), *E. coli* ATCC (American type culture collection) strain, *E. coli* UPEC (Uropathogenic *E. coli*) strain, *E. coli* CCARM (Culture collection of antimicrobial resistance microbes) strain, *E. coli* FORC81 strain (colistin-resistant *E. coli*), or *E. coli* Clinical strain, but not limited thereto. In one embodiment, the *E. coli* may be at least one selected from the group consisting of ATCC8739, ATCC25922, ATCC51739, CCARM 1A746, CCARM 1G490, F485, F524, F576, F716, F852, FORC81, UPEC90, UPEC3038, UPEC3042, UPEC3051, UPEC3150, UPEC3151, UPEC3163, UPEC3164, UPEC3168, UPEC3181, ECOR1, ECOR2, ECOR9, ECOR15, ECOR35, ECOR36, ECOR43, ECOR45, ECOR52, and ECOR69 and the like, but not limited thereto.

In one embodiment, the *Acinetobacter baumannii* may be at least one selected from the group consisting of ATCC19606, ATCC17978, CCARM12001, F4, F65, F66, and F67, and the like, but not limited thereto.

In one embodiment, the *Pseudomonas aeruginosa* may be at least one selected from the group consisting of PA01, ATCC15522, F102, F125, F141, F171, and F388, and the like, but not limited thereto.

In one embodiment, the *Enterobacter* aero genes (or also known as *Klebsiella aerogenes*) may be at least one selected from the group consisting of CCARM16006, CCARM16008, CCARM16010, and F276, and the like, but not limited thereto.

In one embodiment, the *Enterobacter cloacae* may be at least one selected from the group consisting of ATCC13047, CCARM0252, and CCARM16003, and the like, but not limited thereto.

The antibiotic provided in the present description may further comprise another antibiotic (the second antibiotic), in addition to at least one selected from the group consisting of the aforementioned wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11), a polynucleotide encoding the wild-type or mutant polypeptide or the fusion polypeptide, a recombinant vector comprising the polynucleotide, and a recombinant cell comprising the polynucleotide, and a recombinant cell comprising the polynucleotide or the recombinant vector (hereinafter, the first antibiotic).

The second antibiotic may be at least one selected from commonly used antibiotics, for example, antibiotics having antibiotic activity against gram-negative bacterium. In one embodiment, the second antibiotic may be a polymyxin-based antibiotic, meropenem, kanamycin, tigecycline, chloramphenicol, azithromycin, ciprofloxacin, or a combination of at least one selected therefrom, but not limited thereto.

In one embodiment, the second antibiotic may be a polymyxin-based antibiotic, and for example, may be polymyxin B, colistin or a combination thereof, but not limited thereto.

In this way, by using the antibiotic (the first antibiotic) in combination with other antibiotic (the second antibiotic), it has an advantage to make it possible to exhibit a synergistic effect by the antibiotic effect of the first antibiotic itself and an excellent antibiotic effect even with the second antibiotic at a low concentration. Due to this, side effects such as toxicity by use of an antibiotic at a high concentration (for example, kidney toxicity, liver toxicity, etc.), and the like may be reduced. In addition, the emergence of antibiotic-resistant bacterium may be inhibited through use in combination of antibiotics of different mechanisms.

Accordingly, one embodiment, provides a combination antibiotic comprising at least one selected from the group consisting of the wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11), a polynucleotide encoding the wild-type or mutant polypeptide or the fusion polypeptide, a recombinant vector comprising the polynucleotide, and a recombinant cell comprising the recombinant vector (hereinafter, the first antibiotic); and (b) the second antibiotic.

In the present description, the term "antibiotic" encompasses all types of agents having growth inhibitory ability and/or killing ability against gram-negative bacterium, and unless otherwise mentioned, it may be interchangeably used with an antibacterial agent, preservative, bactericide, or the like.

In one embodiment, in the combination ratio in case of using the first antibiotic and the second antibiotic in combination, when the concentration (μg/ml) of the second antibiotic is 1, the first antibiotic may be used in combination at a ratio of 0.01 to 1024 μg/ml, 0.01 to 512 μg/ml, 0.01 to 128 μg/ml, 0.01 to 16 μg/ml, 0.01 to 1 μg/ml, 0.03125 to 1024 μg/ml, 0.03125 to 512 μg/ml, 0.03125 to 128 μg/ml, 0.03125 to 16 μg/ml, 0.03125 to 1 μg/ml, 0.5 to 1024 μg/ml, 0.5 to 512 μg/ml, 0.5 to 128 μg/ml, 0.5 to 16 μg/ml, 0.5 to 1 μg/ml, 1 to 1024 μg/ml, 1 to 512 μg/ml, 1 to 256 μg/ml, 1 to 128 μg/ml, 1 to 64 μg/ml, 1 to 32 μg/ml, 1 to 16 μg/ml, 1 to 8 μg/ml, 1 to 4 μg/ml, 1 to 2 μg/ml, 2 to 1024 μg/ml, 2 to 512 μg/ml, 2 to 256 μg/ml, 2 to 128 μg/ml, 2 to 64 μg/ml, 2 to 32 μg/ml, 2 to 16 μg/ml, 2 to 8 μg/ml, 2 to 4 μg/ml, 4 to 1024 μg/ml, 4 to 512 μg/ml, 4 to 256 μg/ml, 4 to 128 μg/ml, 4 to 64 μg/ml, 4 to 32 μg/ml, 4 to 16 μg/ml, 4 to 8 μg/ml, 8 to 1024 μg/ml, 8 to 512 μg/ml, 8 to 256 μg/ml, 8 to 128 μg/ml, 8 to 64 μg/ml, 8 to 32 μg/ml, 8 to 16 μg/ml, 16 to 1024 μg/ml, 16 to 512 μg/ml, 16 to 256 μg/ml, 16 to 128 μg/ml, 16 to 64 μg/ml, 16 to 32 μg/ml, 32 to 1024 μg/ml, 32 to 512 μg/ml, 32 to 256 μg/ml, 32 to 128 μg/ml, 32 to 64 μg/ml, 64 to 1024 μg/ml, 64 to 512 μg/ml, 64 to 256 μg/ml, 64 to 128 μg/ml, 128 to 1024 μg/ml, 128 to 512 μg/ml, 128 to 256 μg/ml, 256 to 1024 μg/ml, 256 to 512 μg/ml, or 512 to 1024 μg/ml, but not limited thereto.

Pharmaceutical Composition

Other embodiment provides a pharmaceutical composition for prevention or treatment of infection of gram-negative bacterium or disease caused by gram-negative bacterium, comprising at least one selected from the group consisting of the wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11), a polynucleotide encoding the wild-type or mutant polypeptide or the fusion polypeptide, a recombinant vector comprising the polynucleotide, and a recombinant cell comprising the polynucleotide or recombinant vector.

Other embodiment provides a use for using in, or a use for the manufacture of a medicine for prevention or treatment of infection of gram-negative bacterium or disease caused by gram-negative bacterium, comprising at least one selected from the group consisting of the wild-type or mutant polypeptide or the fusion polypeptide, a polynucleotide encoding the wild-type or mutant polypeptide or the fusion polypeptide, a recombinant vector comprising the polynucleotide, and a recombinant cell comprising the polynucleotide or recombinant vector.

Other embodiment provides a use for using in preparation of a composition for prevention or treatment of infection of gram-negative bacterium or disease caused by gram-negative bacterium, comprising at least one selected from the group consisting of the wild-type or mutant polypeptide or the fusion polypeptide, a polynucleotide encoding the wild-type or mutant polypeptide or the fusion polypeptide, a recombinant vector comprising the polynucleotide, and a recombinant cell comprising the polynucleotide or recombinant vector.

The pharmaceutical composition provided in the present description may further comprise another antibiotic (the second antibiotic), in addition to at least one selected from the group consisting of the aforementioned:

the wild-type or mutant polypeptide or the fusion polypeptide, a polynucleotide encoding the wild-type or mutant polypeptide or the fusion polypeptide, a recombinant vector comprising the polynucleotide, and a recombinant cell comprising the polynucleotide or recombinant vector.

Other embodiment, provides a pharmaceutical composition for prevention or treatment of infection of gram-negative bacterium or disease caused by gram-negative bacterium, comprising the antibiotic or combination antibiotic as an active ingredient.

Other embodiment provides a method for prevention or treatment of infection of gram-negative bacterium or disease caused by gram-negative bacterium, comprising administering a pharmaceutically effective dose of the antibiotic or combination antibiotic into a subject in need of prevention and/or treatment of infection of gram-negative bacterium or disease caused by gram-negative bacterium. The method for prevention or treatment, may further comprise confirming the subject in need of prevention and/or treatment of infection of gram-negative bacterium or disease caused by gram-negative bacterium, before the administering. The gram-negative bacterium are as described above.

The disease caused by gram-negative bacterium may be selected from all diseases caused by infection of gram-negative bacterium, and for example, it may be selected from the group consisting of disease caused by *Pseudomonas* sp. bacterium such as skin infection, bedsore, pneumonia, bacteremia, sepsis, endocarditis, meningitis, otitis externa, otitis media, keratitis, osteomyelitis, enteritis, peritonitis, or cystic fibrosis, and the like; disease caused by *Acinetobacter* sp. bacterium such as skin infection, pneumonia, bacteremia or sepsis, and the like; disease caused by *Escherichia* sp. bacterium such as enteritis, Crohn's disease, ulcerative colitis, bacillary dysentery, urinary tract infection, skin infection, bacteremia or sepsis, and the like, but not limited thereto.

As used in the present description, a pharmaceutically effective dose means a contained amount or dose of the active ingredient capable of obtaining a desired effect. The contained amount or dose of the active ingredient in the pharmaceutical composition may be variously prescribed by factors such as preparation method, administration method, patient's age, body weight, gender, morbidity, food, administration time, administration interval, administration route, excretion rate and reaction sensitivity. For example, when the active ingredient is a polypeptide, a singe dose may be within a range of 0.001 to 1000 mg/kg, 0.01 to 100 mg/kg, 0.01 to 50 mg/kg, 0.01 to 20 mg/kg, 0.01 to 10 mg/kg, 0.01 to 5 mg/kg, 0.1 to 100 mg/kg, 0.1 to 50 mg/kg, 0.1 to 20 mg/kg, 0.1 to 10 mg/kg, 0.1 to 5 mg/kg, 1 to 100 mg/kg, 1 to 50 mg/kg, 1 to 20 mg/kg, 1 to 10 mg/kg, or 1 to 5 mg/kg, but not limited thereto.

In other embodiment, the content of the active ingredient in the pharmaceutical composition may be 0.01% by weight to 99.9% by weight, 0.01% by weight to 90% by weight, 0.01% by weight to 80% by weight, 0.01% by weight to 70% by weight, 0.01% by weight to 60% by weight, 0.01% by weight to 50% by weight, 0.01% by weight to 40% by weight, 0.01% by weight to 30% by weight, 1% by weight to 99.9% by weight, 1% by weight to 90% by weight, 1% by weight to 80% by weight, 1% by weight to 70% by weight, 1% by weight to 60% by weight, 1% by weight to 50% by weight, 1% by weight to 40% by weight, 1% by weight to 30% by weight, 5% by weight to 99.9% by weight, 5% by weight to 90% by weight, 5% by weight to 80% by weight, 5% by weight to 70% by weight, 5% by weight to 60% by weight, 5% by weight to 50% by weight, 5% by weight to 40% by weight, 5% by weight to 30% by weight, 10% by weight to 99.9% by weight, 10% by weight to 90% by weight, 10% by weight to 80% by weight, 10% by weight to 70% by weight, 10% by weight to 60% by weight, 10% by weight to 50% by weight, 10% by weight to 40% by weight, or 10% by weight to 30% by weight, based on the total weight of the pharmaceutical composition, but not limited thereto.

In addition, the pharmaceutical composition may further comprise a pharmaceutically acceptable carrier, in addition to the active ingredient. The pharmaceutically acceptable carrier may mean a carrier which is commonly used for preparation of a drug comprising a protein, nucleic acid or cell, and does not stimulate an organism and does not inhibit biological activity and/or properties of the active ingredient. In one embodiment, the carrier may be at least one selected from the group consisting of lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, mineral oil and the like, but not limited thereto. The pharmaceutical composition may also comprise at least one selected from the group consisting of a diluent, an excipient, a lubricant, a wetting agent, a sweetener, a flavoring agent, an emulsifier, a suspending agent, a preservative, and the like, commonly used for preparation of a pharmaceutical composition additionally.

The subject for administration of the pharmaceutical composition may be at least one selected from mammals including primates such as human and monkeys, rodents such as mice and rats, livestock such as dogs, cats, pigs, cattle, horses, sheep and goats, and poultry such as chickens, ducks, geese, pheasants, quails and turkeys, and the like, or cells, tissues derived therefrom, or cultures thereof.

The pharmaceutical composition may be administered by oral administration or parenteral administration, or may be administered by contacting to a cell, tissue or body fluid.

Specifically, in case of parenteral administration, it may be administered by subcutaneous injection, intramuscular injection, intravenous injection, intraperitoneal injection, intradermal administration, local administration, intranasal administration, intrapulmonary administration and intrarectal administration and the like. In case of oral administration, as a protein or peptide is digested, the oral composition should be formulated to coat an active agent or to be protected from decomposition. In case of intranasal administration, the pharmaceutical composition may be administered by nasal spray so that it is absorbed to the nasal cavity through a sprayer or spray system by diluting it, and the nasal spray or respiratory formulation for the nasal spray may include an aerosol, and the like.

In addition, the pharmaceutical composition may be formulated in a form of solution in an oil or aqueous medium, injection, suspension, syrup, emulsion, coating agent, patch, extract, powder, granule, tablet, capsule, aerosol, and the like, and for formulation, a dispersing agent or stabilizing agent may be additionally comprised.

Other embodiment provides a feed additive
comprising at least one selected from the group consisting of
the wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11),
a polynucleotide encoding the wild-type or mutant polypeptide, or the fusion polypeptide,
a recombinant vector comprising the polynucleotide, and
a recombinant cell comprising the polynucleotide or recombinant vector.

Other embodiment provides a feed additive, comprising the antibiotic or combination antibiotic as an active ingredient.

Other embodiment provides a feed comprising the food additive composition.

The feed may be prepared by separately preparing the antibiotic or combination antibiotic in a feed additive form to mix to the feed, or directly adding it during feed preparation.

The antibiotic or combination antibiotic in the feed may be in a liquid or dried state, for example, in a dried powder form. The antibiotic may be comprised in an amount of 0.005 to 10% by weight, 0.05 to 10% by weight, 0.1 to 10% by weight, 0.005 to 5% by weight, 0.05 to 5% by weight, 0.1 to 5% by weight, 0.005 to 2% by weight, 0.05 to 2% by weight, or 0.1 to 2% by weight of the total feed weight, but not limited thereto. In addition, the feed may further comprise common additives which can improve preservability of the feed in addition to the antibiotic or combination antibiotic.

In the present description, the feed in which the antibiotic or combination antibiotic can be added may be selected from the group consisting of commercially available feed, or grains, root fruits, food processing by-products, algae, fiber, pharmaceutical by-products, oils and fats, starches, gourds, grain by-products, proteins, inorganic materials, minerals, single cell proteins, zooplankton, leftover food, and the like, but not limited thereto.

Other embodiment provides a food additive or drinking water additive comprising the antibiotic or combination antibiotic as an active ingredient. By supplying the antibiotic or combination antibiotic as mixed in drinking water, the number of gram-negative bacterium in the drinking water may be reduced. The gram-negative bacterium are described as above.

Other embodiment provides a disinfectant,
comprising at least one selected from the group consisting of
the wild-type or mutant polypeptide (for example, SEQ ID NO: 2, SEQ ID NO: 6, or SEQ ID NO: 7) or the fusion polypeptide (for example, SEQ ID NO: 10 or SEQ ID NO: 11),
a polynucleotide encoding the wild-type or mutant polypeptide, or the fusion polypeptide,
a recombinant vector comprising the polynucleotide, and
a recombinant cell comprising the polynucleotide or recombinant vector.

Other embodiment, provides a disinfectant, comprising the antibiotic or combination antibiotic as an active ingredient.

Other embodiment provides a method for disinfecting, comprising applying the antibiotic or combination antibiotic to a subject in need of disinfection. The disinfectant is a generic term for agents to prevent pathogen infection, and may be used for general life disinfectants, disinfectants for food and cooking places and facilities, disinfectants of buildings such as poultry farms and livestock shed, and various kinds of growing supplies including livestock bodies, drinking water, litter, egg seats, transport vehicles, tableware, and the like.

Other embodiment provides a detergent comprising the antibiotic or combination antibiotic as an active ingredient. Other embodiment provides a cleaning method, comprising applying the antibiotic or combination antibiotic to a subject in need of cleaning. As the antibiotic has an antibiotic effect against gram-negative bacterium, it may be applied as a use for cleaning (cleansing) the skin surface or each body part or the like which is exposed or has possibility to be exposed to gram-negative bacterium. The gram-negative bacterium are as described above.

Advantageous Effects

The wild-type or mutant polypeptide or fusion polypeptide provided in the present description has excellent antibacterial efficacy against various gram-negative bacterium, and thus, it is useful as an antibiotic as well as a pharmaceutical composition.

BRIEF DESCRIPTION OF THE DRAWINGS

FIG. 4a shows the domain structure of EC340, mtEC340 and LNT113. It has a predicted lysozyme domain without a cell wall binding domain (CBD). The EC340 of the *E. coli* phage PBEC131 received several substitutions of amino acids (mtEC340). The positions of the substituted amino acids are indicated. In the mtEC340, cecropin A was fused to the N-terminus, and it was named LNT113.

FIG. 4b shows the analysis result of the purified endolysin, EC340 (19.5 kDa), mtEC340 (18.2 kDa) and LNT113 (23.2 kDa) in the SDS-PAGE and follow-up zymogram analysis.

FIG. 5a to FIG. 5d show the antibacterial activity of endolysin (2 μM) against *E. coli* strain (FIG. 5a, FIG. 5c; ATCC 8739, ATCC 25922, CCARM 1A746, CCARM 1B684) and *K. pneumoniae* strain (FIG. 5b, FIG. 5d; ATCC 700603, KCTC 2208, CCARM 10143, F85) in 20 mM Tris-HCl buffer solution (pH 7.5) for 2 hours. Tris buffer was used as a negative control group (Control). The dotted line indicates the detection limit. In addition to the t-test, two-way ANOVA was performed, and it was indicated by a horizontal bar above a vertical bar (* $p<0.05$,  $p<0.01$, * $p<0.001$).

FIG. 6a: The outer membrane permeability of the gram-negative *E. coli* ATCC 8739 was determined by NPN analysis. CecA-EGFP, Cecropin A fused to EGFP; cecA+ mtEC340, cecropin A and mtEC340 were added to the mixture of 2 μM, respectively; PMB, polymyxin B.

Figure 6A:
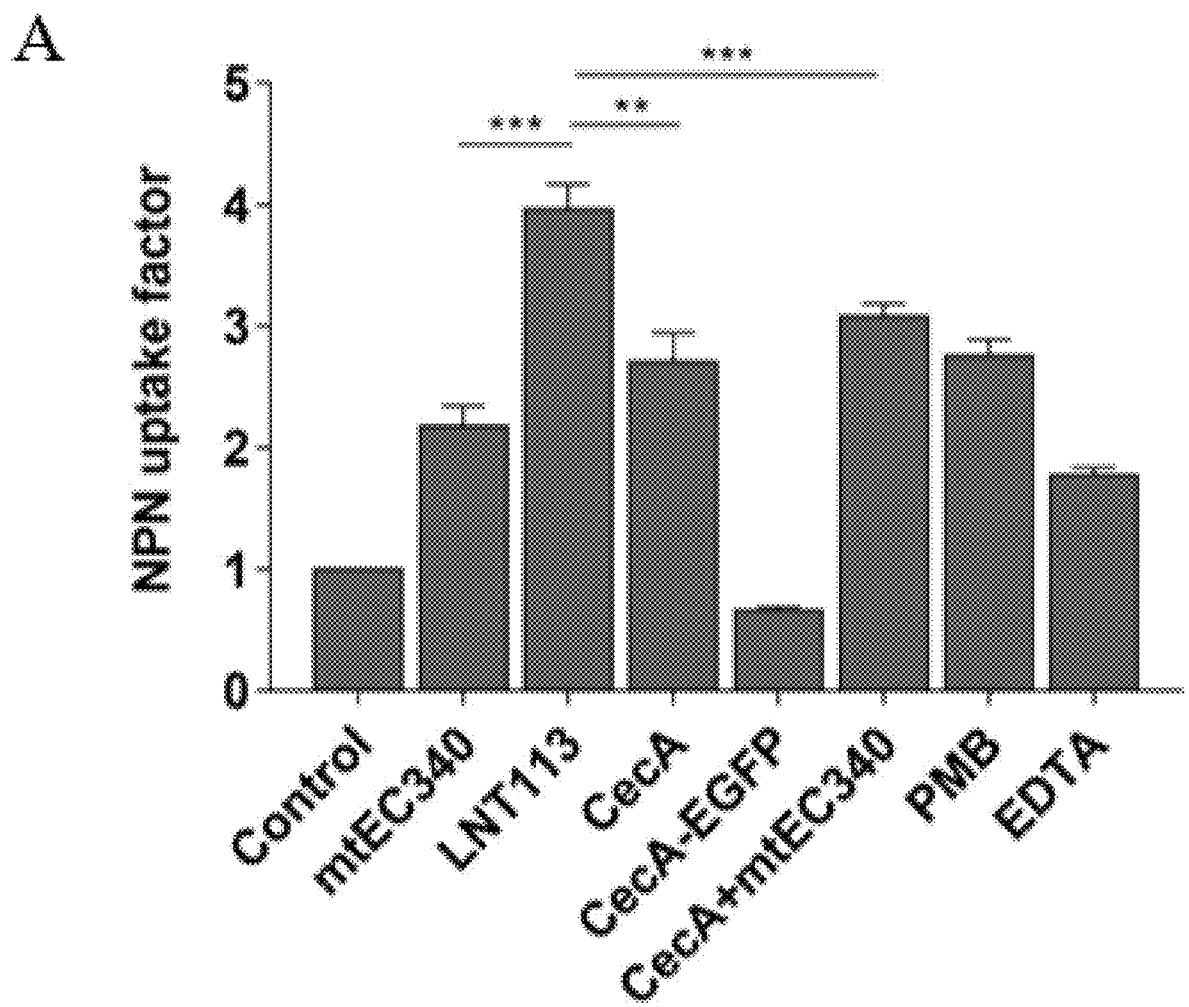
FIG. 6a to FIG. 6e show the cell penetration and antibacterial activity of LNT113.
Figure 6B:
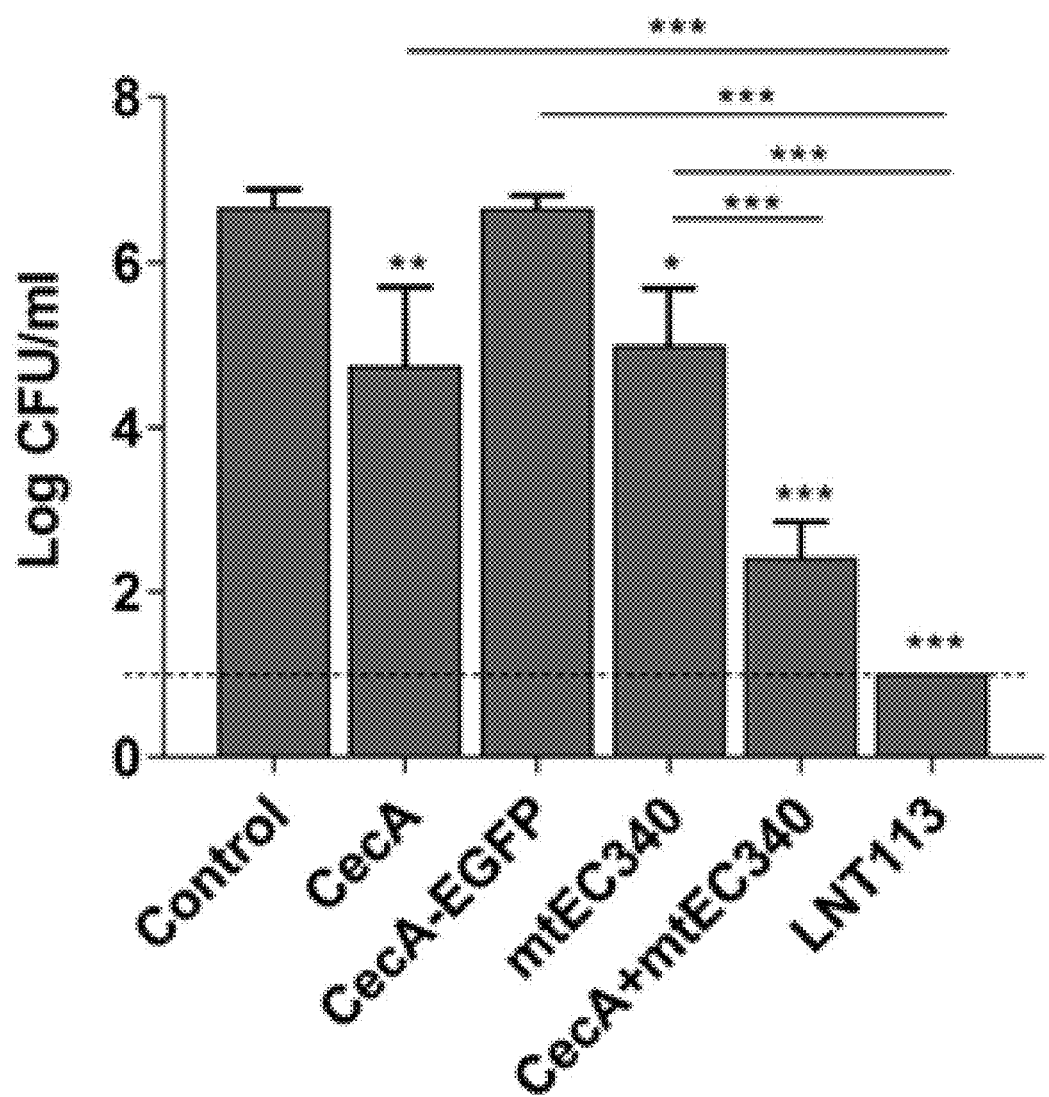

FIG. 6b shows the enhanced antibacterial activity against E. coli ATCC8739 of LNT113 compared to Cecropin A and/or mtEC340. All were treated at the final concentration of 0.5 mM.

Figure 6C:
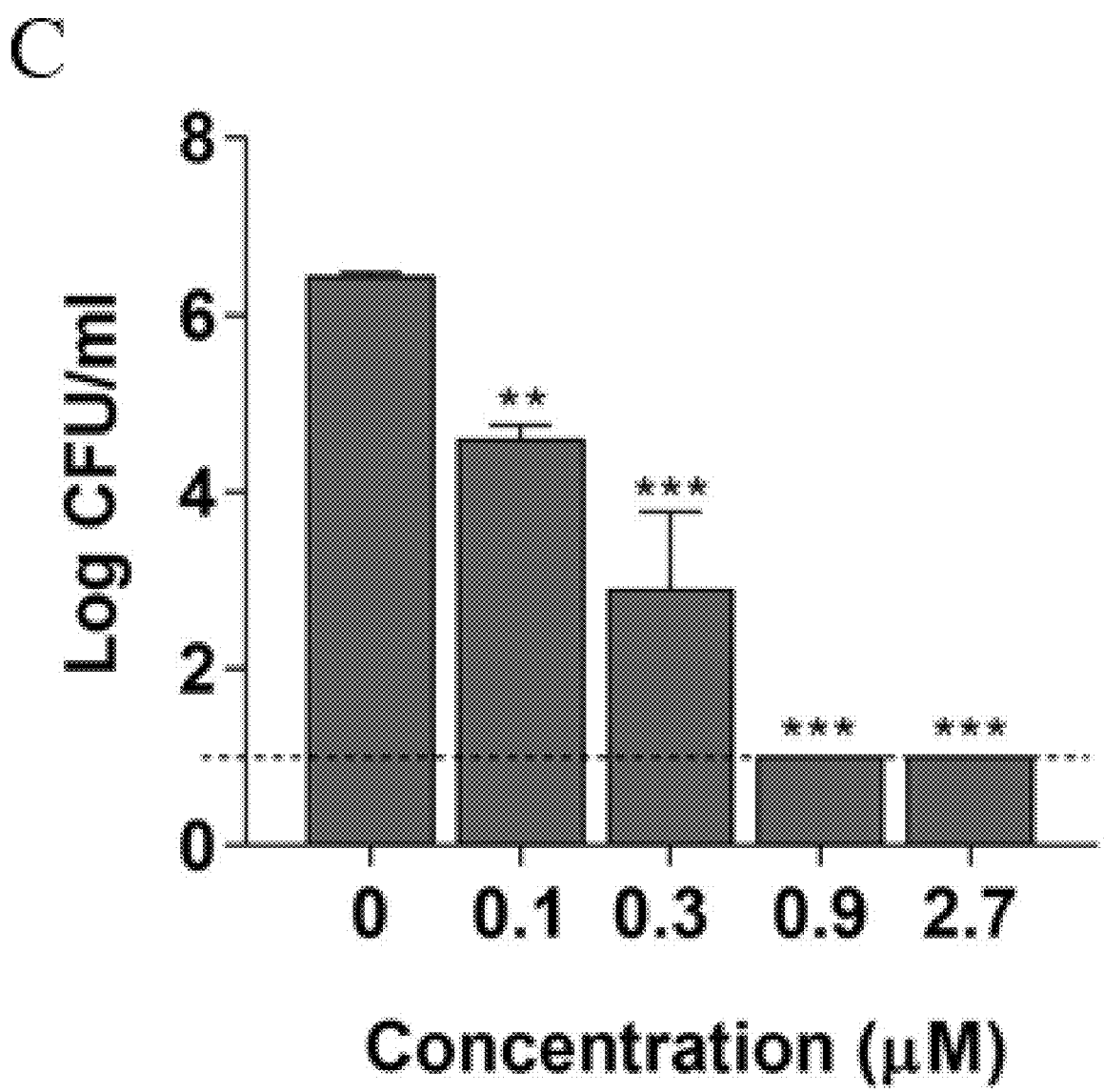

FIG. 6c shows the antibacterial activity of LNT113 (0.1, 0.3, 0.9 or 2.7 μM) at various concentrations against E. coli ATCC 8739.

Figure 6D:
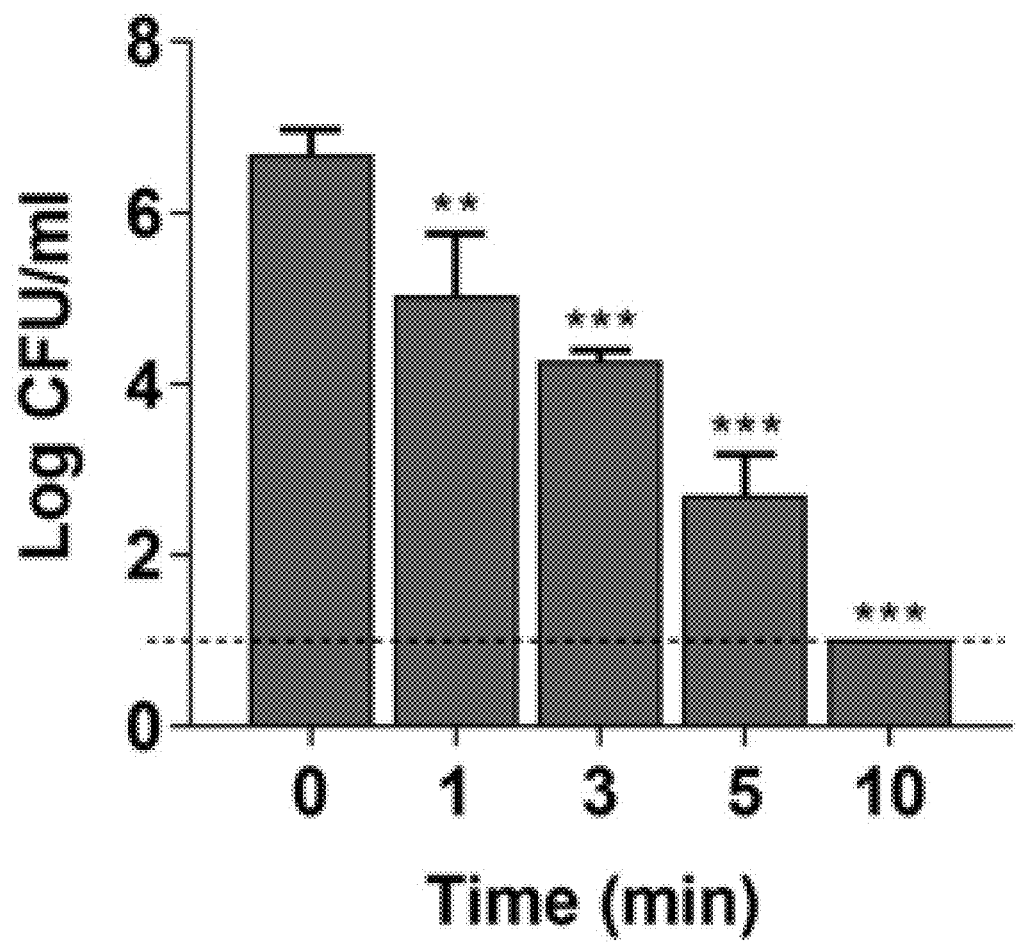

FIG. 6d shows that the survival rate of the bacterium (E. coli ATCC8739) was reduced after adding endolysin (0.5 μM) at different lengths of time. The dotted line indicates the detection limit.

Figure 6E:
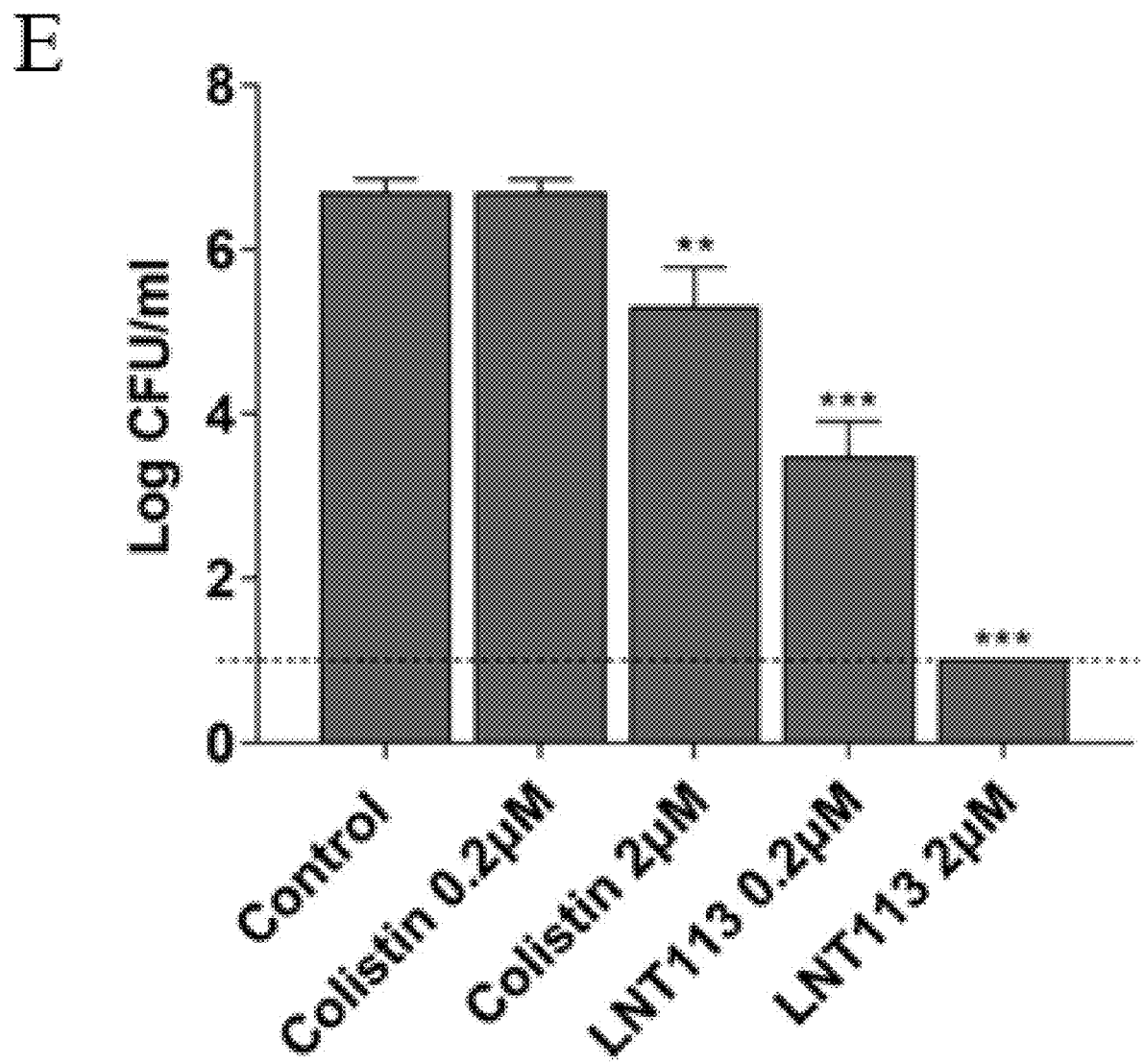

FIG. 6e shows the antibacterial activity of LNT113 against MCR-1 positive E. coli FORC81. Cells were treated with LNT113 or colistin at a concentration of 0.2 or 2 μM for 2 hours. The dotted line indicates the detection limit. The asterisk shows a statistical difference with the control group ($*p<0.05$, $p<0.01$, $*p<0.001$).

Figure 7A:
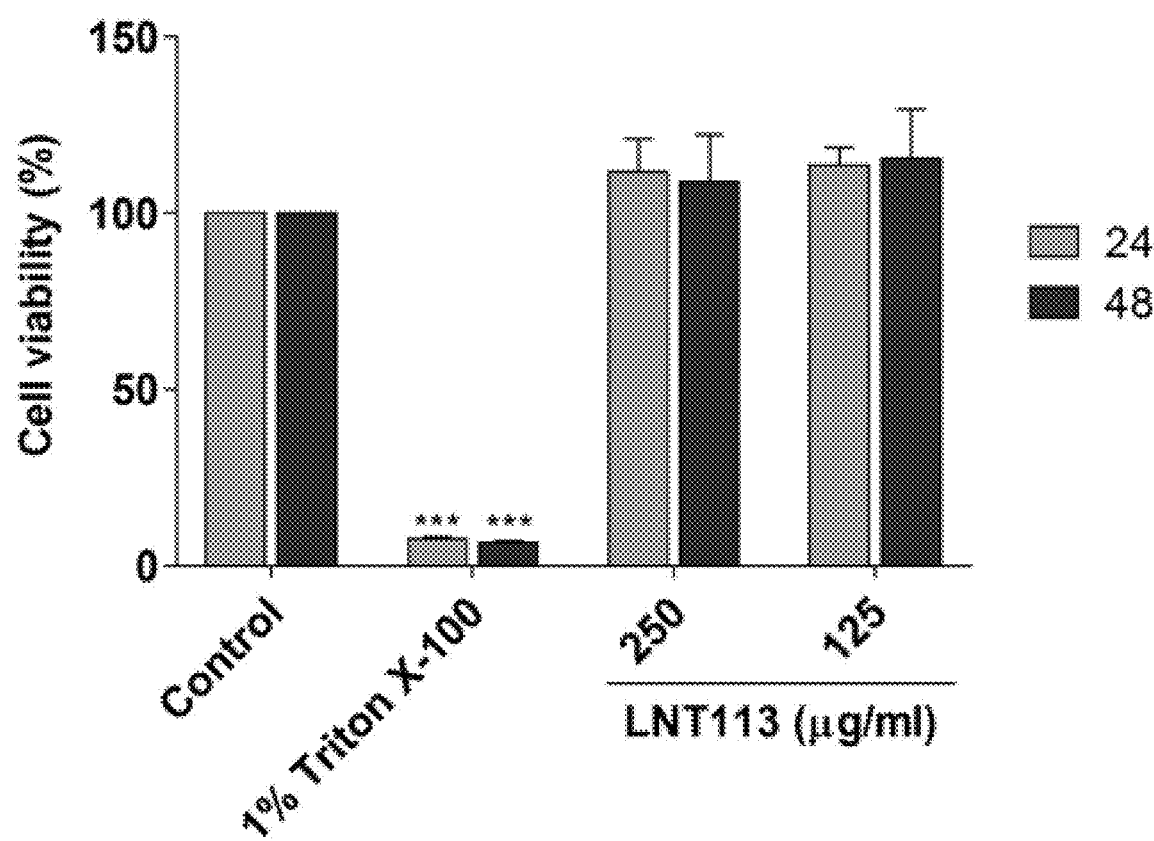
Figure 7B:
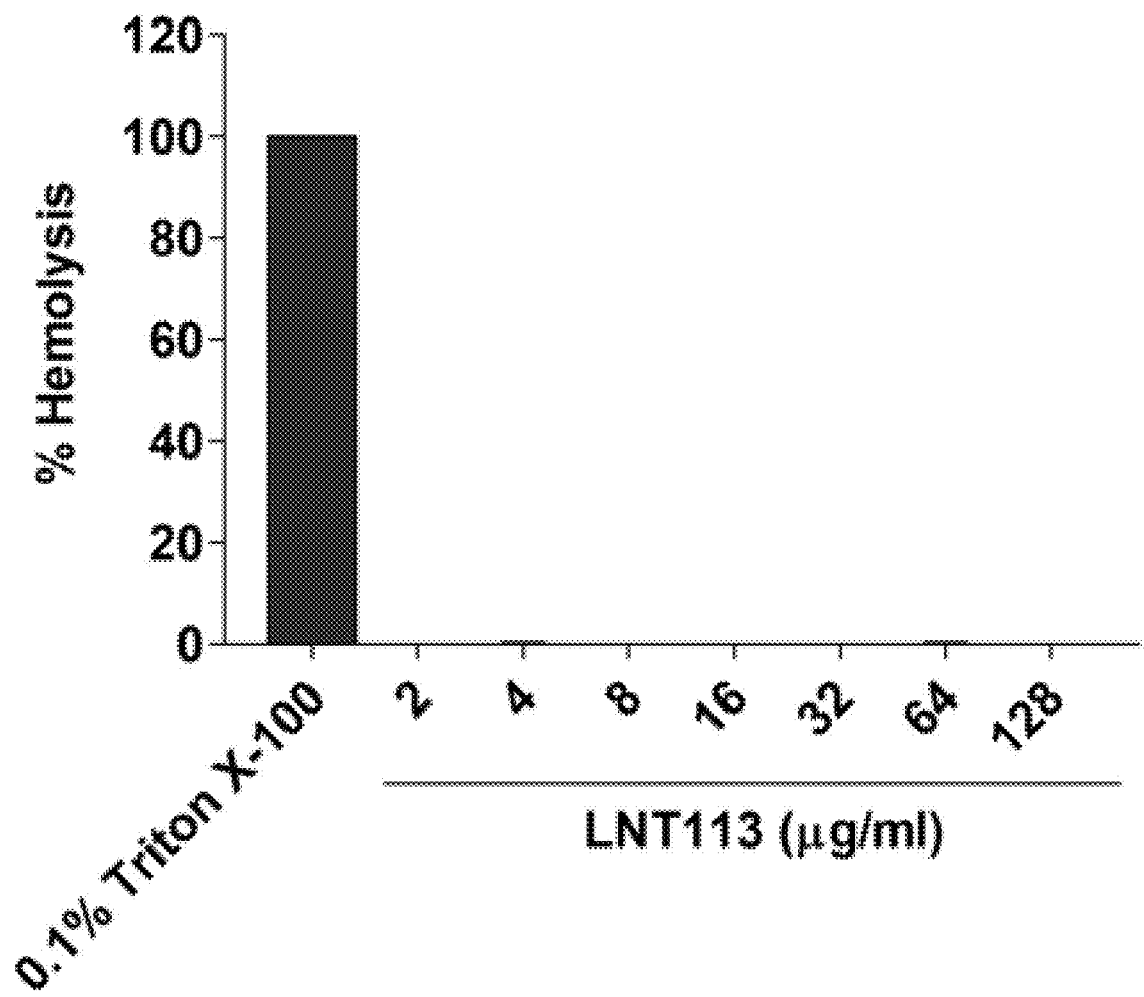

FIG. 7a to FIG. 7b show the cytotoxicity and hemolytic activity of LNT113.

FIG. 7a shows the analysis of the cytotoxicity of LNT113 in the Huh7 cell line. Cells were incubated with LNT113 at a different concentration for 24 hours or 48 hours. As a positive control group of cytotoxicity, Triton X-100 was used.

FIG. 7b shows the hemolytic activity of LNT113. The hemolytic activity was confirmed by culturing red blood cells with PBS or LNT113 at 37° C. for 1 hour and measuring the absorbance of the supernatant at 570 nm. As a positive control group of the hemolytic activity, Triton X-100 0.1% was used.

Figure 8:
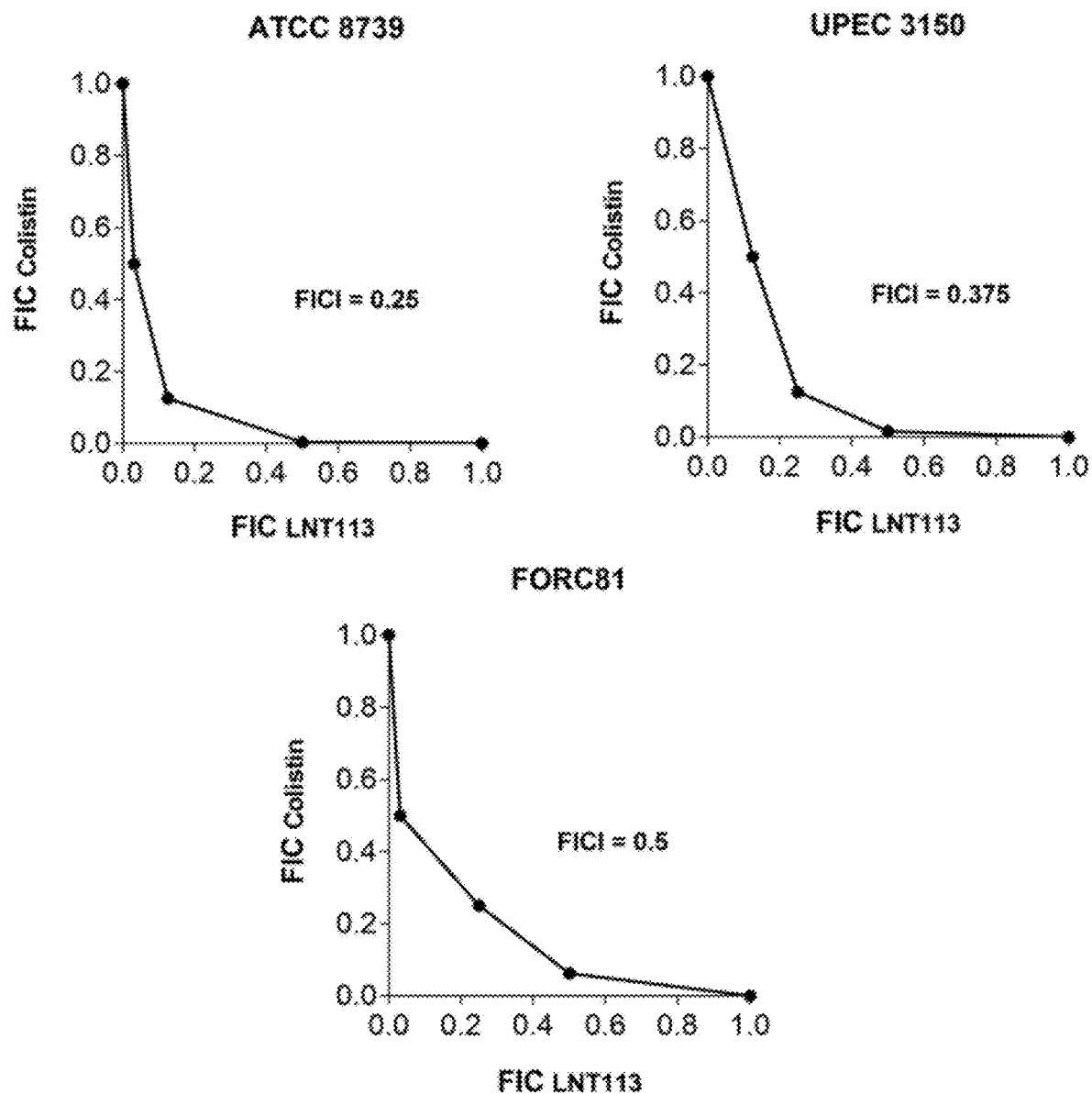

FIG. 8 shows the synergistic effect of LTN113 when treated in combination with colistin against three different E. coli strains. The isobologram. FIC index (FICI) of LNT113 and colistin shows the sum of FIC (Fractional Inhibitory Concentration) of LNT113 and colistin.

FIG. 9 shows the amino acid sequence alignment of putative endolysin used for site-directed mutagenesis of EC340 (CLUSTAL omega) (multiple sequence alignment of EC340 endolysin-like protein using CLUSTAL omega (version 1.2.4)).

Figure 10A:
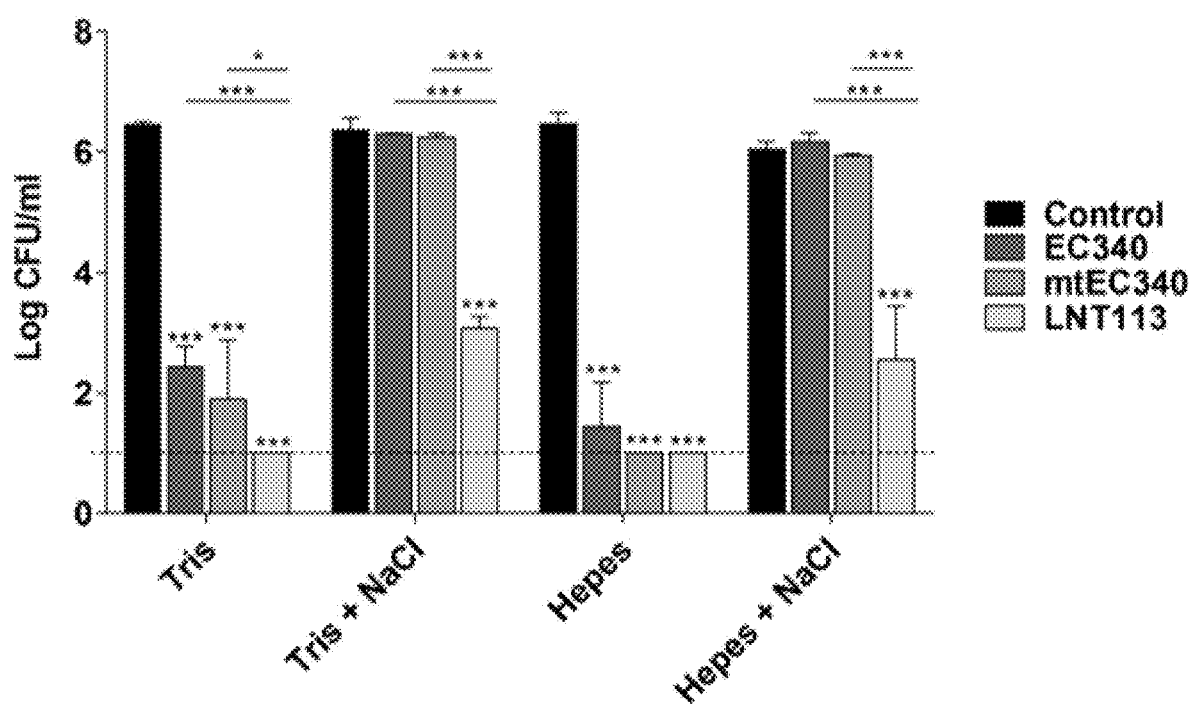
Figure 10B:
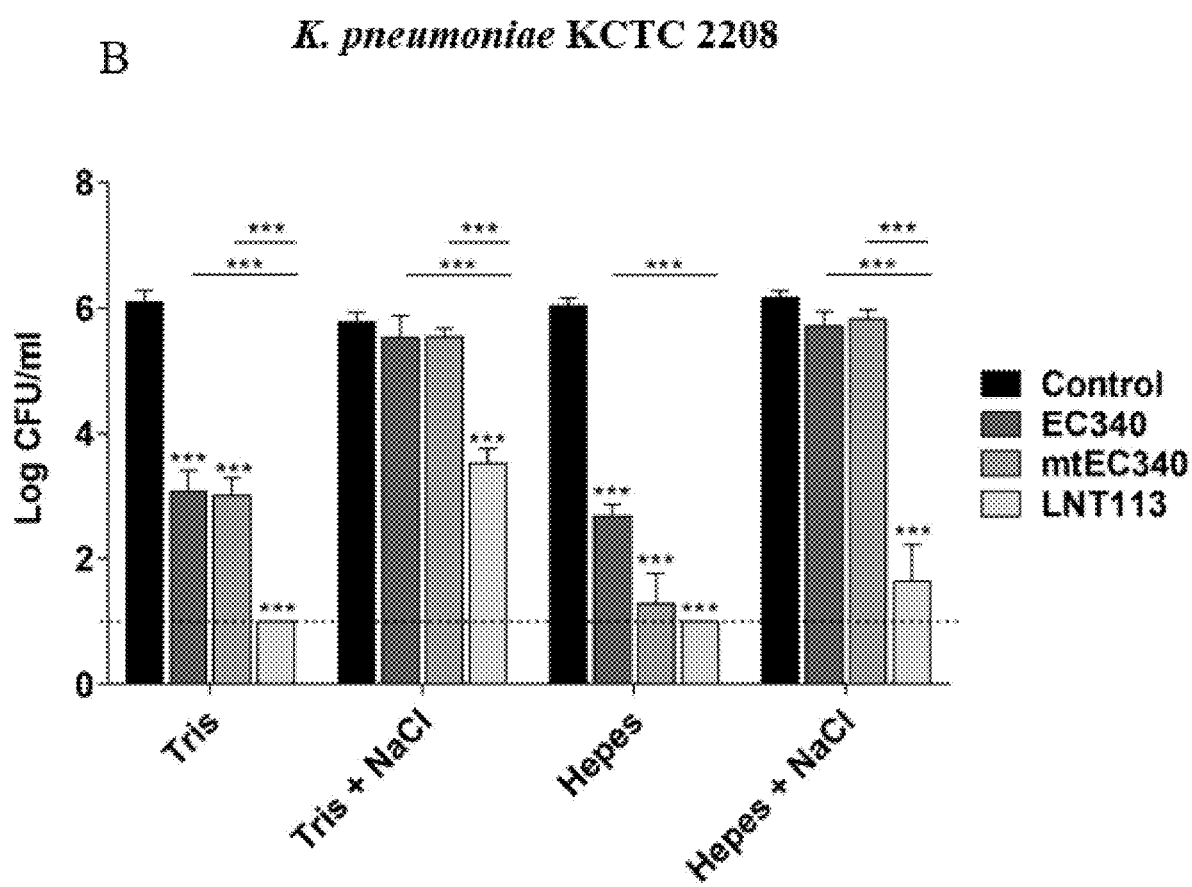

FIG. 10a and FIG. 10b show the antibacterial activity of endolysin against E. coli ATCC8739 (FIG. 10a) and K. pneumoniae KCTC2208 (FIG. 10b). Exponentially grown bacterial cells were cultured with 2 μM endolysin in two different buffer solutions (20 mM Tris-HCl, pH 7.5 or 20 mM HEPES, pH 7.5) in presence or absence of 150 mM NaCl at 37° C. for 2 hours. The dotted line indicates the detection limit. In addition to the t-test, two-way ANOVA was performed, and it was indicated by a horizontal bar above a vertical bar ($* p<0.05$, $p<0.01$, $*p<0.001$).

MODE FOR INVENTION

Hereinafter, the present invention will be described in detail by examples.

The following examples are intended to illustrate the present invention only, and are not construed as limiting the present invention.

Material and Method

Preparation Example 1. Bacteriophage EC340-M-11-12 Isolation and EC340 Endolysin Purification 1.1. Culturing Condition of Strain Escherichia coli (ATCC 8739) was used as a host, and was cultured with shaking in an LB (Luria-Bertani) medium under the condition of 37° C.

1.2. Isolation of Bacteriophage

In order to select a bacteriophage infecting Escherichia coli, samples were collected from Gwacheon Sewage Treatment Plant in Gwacheon-si, Gyeonggi-do, Korea. The collected samples and Escherichia coli were cultured with shaking at 37° C. for 3 hours, and then centrifuged by 500 rpm for 20 minutes to collect the supernatant. After that, the supernatant was filtered with a 0.45 μm filter, and then double agar layer plaque assay was performed.

Briefly describing the assay, the culture solution of the host bacterium Escherichia coli and bacteriophage was mixed with 0.1 M.O.I. to the top agar 5 ml, and poured into an agar plate, and cultured at 37° C. for 24 hours to obtain plaques. It was possible to secure the purified pure bacteriophage through repeated performance of the process, and this bacteriophage was named bacteriophage EC340-M-11-12.

1.3. Genome Isolation and Analysis of Bacteriophage EC340-M-11-12

Sequencing for genome of the bacteriophage EC340-M-11-12 obtained in Preparation example 1.2. above was conducted. After culturing Escherichia coli in an LB medium of 200 ml to $OD_{600}$=0.5, herein, it was lysed by infection with the filtered bacteriophage $10^9$ pfu/ml or 0.1 M.O.I., and then, sodium chloride was added so that the final concentration was to be 1 M, and then was left at 4° C. for 1 hour. Then, after centrifuging at 11,000×g for 10 minutes, PEG (Polyethylene glycol 8000) was added to the precipitate at 10% (w/v), and was placed at 4° C. for 1 hour. After that, it was centrifuged at 11,000×g for 10 minutes, and then the supernatant was removed, and the precipitate was suspended with SM buffer solution [100 mM NaCl, 10 mM $MgSO_4$ (heptahydrate), 50 mM Tris-HCl, pH 7.5]. Herein, chloroform was added at a ratio of 1:1 and vortexed, and then centrifuged at 3,000×g for 15 minutes to obtain a supernatant.

3 ml of 40% (w/v) glycerol was added in a polycarbonate test tube, and then, 4 ml of 5% (w/v) glycerol was added without mixing. Herein, the prepared supernatant was added and centrifuged at 11,000×g at 4° C. for 1 hour. After that, the supernatant was removed, and then the precipitate was resuspended with SM buffer solution to obtain bacteriophage genome DNA. The bacteriophage genome DNA was isolated using a phage DNA isolation kit (Norgen biotek corp.) according to the manufacturer's manual. The nucleotide sequence for genome was analyzed using the genome sample isolated as above (LAS, Illumina MiSeq platform).

The finally analyzed bacteriophage EC340-M-11-12genome has a total nucleic acid sequence length of 42,751 bp. The full-length nucleic acid sequence of the bacteriophage EC340-M-11-12 genome was shown in SEQ ID NO: 1. Based on the genome nucleic acid sequence information, using BLAST on Web, the similarity with the conventionally known bacteriophage genome sequence was investigated. As the result of BLAST investigation, it was confirmed that the genome sequence of the bacteriophage EC340-M-11-12 had the sequence homology of query coverage: 80%, identity: 93.45% to the Escherichia bacteriophage vB_EcoS-Golestan (GenBank accession No.: NC_042084.1). Based on this fact, it was confirmed that the bacteriophage EC340-M-11-12 is a new bacteriophage which is not known conventionally.

1.4. Cloning and Purification of EC340M Endolysin

Through ORF search for the genome sequence (SEQ ID NO: 1) of the bacteriophage EC340-M-11-12 analyzed, it was assumed that the ORF of 489 bp (SEQ ID NO: 3) was an endolysin gene, and the endolysin derived from the bacteriophage EC340-M-11-12 and a gene encoding the same were named EC340 endolysin and EC340 gene, respectively.

Figure 1:
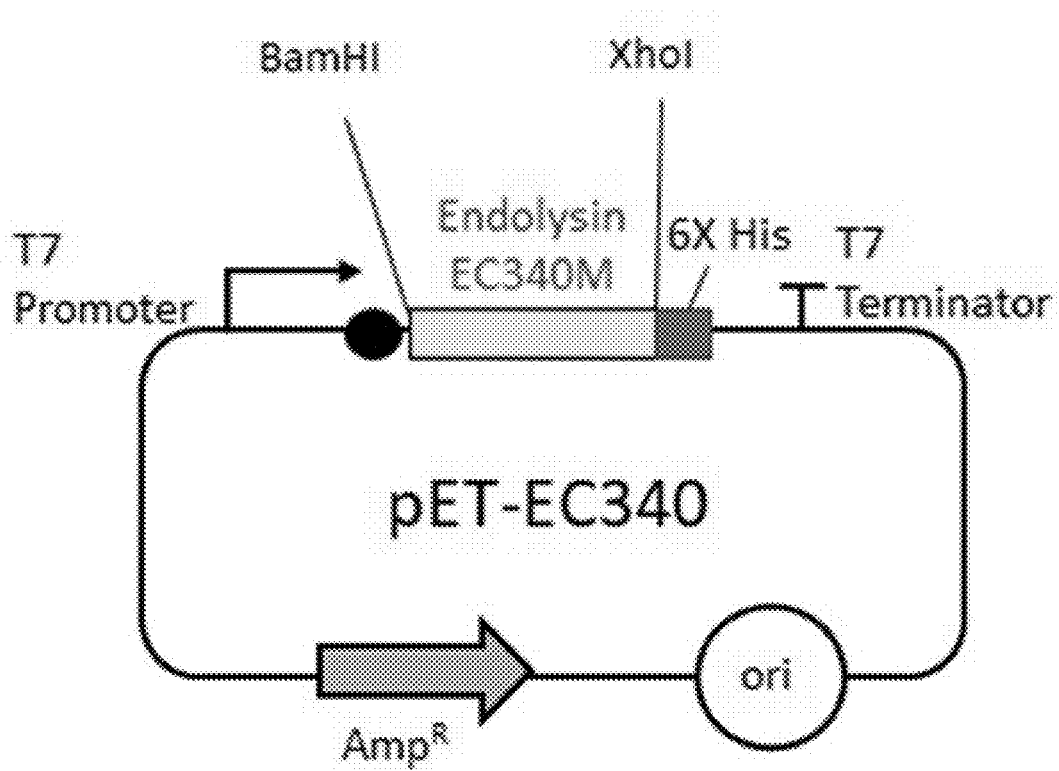
FIG. 1 is a cleavage map of the expression vector expressing the endolysin (EC340) gene of the bacteriophage EC340-M-11-12 infecting *Escherichia coli*.

Using primers (F: 5'-AAGGATCCGTGTCTCGAAA-CATTAGCAACAATGGC-3'(SEQ ID NO: 4), R: 5'-AACTCGAGACCTTTCACCGCGCGCC-3' (SEQ ID NO: 5)), for genome of the bacteriophage EC340-M-11-12, PCR (polymerase chain reaction) was performed to obtain the EC340 gene (nucleic acid sequence of 489 bp length in SEQ ID NO: 1). The amino acid sequence of the EC340 endolysin encoded by the EC340 gene was shown in SEQ ID NO: 2 (162 aa). The PCR was performed under the following condition: step 1: 94° C., 5 minutes; step 2: 94° C., 30 seconds; step 3: 52° C., 45 seconds; step 4: 72° C., 1 minute; step 5: repeating step 2-4 30 times; step 6: 72° C., 10 minutes. The obtained PCR product was cloned with BamHI/XhoI site of pET-21a vector with N-terminal 6× His-tag (Novagen), to prepare an expression vector for expressing the EC340 endolysin (pET-EC340 plasmid). The prepared expression vector pET-EC340 was schematically shown in FIG. 1.

The prepared pET-EC340 plasmid was transformed to *E. coli* BL21-pLysS strain (Novagen), and then cultured in LB broth (1% Tryptone, 0.5% (w/v) Yeast extract, 0.5% (w/v) NaCl) by $OD_{600}$=0.5. Then, 1 mM IPTG (Isopropyl β-d-1-thiogalactopyranosid) was added and then cultured with shaking at 37° C. for 4 hours. After cell harvest, it was resuspended with lysis buffer (50 mM $NaH_2PO_4$, 300 mM NaCl, 10 mM imidazole), and 1 mM PMSF and 1 mg/ml lysozyme were added and it was left on ice for 30 minutes. The cells were lysed by sonication, and centrifuged at 13,000 rpm for 40 minutes to obtain the supernatant. This was passed through a column in which Ni-NTA agarose resin (Qiagen) was packed. After that, after washing with wash buffer (50 mM $NaH_2PO_4$, 300 mM NaCl, 30 mM imidazole), it was eluted with elution buffer (50 mM $NaH_2PO_4$, 300 mM NaCl, 300 mM imidazole), to purify EC340 protein (comprising 6×His tag).

Figure 2:
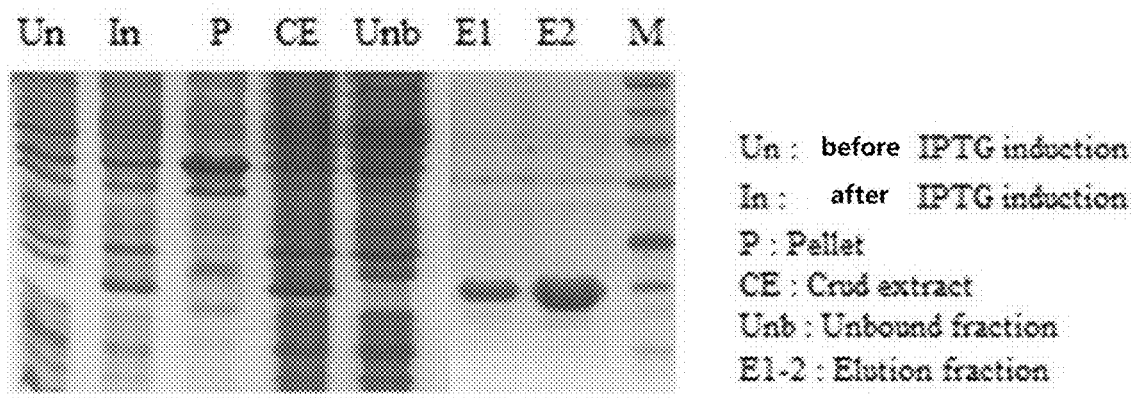
FIG. 2 shows the purification process of the endolysin (EC340) derived from the bacteriophage EC340-M-11-12.

The purity of the EC340 protein was confirmed by 15% SDS-PAGE, and the concentration of the EC340 protein was measured by Bradford assay. The result of confirming each reactant obtained during the purification process was shown in FIG. 2. The molecular weight of the purified EC340 protein confirmed through SDS-PAGE was about 19 kDa.

Preparation Example 2. Bacterium Strain and Culturing Condition

The strain used in the present research was acquired from American Type Culture Collection (ATCC, USA), Korean Collection for Type Cultures (KCTC, Korea) and Culture Collection of Antimicrobial Resistant Microbes (CCRM, Korea). The F strain and uropathogenic *E. coli* (UPEC) strain were clinically isolated and provided by professor KwanSoo Ko (Sungkyunkwan University, College of Medicine). The adherent invasive *E. coli* (Adherent invasive *E. coli* (AIEC)) collection (ECOR) strain was provided by professor Christel Neut (Rahmouni et al., 2018). The MCR-1 positive *E. coli* FORC81 strain was provided by professor Sangryoul Rye (Seoul National University) (Kim et al., 2019). All the strains used in this work were grown in an LB (lysogeny broth) or CAA medium (5 g/l casamino acid, 5.2 mM K2HPO4 and 1 mM MgSO4) at 37° C.

Preparation Example 3. Bacteriophage and Endolysin

The bacteriophage PBEC131 used in the following example was same as obtained in Preparation example 1.

The gene expressing putative endolysin (SEQ ID NO: 3) was obtained from the bacteriophage PBEC131, and the putative lysozyme-like superfamily domain was found by BLASTp.

Preparation Example 4. Molecular Cloning

The gene encoding the putative endolysin of the bacteriophage PBEC131 (SEQ ID NO: 3) was cloned into pET21a+ (Novagen, USA) using BamHI and XhoI restriction sites and named EC340 gene. The EC340 polypeptide was represented by the amino acid sequence of SEQ ID NO: 2.

The mutant EC340 (mtEC340; SEQ ID NO: 6) was produced by substituting 7 amino acids in the amino acid sequence of SEQ ID NO: 2 (FIG. 4a; H39S, D43H, T45E, A73V, A81S, T101A, and I113V).

LNT113 (SEQ ID NO: 10) was constructed by fusing the antibacterial peptide Cecropin A (NCBI PRF 0708214A; SEQ ID NO: 8) with a $(GGGGS)_3$ linker at the N-terminus of the mutant EC340 (mtEC340; SEQ ID NO: 6). (In other words, in the following example, the fusion polypeptide comprising Cecropin A and the mutant polypeptide (mtEC340) was named LNT113.)

All the components used in the examples of the present application have a C-terminal hexa-histidine tag (HHHHHH) for affinity purification. In addition, a gene encoding an enriched green fluorescent protein (EGFP; GenBank accession no. AAB02576.1) was cloned with a gene encoding cecropin A (CecA) at the 5' end into the pET21a+ vector.

```
Used sequences:
Recombinant mtEC340 having the His(6H) tag
[methionine(Met) + mtEC340 (SEQ ID NO: 6) +
His tag(HHHHHH)] (SEQ ID NO: 7)
                                    (SEQ ID NO: 7)
MVSRNISNNGIKFTAAFEGFRGTAYRATPNEKYLTIGYGSYGPHVEPGK

TITPGQGLLLLNRDMAKAVAAVDAVAHHSLTQSQFDAVCDLVYNAGAGV

IAAATGTGKALRSGDVATLRAKLALFINQNGKPLLGLRRRTAGRLALFD

GKPWQEAEAIGRAVKGLEHHHHHH

Recombinant fusion protein LNT113
[methionine(Met) + Cecropin A + GGGGSx3 linker
(SEQ ID NO: 27) + mtEC340 + His tag(HHHHHH)
(SEQ ID NO: 28)] (SEQ ID NO: 11)
                                    (SEQ ID NO: 11)
MKWKLFKKIEKVGQNIRDGIIKAGPAVAVVGQATQIAKGGGGSGGGGSG

GGGSVSRNISNNGIKFTAAFEGFRGTAYRATPNEKYLTIGYGSYGPHVE

PGKTITPGQGLLLLNRDMAKAVAAVDAVAHHSLTQSQFDAVCDLVYNAG

AGVIAAATGTGKALRSGDVATLRAKLALFINQNGKPLLGLRRRTAGRLA

LFDGKPWQEAEAIGRAVKGLEHHHHHH
```

Preparation Example 5. Recombinant Protein Purification

For protein expression, an Endolysin expression vector was introduced to *E. coli* BL21 (DE3) Star (Invitrogen, USA). For expressing a plasmid retaining a gene encoding Cecropin A (CecA) fusion EGFP, it was introduced into *E. coli* BL21(DE3) pLysS (Novagen). After growing cells in an LB broth to an exponential phase (OD600=0.4-0.5), they were induced with isopropyl β-D-1-thiogalactopyranoside (IPTG; Duchefa, The Netherlands) at a concentration of 0.5 mM at 25° C. for 5 hours. Bacterial cells were harvested by centrifugation and pellets were washed with phosphate buffered saline (PBS). Cells were resuspended with dissolution buffer solution (20 mM Tris-HCl, pH 7.5, 300 mM NaCl and 20 mM imidazole) and destroyed by ultrasonication (Sonics, USA) for 5 minutes. The supernatant was obtained from the cell lysate by centrifugation at 15,000×g for 30 minutes. The extract was loaded in a Ni-NTA affinity chromatography column using FPLC (AKTA go, Cytiva, UK). Protein was eluted using a linear gradient of 20 to 500 mM imidazole. The protein was then loaded onto a HiTrap SP HP column (Cytiva) for cation exchange chromatography, and eluted with a linear gradient of NaCl from 0 to 1 M in 20 mM Tris-HCl, pH 7.5. The protein was then dialyzed against storage buffer solution (20 mM Tris-HCl, pH 7.5, 150 mM NaCl buffer solution (pH 7.5)).

Preparation Example 6. Zymogram Assay

Zymogram assay was performed with some modifications of the previously described method (Khakhum et al., 2016). In other words, an overnight culture of E. coli ATCC 8739 was harvested, washed with phosphate buffered solution (PBS) once, and then harvested by centrifugation at 4,000×g for 15 minutes. Then, the pellets were resuspended in 3 ml of deionized water. The cells were autoclaved and added to a 15% SDS-PAGE gel prior to polymerization. Then, 3 µg of purified endolysin (EC340, mtEC340 or LNT113) was mixed with 2× sample buffer (0.5 mM Tris-HCl, pH 6.8, 20% glycerol, 0.2% bromophenol blue) and loaded on SDS-PAGE. After electrophoresis, the gel was washed with deionized water for 1 hour and incubated in reaction buffer (1% Triton X-100, 20 mM Tris-HCl, pH 7.5) at a room temperature. The enzymatic activity of endolysin was observed in a clear area of the gel containing E. coli lysate.

Preparation Example 7. Antibacterial Activity Analysis

The antibacterial activity of the purified protein was tested for E. coli and various K. pneumoniae strains. The bacterium were grown to an exponential phase (OD600=0.5) and harvested by centrifugation at 12,000×g for 3 minutes. Then, the pellets were washed with reaction buffer solution (20 mM Tris-HCl, pH 7.5) and diluted to about $10^6$ cells/ml in the buffer solution. Then, 100 µl bacterial suspension was mixed with the purified endolysin of 100 µl in the reaction buffer solution and incubated at 37° C. for 2 hours. Finally, the mixture was diluted with PBS and loaded on an LB plate. After culturing at 37° C. overnight, the bacterial colonies were counted. All the analysis was performed in triplicate.

The same reaction was performed for the selected subject bacterium in 20 mM HEPES-NaOH, 150 mM NaCl [pH 7.4], and the unique antibacterial activity of Tris and dependence of endolysin for turgor pressure were excluded (FIG. 10a and FIG. 10b). FIG. 10 shows the effect of NaCl for the antibacterial activity of endolysin for E. coli ATCC 8739(A) (FIG. 10a) and K. pneumoniae KCTC 2208(B) (FIG. 10b). The bacterial cells grown geometrically were cultured with 2 µM endolysin in low tonicity buffers (20 mM Tris-HCl, pH 7.5 or 20 mM HEPES, pH 7.5) or high tonicity buffers (buffer solution comprising 150 mM NaCl) at 37° C. for 2 hours. The cells treated with storage buffer solution (20 mM Tris-HCl, pH 7.5, 150 mM NaCl buffer solution (pH 7.5)) were used as a negative control group. The dotted line represents the detection limit (1 Log CFU/ml).

Preparation Example 8. 1-N-Phenylnaphthylamine (NPN) Absorption Analysis

NPN absorption analysis was performed by the previously described method (Helander and Mattila-Sandholm, 2000). In other words, E. coli ATCC 8739 grown to an exponential phase (OD600=0.4) was washed and resuspended with buffer solution (5 mM HEPES, pH 7.2) to about $10^8$ cells/ml. 40 µM NPN (Sigma-Aldrich) 50 µl was mixed with the purified endolysin or Cecropin A (AbClon, Korea) 50 µl so that the final concentration was 2 µM in a 96-well black plate. Outer membrane permeation agents, 1 mM EDTA (Duchefa) and 2 µM Polymyxin B (Sigma-Aldrich) were used as a positive control group. Then, cell suspension 100 µl was added to each well, and cultured at 37° C. for 5 minutes. Buffer alone, buffer+NPN, cell suspension+buffer and cell suspension+buffer+NPN were used as a negative control group. Fluorescence was measured at excitation (350 nm) and emission (420 nm) using a microplate reader (SpectraMax iD3, Molecular Devices, USA). An NPN absorption factor was calculated by dividing the fluorescence value after background removal (the value that the value without NPN subtracted from the fluorescence value of the cell mixture with the sample) with the fluorescence value of the cell suspension with buffer subtracted from the fluorescence value of buffer without NPN.

Preparation Example 9. Hemolysis Analysis

Red blood cells (Sheep RBC) of sheep were used for the in vitro hemolytic activity test. 1 ml red blood cells (MB Cell, Korea) were diluted with 9 ml PBS. Then, 180 µl RBC solution was added to 20 µl LNT113 (final concentration, 2-128 µg/ml), PBS (negative control group) or 0.1% Triton X-100 (positive control group) and cultured at 37° C. for 30 minutes. The mixture was centrifuged at 500×g for 5 minutes, and the supernatant was transferred to a 96-well microplate. Absorbance was measured at 570 nm. The hemolysis rate was calculated using Equation 1 below.

$$\% \text{ Hemolysis} = \left\{ \frac{[\text{Abs(Sample)} - \text{Abs}(negativecontrol)]}{[\text{Abs}(positivecontrl) - \text{Abs}(negativecontrol)]} \right\} \times 100 \quad [\text{Equation 1}]$$

Preparation Example 10. In Vitro Cytotoxicity Analysis

The human hepatocellular carcinoma cell line Huh7 (obtained from Korea Cell Line Bank) was used for cytotoxicity analysis. First, $1 \times 10^4$ Huh7 cells were inoculated in a 96-well plate. After 24 hours, LNT113 (final concentration, 125 or 250 µg/ml), 1% Triton X-100 (positive control group) or PBS (negative control group) was added to the cells and cultured for 24 hours or 48 hours. Then, tetrazolium salt solution 10 µl of WST-8 Cell Viability Assay Kit (Dyne Bio, Korea) was added to each well. Production of formazan was measured at 450 nm after culturing in a 5% CO2 incubator at 37° C. for 1 hour.

Preparation Example 11. Minimal Inhibitory Concentration (MIC) and Minimal Bactericidal Concentration (MB C) Measurement The MIC of the LNT113 or antibiotic was determined using modification of the broth microdilution method in a 96-well, round bottom, microplate according to the previously described method (Heselpoth et al., 2019). Exponentially grown cells were diluted to a concentration of $10^6$ CFU/ml in a CAA medium, and then cultured with recombinant LNT113 (1-64 µg/ml) or antibiotics at 35° C. for 20 hours. The MIC value was determined as the lowest antibacterial concentration that completely inhibited bacterial growth. The MBC was defined as the lowest concentration of the antibacterial agent with no growth on a plate. All analyses were performed in duplicate.

Preparation Example 12. Checkerboard Assay

Checkerboard assay was performed using a serial dilution method as previously described (Thummeepak et al., 2016). LNT113 was vertically diluted 2-fold and the antibiotic was serially diluted horizontally in a 96-well plate. Bacterium at a concentration of $10^6$ CFU/ml were added to each well in a CAA medium. After incubating at 35° C. for 20 hours, the MIC was visually confirmed for non-growing cells. The fractional inhibitory concentration (FIC) for the LNT113 or antibiotic was calculated by dividing the MIC of two drugs by combining it with the MIC of each drug alone. In order to confirm interaction of the two drugs, the FIC index (FICI), which is the sum of the FICs of each drug, was used. The FICI was considered as a synergistic effect ≤0.5, an additive >0.5 ~≤1, an independent effect (indifference)>1.0 ~≤2, and an antagonistic effect (antagonism) >2.

Preparation Example 13. Statistical Analysis

Prism version 9 (GraphPad software) was used for all statistical analysis. For in vitro research, all experiments were performed in triplicate and the result was provided as mean±standard error of mean (SEM). Differences between each data set were compared using two-way Anova with Tukey's multiple comparison test.

Experimental Result

Figure 3:
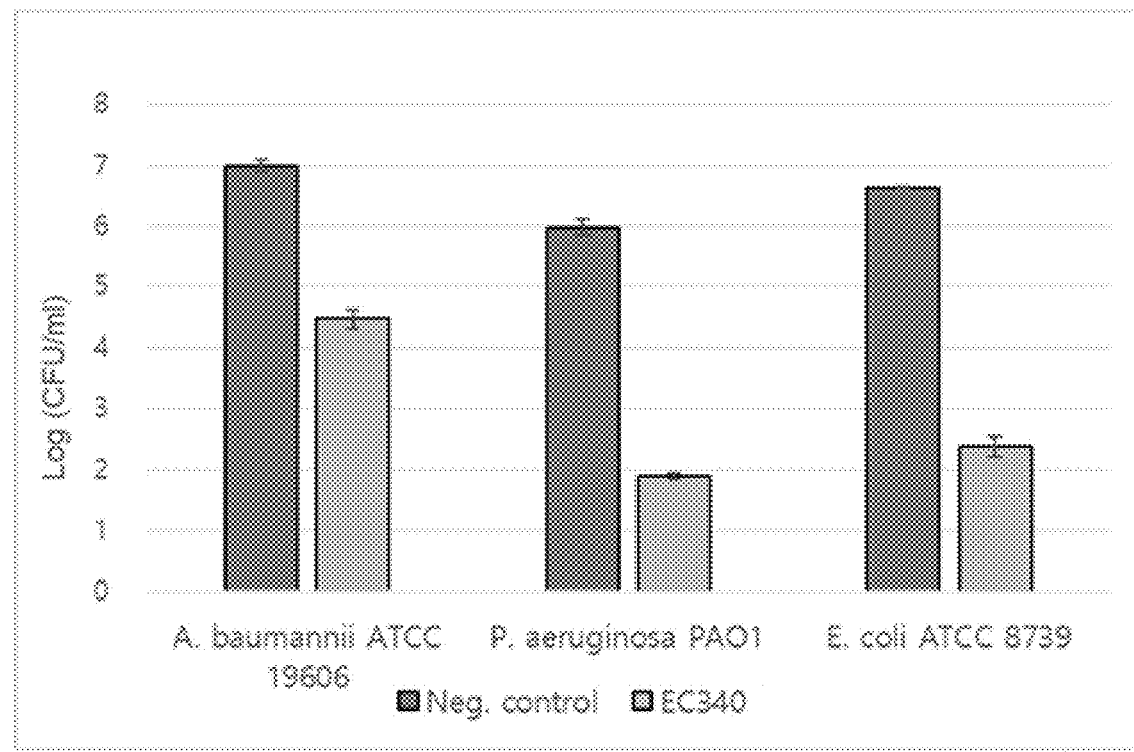
FIG. 3 is a graph showing the antibiotic effect against *Escherichia coli*, *Acinetobacter baumannii* and *Pseudomonas aeruginosa* in vitro of the endolysin (EC340) derived from the bacteriophage EC340-M-11-12.

Example 1. Investigation of Killing Activity of Endolysin EC340 Against Gram-Negative Bacterium In the present example, in order to confirm the antibacterial activity of endolysin EC340 against *Acinetobacter baumannii* (ATCC19606), *Pseudomonas aeruginosa* (ATCC 13388) and *Escherichia coli* (ATCC 8739), the bacterial killing activity was tested.
In Vitro Test For this, endolysin EC340 at a concentration of 2 µM and each test bacterium were added to reaction buffer (20 mM Tris-Cl, pH 7.5) so that the final concentration was to be 200 µl, and were left at 37° C. for 2 hours. After 2 hours, the number of colonies of *Acinetobacter baumannii*, *Pseudomonas aeruginosa* and *Escherichia coli* was confirmed, and the result was shown in FIG. 3. As shown in FIG. 3, it was confirmed that endolysin EC340 had the killing activity against *Acinetobacter baumannii*, *Pseudomonas aeruginosa* and *Escherichia coli*.

Example 2. Bacteriophage PBEC131-Derived Endolysin and Modification Thereof

Figure 4A:
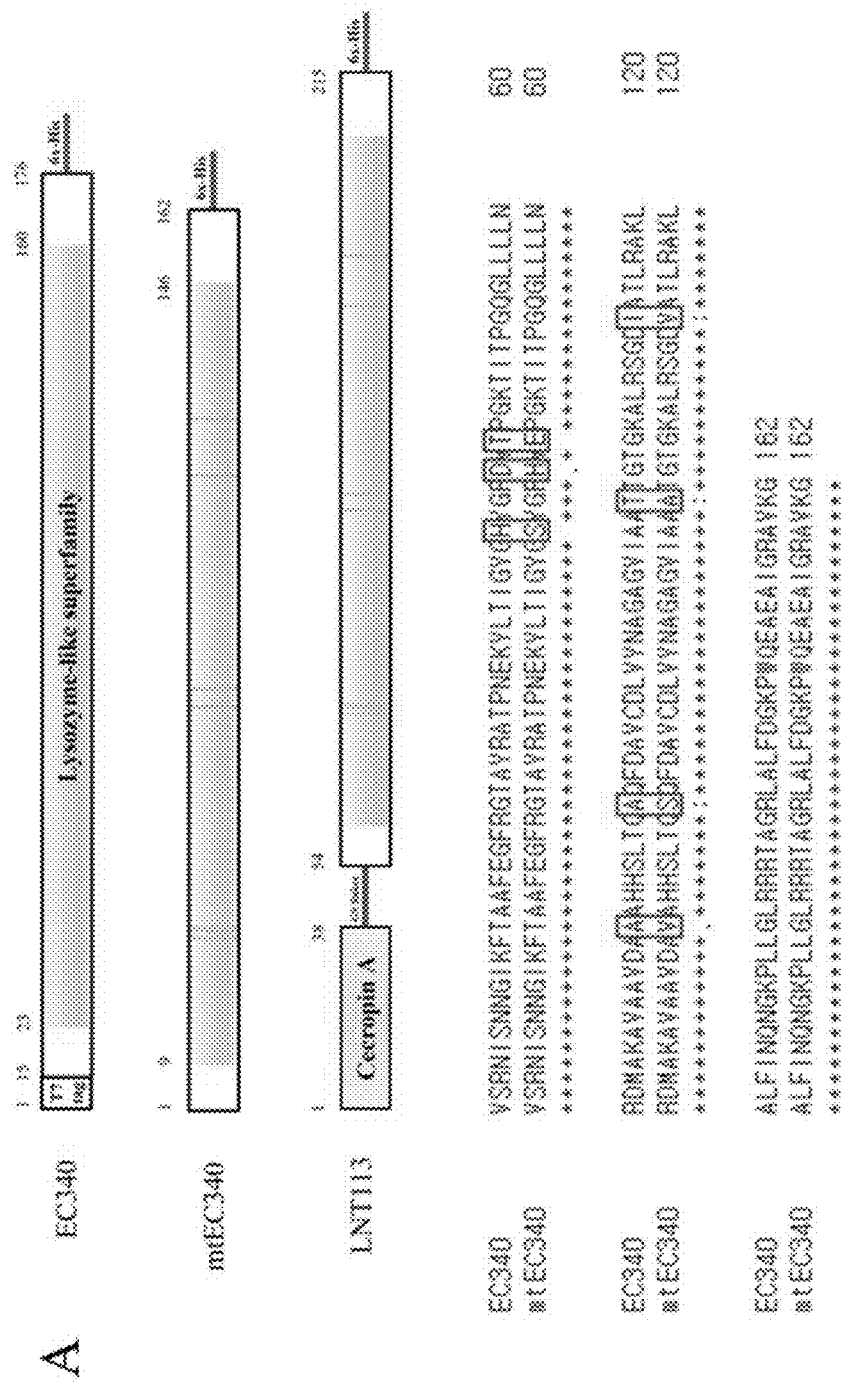
FIG. 4a and FIG. 4b show the composition and enzymatic activity of the endolysin used in the present application.
Figure 4B:
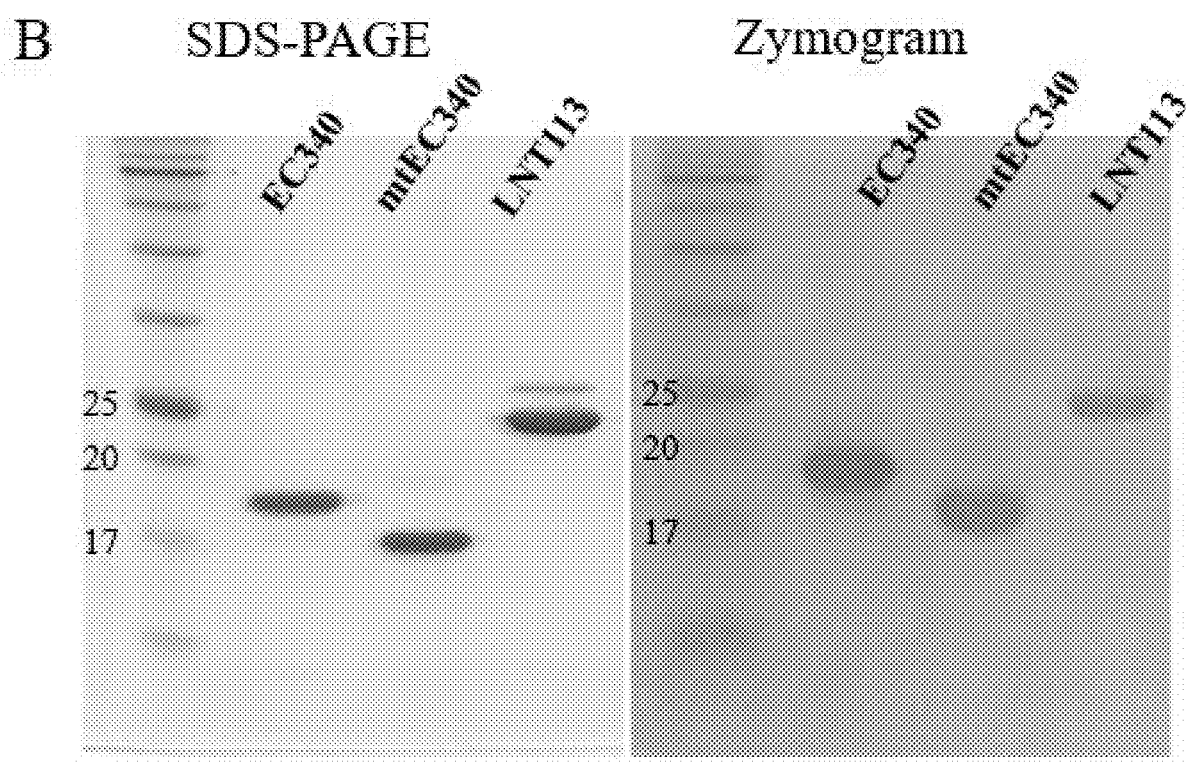
Figure 5A:
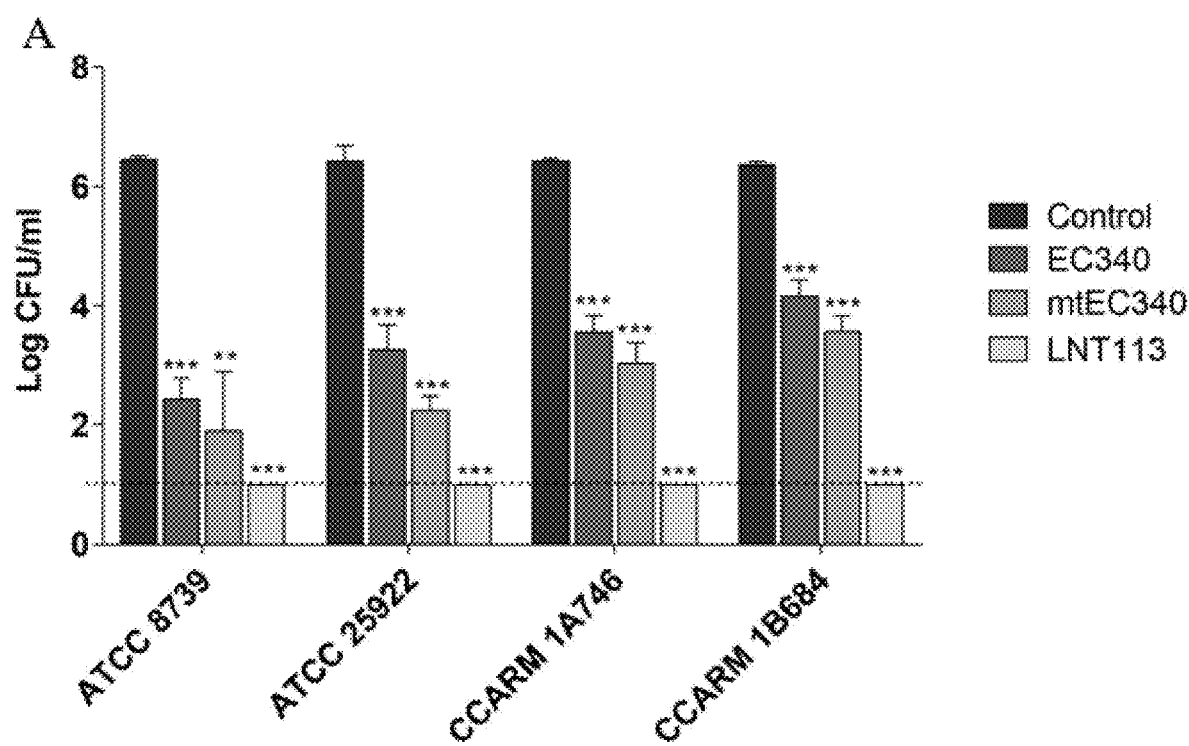
FIG. 5a to FIG. 5d show the antibacterial activity of endolysin.
Figure 5B:
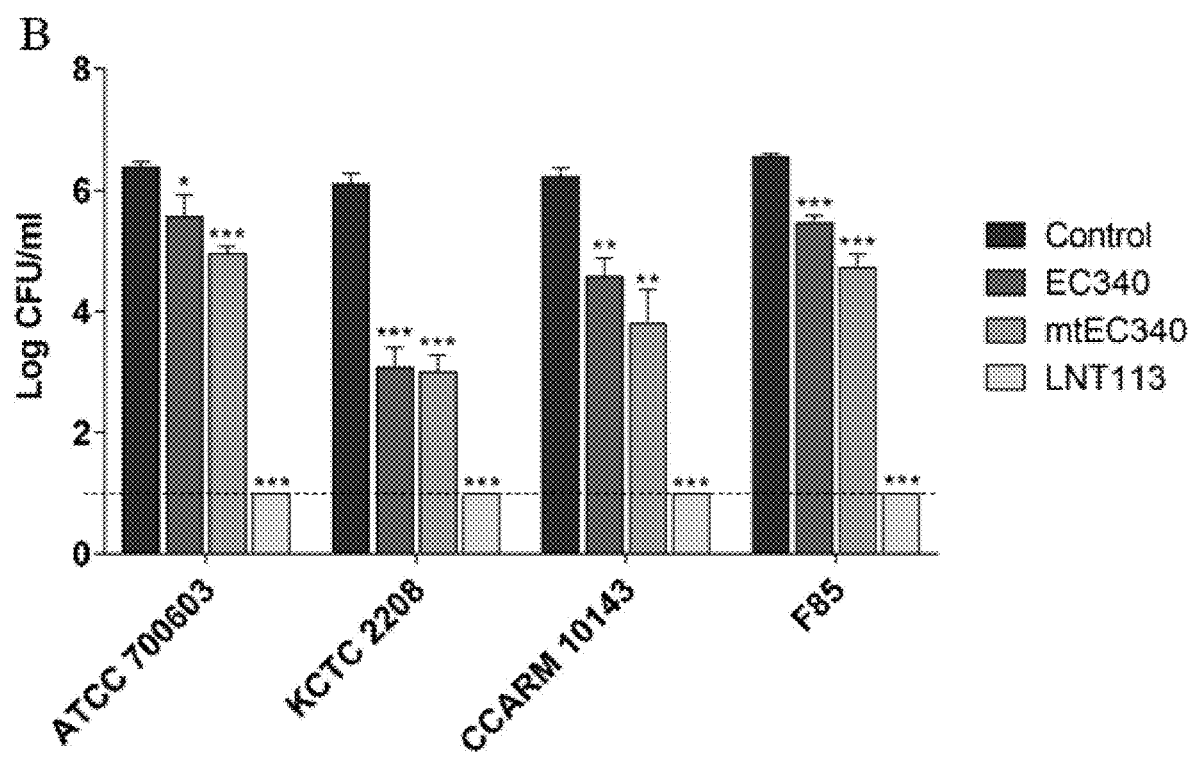
Figure 5C:
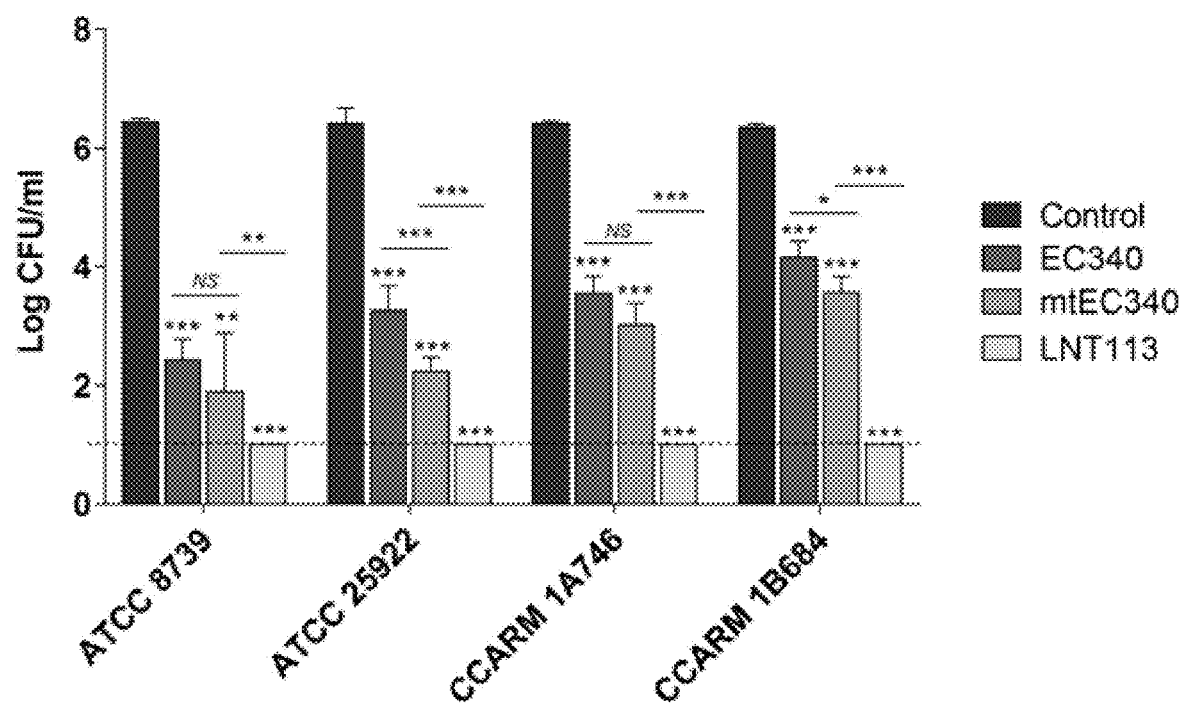
Figure 5D:
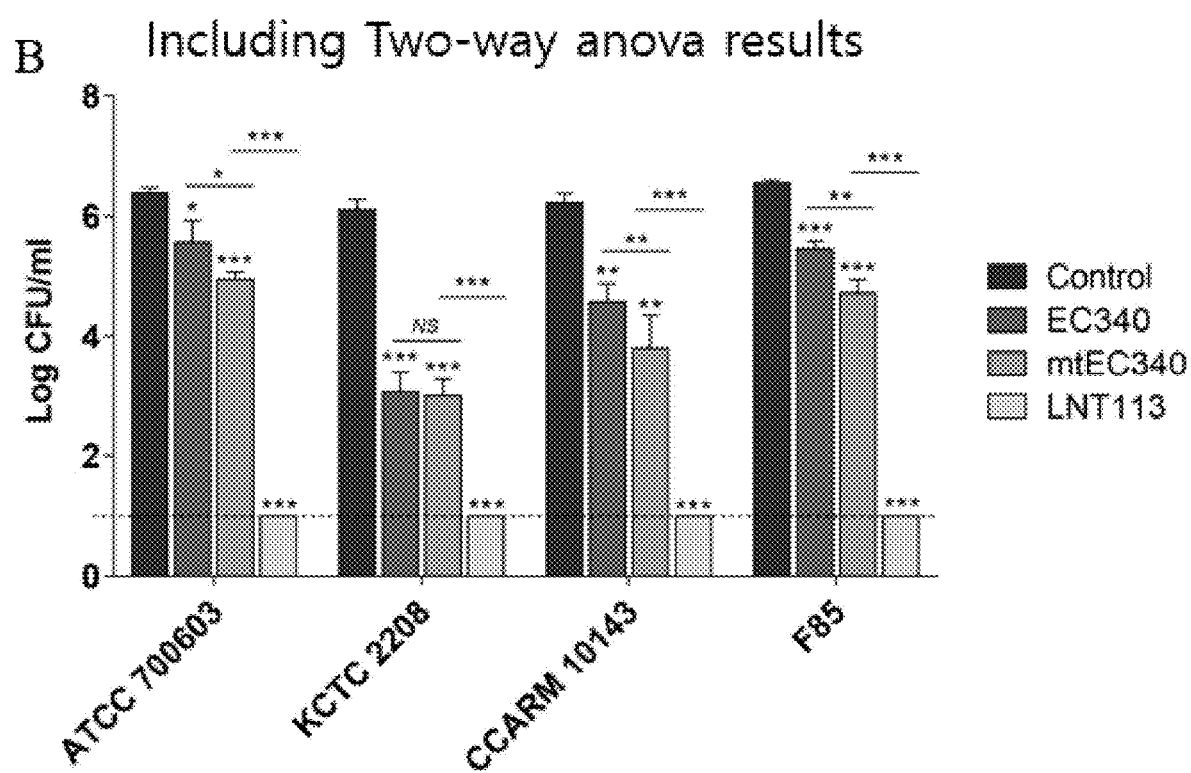

The ORF consisting of 162 amino acids of bacteriophage PBEC131 was annotated with putative endolysin. This endolysin, designated EC340 (SEQ ID NO: 2), has a phage-associated lysozyme (muramidase) domain (pfam00959) (FIG. 4a). This gene was cloned into an expression vector and expressed, and the enzymatic activity was observed by performing zymogram assay with the purified endolysin (See Preparation example 6) (EC340 of FIG. 4b).

To enhance the activity of endolysin, BLASTp was performed with 8 proteins having a sequence very similar to EC340 (GenBank accession no. QQNO11705.1, QN011629.1, QN011777.1, QBJ02951.1, HAM5207786.1, YP_009168880.1, QIG59335.1, and YP_009113200.1) (FIG. 9). In addition, computer-aided modeling of proteins was conducted at https://swissmodel.expasy.org/. In particular, it was thought that changes in amino acids H39S, A73V, T101A and I113V exposed to the outside could lead to better transmembrane by increasing hydrophobicity of proteins. D43H and T45E alterations are in the externally exposed hinge region, where a switch of charged amino acids may result in a more sterically stable property for the corresponding region. The change in A81S located in the third helix region of proteins may not result in noticeable changes in properties of proteins. Mutation was introduced at 7 amino acid positions in the enzymatic active domain of EC340 (FIG. 4a; H39S, D43H, T45E, A73V, A81S, T101A, and I113V), and some changes were made to GRAVY (Grand average of hydropathicity index; index used to indicate a hydrophobicity value of a peptide). In other words, the mutant polypeptide mtEC340 represented by the amino acid sequence of SEQ ID NO: 10 is a polypeptide in which H39S, D43H, T45E, A73V, A81S, T101A, and I113V mutations are introduced, in EC340 represented by the amino acid sequence of SEQ ID NO: 2.

The mtEC340 mutation showed the increased antibacterial activity by up to 1 log at maximum (FIG. 5a to FIG. 5d) when tested against various strains of *E. coli* or *K. pneumoniae* including type strains, drug-resistant strains and clinically isolated strains (resistance profiles are shown in Table 1 below). Higher antibacterial efficacy against endolysin was observed in *E. coli* than *K. pneumoniae*. This is consistent with the previous report that the capsule thickness of *K. pneumoniae* is 16 times or more than that seen in *E. coli*.

TABLE 1

| MIC of various antibiotics against drug-resistant strains | | | |
|---|---|---|---|
| MIC (µg/ml) | *E. coli* | | *K. pneumoniae* |
| of antibiotics | CCARM 1A746 | CCARM 1B684 | CCARM 10143 |
| Ampicillin | ≥128 | ≥128 | ≥128 |
| Cephalothin | ≥128 | 64 | ≥128 |
| Ciprofloxacin | 128 | 64 | ≤0.25 |
| Gentamicin | ≥128 | 128 | ≥128 |
| Tetracycline | 128 | ≥128 | 2 |
| Cefotaxime | 128 | 0.25 | 16 |
| Trimethoprim-sulfamethoxazole | ≥128 | — | ≥32 |
| Streptomycin | ≥128 | ≥128 | — |
| Norfloxacin | ≥128 | 32 | — |

Source: http://knrrb.ccarm-bio.or.kr
—: not determined

In other words, as could be confirmed in FIG. 5a to FIG. 5d, as the result of measuring the number of bacterium in case of treating nothing (control), treating EC340, treating mtEC340 and treating LNT113 to *E. coli* ATCC8739, *E. coli* ATCC25922, *E. coli* CCARM1A746, *E. coli* CCARM1B684, *K. pneumoniae* ATCC700603, *K. pneumoniae* KCTC2208, *K. pneumoniae* CCARM10143, and *K.* pneumoniae F85 strains, the excellent antibacterial activity was shown in all the EC340, mtEC340, and LNT113. It was confirmed that the mtEC340 and LNT113 showed more excellent antibacterial activity among them.

Furthermore, ATCC700603, one of *K. pneumoniae* strains used in the present experiment, was known to have a capsule structure. Thick capsules have the potential to impede endolysin access to the peptidoglycan cell wall. *K. pneumoniae* capsule polysaccharides have been reported to mediate resistance to antibacterial peptides. In order to further increase the activity, 37 amino acid sequences (SEQ ID NO: 8) of cecropin A, which is an antibacterial peptide, were fused to the N-terminus of mtEC340, thereby constructing endolysin LNT113 (SEQ ID NO: 10). This showed a maximum 4-log increase in activity when compared to mtEC340. No viable bacterial cells were detected after culturing for 2 hours for all the tested strains. Since the antibacterial activity of endolysin is potentially dependent on turgor pressure and Tris itself can act as an outer membrane permeation agent, additional antibacterial analysis was performed under various physiological conditions (Tris buffer comprising 150 mM NaCl or Hepes buffer comprising 150 mM NaCl (FIG. 10*a* and FIG. 10*b*)). Unexpectedly, the antibacterial activity was higher in Hepes buffer than Tris buffer without NaCl. However, adding NaCl almost inactivated EC340 and mtEC340. However, as previously reported, the negative effect of salt presence was significantly reduced when cecropin A-fused endolysin (LNT113) was used.

Example 3. Antibacterial Efficacy Enhanced by Enhanced Cell Permeability of LNT113

In general, it is difficult for external endolysin to reach the peptidoglycan layer because of presence of an outer membrane in gram-negative bacterium. Fusion with cecropin A interacting with the outer membrane should increase membrane penetration.

Through NPN (1-N-phenylnaphthylamine) analysis (See Preparation example 8), the transmembrane ability of various members including cecropin A and/or endolysin was compared (FIG. 6*a*).

As could be confirmed in FIG. 6*a* (outer membrane permeability of *E. coli* ATCC 8739), it was observed that the membrane penetration was increased 1.8 times in the cells treated with LNT113 fused with cecropin A (LNT113 of FIG. 6*a*). It was also 1.3-fold higher than that of cecropin A alone (CecA of FIG. 6*a*). In addition, when mtEC340 and cecropin A were co-administered (CecA+mtEC340 in FIG. 6*a*), the membrane permeability was increased. Conversely, cecropin A fused to EGFP (CecA+EGFP of FIG. 6*a*) showed a limited ability to permeate the membrane when compared to LNT113, and this suggests that the partnership of AMP and endolysin showing a strong ability to permeate the membrane is necessary to achieve an additional effect.

The bactericidal efficacy of each construct shown in FIG. 6*b* was proportional to its ability to permeate the membrane as shown in FIG. 6*a*. In vitro, LNT113 exhibited the antibacterial activity according to dose and time (*E. coli* ATCC 8739 (FIG. 6*c*) and FIG. 6*d*). *E. coli* FORC81, a colistin-resistant strain, was tested for susceptibility to LNT113 (*E. coli* FORC81 (FIG. 6*e*)). A 1.2-log decrease was observed in colistin-treated cells at a concentration of 2 μM, whereas at the same concentration, LNT113 succeeded in reducing the amount of bacterial cells below the detection limit.

Example 4. Determination of Minimal Inhibitory Concentration (MIC)

*E. coli* is related to various disease of humans and animals. Pathogenic *E. coli* causes disease by forming colonies in various parts of the human body, such as urinary tract, kidney, bloodstream and the like. Through MIC measurement (See Preparation example 11), the antibacterial activity of LNT113 in various *E. coli* strains was confirmed (Table 2).

TABLE 2

MIC and MBC of LNT113 for various *E. coli* strains

| Strains | MIC | MBC | Strains | MIC | MBC | Strains | MIC | MBC |
|---|---|---|---|---|---|---|---|---|
| ATCC 8739 | 8 | 8 | UPEC 90 | 64 | 64 | ECOR 1 | 8 | 8 |
| ATCC 25922 | 64 | 64 | UPEC 3038 | 16 | 16 | ECOR 2 | 8 | 8 |
| ATCC 51739 | 8 | 8 | UPEC 3042 | 16 | 16 | ECOR 9 | 4 | 4 |
| CCARM 1A746 | 4 | 4 | UPEC 3051 | 16 | 16 | ECOR 15 | 32 | 32 |
| CCARM 1G490 | 16 | 16 | UPEC 3150 | 8 | 8 | ECOR 35 | 16 | 16 |
| F485 | 4 | 4 | UPEC 3151 | 64 | 64 | ECOR 36 | >64 | >64 |
| F524 | 8 | 8 | UPEC 3163 | 16 | 16 | ECOR 43 | 16 | 16 |
| F576 | 4 | 4 | UPEC 3164 | 32 | 32 | ECOR 45 | 4 | 4 |
| F716 | >64 | >64 | UPEC 3168 | 8 | 8 | ECOR 52 | 64 | >64 |
| F852 | 8 | 16 | UPEC 3181 | 8 | 8 | ECOR 69 | >64 | >64 |
| FORC81 | 8 | 8 | | | | | | |

The target strain included type strains, drug-resistant strains (CCRM and FORC81), clinically isolated strains (F), uropathogenic strains (UPEC) and adherent invasive strains (ECOR). The MIC was shown to be 4-64 μg/ml in most of the strains (LNT113 of 1 mM was 23.2 mg/ml and LNT113 of 1 mg/ml was 0.0431 mM). The MIC for endolysin EC340 or mtEC340 was >128 mg/ml (Table 3).

In addition, the minimal bactericidal concentration (MBC) was same as MIC, suggesting that the action mode is sterilization. The MIC of LNT113 was confirmed for various gram-negative bacterium such as *A. baumannii, P. aeruginosa*, and *K. pneumoniae* (Table 4).

TABLE 3

MIC of endolysin combined with colistin in *E. coli* strain (μg/ml)

| ATOCB739 | | UPEC3150 | | FORC81 | | ATCC8738 | | ATCC8738 | |
|---|---|---|---|---|---|---|---|---|---|
| LNT113 | Colistin | LNT113 | Colistin | LNT113 | Colistin | EC340 | Colistin | mtEC340 | Colistin |
| 8 | 0 | 8 | 0 | 8 | 0 | >128 | 0 | >128 | 0 |
| 4 | 0.0625 | 4 | 0.0625 | 4 | 1 | 32 | 0.0625 | 32 | 0.125 |
| 2 | 0.5 | 2 | 0.5 | 2 | 4 | 16 | 0.125 | 16 | 0.125 |
| 1 | 1 | 1 | 2 | <0.25 | 8 | <2 | 0.25 | <2 | 0.25 |
| 0 | 2 | 0 | 4 | 0 | 16 | 0 | 2 | 0 | 2 |

TABLE 4

MIC of LNT113 against various gram-negative bacterium (μg/ml)

| *A. baumannii* | | *P. aeruginosa* | | *K. pneumoniae* | | *K. acrogenes* | |
|---|---|---|---|---|---|---|---|
| Strains | MIC | Strains | MIC | Strains | MIC | Strains | MIC |
| ATCC | 8 | PA01 | 4 | ATCC 700603 | 16 | CCARM 16006 | 16 |
| ATCC | 16 | ATCC 15522 | 8 | KCTO 2208 | 8 | CCARM 16008 | 8 |
| CCARM | 8 | F102 | 16 | CCARK 10143 | 4 | CCARM 16010 | 8 |
| F4 | 4 | F125 | 4 | P1O4 | 16 | F276 | |
| F65 | 8 | F141 | 16 | Fil8 | 16 | *E. cloacae* | |
| F66 | 8 | F171 | 32 | F144 | 16 | ATCC 13047 | 16 |
| F67 | 8 | F388 | 32 | | | CCARM 0252 | 4 |
| | | | | | | CCARM 16003 | 8 |

The strain includes type strains, clinically isolated strains and drug-resistant strains. The MIC of the antibiotic for the drug-resistant strain used was described in Table 1 above. The MIC ranged from 4-32 μg/ml. In case of *Salmonella typhimurium* and *Salmonella enteritidis*, the MIC was >64 μg/ml.

Example 5. Cytotoxicity and Hemolytic Activity of LNT113

In order to confirm the cytotoxicity of LNT113, WST-1 analysis was performed for human liver cancer cell line Huh7 (See Preparation example 10). When LNT113 was treated by 250 or 125 μg/ml for 48 hours, reduction of the cell survival rate was not observed (FIG. 7*a*).

In order to measure the hemolytic activity, LNT113 was added to red blood cells at a concentration of 2-128 μg/ml. The hemolytic activity of LNT113 was not observed (FIG. 7*b*).

Example 6. Synergistic Effect of LNT113 and Various Antibiotics

In order to confirm the effect of binding LNT with various antibiotics, checkerboard assay was performed (See Preparation example 12) At first, the FICI (fractional inhibitory concentration index) was measured to observe the combination effect of LNT113 and colistin in the *E. coli* strain. The checkerboard analysis result represented by isobologram including FIC floating of LNT113 and colistin was shown in FIG. 8. The sum (FICI) of two values was 0.25 when colistin and LNT113 were treated in *E. coli* ATCC 8739. This shows the synergistic effect of two agents. In case of the UPEC 3150 strain, the FICI was 0.375 and the synergistic effect was showed. In case of *E. coli* FORC81, the FICI was 0.5 and another synergistic effect was shown. It is noteworthy that the MIC of colistin in the colistin-resistant *E. coli* FORC81 decreased from 16 mg/ml to 1 mg/ml when treated in combination with LNT113 of 4 mg/ml (Table 3).

The synergistic effect between the LNT113 and 8 different antibiotics was confirmed for 5 different *E. coli* strains by determining the FICI (Table 5).

TABLE 5

Fractional inhibitory concentration index (FICI) of LNT113 using various antibiotics

| | *E. coli* strains | | | | |
|---|---|---|---|---|---|
| Antibiotics | ATCC 8739 | ATCC 51739 | UPEC 3150 | CCARM 1A746 | FORC81 |
| Colistin | 0.25 | 0.5 | 0.38 | 0.63 | 0.5 |
| Ceftazidime | 2 | 2 | 1 | 2 | 1 |
| Meropenem | 0.63 | 0.75 | 1 | 1 | 2 |
| Kanamycin | 2 | 1 | 1 | n.d.* | 1 |
| Tigecycline | 2 | 0.63 | 0.63 | 2 | 2 |
| Chloramphenicol | 1 | 0.75 | 0.75 | n.d.* | 2 |
| Azithromycin | 1 | 0.75 | 0.75 | 1 | 2 |
| Ciprofloxacin | 0.75 | 0.75 | 0.75 | 1 | 0.56 |

(*not determined
FICI: ≤0.5, synergy; >0.5-≤1.0, additive; >1.0 to ≤2, indifference; >2.0, antagonism)

While the synergistic effect with colistin was observed in 4 strains among 5 strains, an additive or indifferent effect was observed in all the other combinations.

In addition, it was observed that the MIC of colistin was significantly reduced, when there was the endolysin EC340 or mtEC340 having the MIC of >128 mg/ml (Table 3).

From the above description, those skilled in the rat to which the present application pertains will be able to understand that the present application may be embodied in other specific forms without changing the technical spirit or essential characteristics thereof. In this regard, it should be understood that the examples described above are illustrative and not restrictive in all respects. The scope of the present application should be construed as including all changed or modified forms derived from the meaning and scope of the claims to be described later and equivalent concepts thereof rather than the detailed description.

```
                            SEQUENCE LISTING

Sequence total quantity: 28
SEQ ID NO: 1              moltype = DNA   length = 42751
FEATURE                   Location/Qualifiers
misc_feature              1..42751
                          note = synthetic_Bacteriophage EC340-M-11-12 whole genome
source                    1..42751
                          mol_type = other DNA
                          organism = synthetic construct
SEQUENCE: 1
gttctcgtcg gtagatgtgt cggtgttcga tggctccacg ccgttgcgtt gcgatactct   60
caccatcacc aacgacaacg gagcttccgc gcagttcgaa ctcggtaaca gtagcgtggc  120
gttcgtcgaa cgtggacgcg cagctaacac attctctatc tctggcaagc tgtacgacat  180
ggcgatgatt cagaagttta tcaacgagca gcaggtagga attaactcta ttctggcagg  240
ggtaaacggg gctatgtctt tcagtttgaa acgtgcagag cttacggcgg ttacacctga  300
gattggtggg cctgagtcaa tcactcagtc cattgaaggc caggctaccg gcaatcagta  360
ccagtcgtct atcgtaattc aacgtatcac ctacgcataa aactaaggcc cctttcgggg  420
ccttttttctt acaaacctaa ttttaaagca atgtctataa cgttcgattt aacgtcaccc  480
ggtatgatgt aggtgtcgta atcttttaca ccactaacat cgtacagata gccacggcta  540
tcgcagatga acgtatagcc gtcacgatgg aggcggacga ttcgcacgtc atgcccgcg   600
gcgacgatag gggcaacttc actggcgaat ccaccatcgg acactacaaa aacttcgtcg  660
ccgtcaggca agttttcagc aagatactta ccgaaataat catcgccgaa taccggttta  720
atgaattgct cagaaatggc aatcattaac cggcggcggg acaacccatt aagaaaaccc  780
tcgggttttt ctttccgcgc ccggtcgtcg tagccgtcga gaaattcgtg gtaagcatcc  840
tggcctaacg ctgccaaagc aatattgaac attggattct tgaaactggt agttcctttc  900
gcaaagccca tttctaccag cgccatagca agcgtgtctt tcccgcaacc cgcagggcca  960
ttaagaataa ttaccttagc cattatttat cgctccagtg tggttttaag tgtgtagagt 1020
tcccgttaca gtcgtattcg gtaactgcgt gtgcggttat gccgaggtca cggaaatgct 1080
ttattaccgc tggggagtcg tcgaacgcac acaagattc ttccagtccg aaagcacgca 1140
acacctcttc tttaattacg atgtcttttc tgttgtcgtg tttgctgcgc atgattagcg 1200
tgtcaaacct aacgttattc tctcgtaacc attcgcgagt ctcctcctca gcgtcatcac 1260
ttcgcccggt aaggataatt atagtaagtc cggaatgcca cagtacgcta cacaaatgga 1320
tattgtcgta tatcggagcg tcatctttgc aggccatgtt aaatggcttc cacgcccacg 1380
tttctccgta gttatctttt ggtaacaggt gtaagcgatg ggtaccgtcg gccaatgtcc 1440
cgtctaaatc gaaaattaca atatctttca tcccagcatc tccggtgaaa tagttaaacg 1500
tgcgacctcg ccatattcgg cgctataagt aattacattt gcactgcggc ccgacatcca 1560
tccgccgcga gaggcgtagg cgtctttagc cgctaaggtg cggtgttgct caacaatcat 1620
gttacggctt tctacaatct tctggtggtg cagatggcct acgtgggcgt agctgtaaac 1680
actctgccg aacgctttac ggaacttggc aatcataacc ggttcgatag cgtcgaatcg 1740
tgctttatgc ccgtgatgga agaacagcgt cgttttgccg tgttgcacca tcttgtaaac 1800
atccggcgac gtatcaacaa tcactcggct gtcgtttgag tataaaaccg tgaacatttc 1860
ggcaagccat acggagccaa cagggtcgtg gttaccttga acgattaaaa gttttactgt 1920
gtgatgctta accagcgcca tatcaacaac acggcggacc atacgaatca tgtaacgtac 1980
cagtttctga tagcgagtat ccgcatctaa tacatggcgc gactcggggg taacggcatc 2040
aagactatcg aagtgtgcga agtccccaag caggttaata actcctgttc ctgcatccgg 2100
tgctttctga aacgccgcgt cgaaccaccg agagaacagg tcttctgcaa tcttcatgtc 2160
ccagtcgtcg ccgctctcat cggcccatgc cagcataccg agatggaaat cagatacagt 2220
gtaaagattg agtagcttgt cgtcacgttt ggcgcgcgcc gctttaacag gcgcaacggg 2280
cgtaatctct gacttcatgc cctctattac ggctttcatc aattcaacct gacgttcggc 2340
gtcggtgtct gtcttaaccc actgcaactt agtgttaccg aactcgtcca ccagagacga 2400
cgtgccttta atcttgtagc cgtctggtac aaggtggctt acgtcccgcc cgtggcctac 2460
gcctttctta gccagcttcg ctttacggat tcggataacg cggtctgaga ttccgtattt 2520
acgggcgata tcgatattct tcatcccggc gttcaattct tcctgtaatt gctcgtcggt 2580
tatttttcttc tgggccatgc ttacttcctc gtgtttagga tttgtcttat agtagcctac 2640
ttctctttca cgttcgagtt gcaagcccag attaaaatga ataccacgg caacagaatc 2700
cacccgagaa ataagttagc catgaatatc gccagctttg ctttatggtt acgcatatgt 2760
gccaccaaaa acgggataaa ataaacggct acaaaaataa ttaagaagaa catagtgata 2820
ccggtcataa cataactcct gatttgagat aacatcgttg gtgtaagtga atagtacgct 2880
attatattgg ggtgtgcaag tagtgtgcta gaataatttt gcgcctagtg tcgcacacga 2940
aaagcgggtg gttcccgtct ggcgcatttc ctttaaccag taacctctta accaaaggat 3000
taaagaatga aactttctga tttttattac gaagcggaag ccgaaaaggg cgcacgtatg 3060
ccgataccgc taaagacgg tactgattcc ggggaatggc ttaatgttgt ttctcctgag 3120
gcggacgttg ccgttaaggc tatgcgcgcg ttcacccttg cataccgggc agtattaggg 3180
aaattaaaac cgcttcgtga taagtgcgaa gagatgaaag atttctctga atacaacctg 3240
aagatggaag acgcggcgac ggaccttaac cgtcagttag cgattgaatt ggttaacggg 3300
```

```
tggagccttg acgacgaatt caataaagag aatctgaaca cactcctgac gcaatataaa 3360
cgactcgcgg aacttgttgt tgtgtttcat aacgaacaac tgcaccagct acaggaaaag 3420
tagacgcgtt gctccagttc gcccgttgga acttcataac ccgccacaaa cggcgggaat 3480
ttgacagtat cgccgatggg cataaagccg cgctaattgc tatggggggtt atgcaagacg 3540
cgccggatgc aacgcaggcc gctgggccgg aatgcccccc tgagctacta accacatttg 3600
agaagtacag ggaaattaaa ttcacccgcc gagtggacga cgacggcatc aagatgtacc 3660
cgcgcgagca attacgatgg tcagatttag tggcgtacag caccgtttca ggccagaata 3720
tagggatgtt cgaatccgac atcatcatga gcttagacgc tattttcgag ggtagaaacg 3780
atggctgatg tagctagttt agtagtaaaa gtaacagage aaggcgcgaa agccacatca 3840
gaccgtcttg acaacctttc aaagtccgca aaagtaggag gggccgccgt agcaggcctt 3900
gcttctatcg tagcggctac cgcgtataaa gctgcccaag aactggttga ctcacagcgg 3960
caactggaca agatgtccgc cagtttgaag accttaacag gaagtaccca aggtgctaaa 4020
caggcgctaa gtatcctgca agattttgcc cgcgatatccc catacggact ggagcaggcg 4080
gtggaaggct tccgtaagct ggtggccctt ggccttaccc catccgagga ggcgttgcgg 4140
tcctacggca ataccgcatc ggctatgggc aaggacctta atcagatgat tgaggcggta 4200
gccgacgcca gtacgtttga gttcgaacgc ctaaaagaat tcggcatcaa agccaagcag 4260
aacaaaaacg acgtagagtt tacattccag gggacaacaa ccgtagttaa gaaaagcgct 4320
gccgatatttg agcagtattt acttaatatt ggtaacgtaa ttgccggt tgccatggcg 4380
gaccaggcca acacccttaa tggtgctatc gcgagcgcca gtgactcatg gtcgcagcta 4440
aaaatgacgc ttgccaccag tcttgatgtt ggcgcacttg cggaacctat caggtatatc 4500
gatgacttga tccaggaatt aaacgcgtct gttgcttccg gtgaattagc cgctgaaatg 4560
cagatgtggg gcgacatagc gtcggaagta ggaagcgcta tcgagatgtc attcgacgct 4620
gcgtttggct ttgttggtga tgccatcaac gggcttaatg aactgtggga tttcagcagc 4680
aagagtatta ccgatagcgg agaacaaacg gccaccacca tcgctgaatc cgccgccgat 4740
gctcttgact tcatcgcgga agagttcacc gcgatggaga gattctttga agatatggtt 4800
aaaggtgctc aggacgctg ccgtcttgta cgcgccgctt ttaccccgg ggaatcagta 4860
gacgtagcta aaaatatcaa cttccagctt ggcatggctt tggataccca gcgcgatgtc 4920
gccgacgtta cgcgtaaaag tttccgcgaa caggtagaag ctcaacagga tattgtagcg 4980
ttaaaacgcg cggcgtatga catcgataag gagtccgcaa aagctgaggg gttaaacaaa 5040
tttaaggtaa ccggaaccgg cggcggttct gacgatgacg ggtcagccgc aaaagccgct 5100
aagaaagcag cggacgcgtt cgagcgccaa aaaaggcgg cggaagactt ctactatcag 5160
tcaatccatc ttaatgatga cgtatttcag aaaatagaag ctaaccagga agagcaactg 5220
tctaagttgc aggatttttta tagcaataag cttcttagcg accaacagta cgaaaacgcc 5280
aagacgcaga ttatgctctc tgccgaacag gcccgccagg aagaactgga caagaaaagg 5340
aaagaagccc aggagaagca gcagaaaggt gatgatttca tggctcagat tatgggccag 5400
aacgccaccg agcttgagct tctgatatt caggaacagc agaaactggc ggtagccgat 5460
aagtaccggg aacaaggtct gattagcgag aagcagtatc aggccgcgct taacgccatc 5520
aacgagcagt acgcaaccaa gcgtgccgac gcaacggcaa cagcttcgg taacatggcc 5580
tcaaacatcg ggtctgcgtt gggcgaggct tctggccgcg ataaagcatt cgctatcgta 5640
caggctacta tagccacgta caccgcagct attgaggcat acaagtcaac ggcggctatc 5700
cctgtagtcg gtccgttcct ggccccagta gccgctgctg ctgctgttgg ggccggtatg 5760
gcgcaggttt ccgctatcag gtccgcgcgt gaacagggcg gtcagttatc agcaggacag 5820
gcttcaacca tcgccgaacg cggtaaacca gaagttatca tgcccgctgg tgcgtcacgt 5880
gtacgcaccg cacagcagat gaaagaaatt atggggcaaa acgggtcttc ttccggaccg 5940
tctaatgtta ctatcgtaaa caacacgagt tctcaaatcg gcaacgtatc cactgagcaa 6000
gatgatgaag gccgtttgcg tatcatcatc gaggagcaag tggctgcctc tttgcagaac 6060
agtaacagta agattagcaa ggcccgcaag gccacaagaa atgcgccggg gtttaaataa 6120
tgagcgactt atatttccca cgtagccta agccggtggt atcgaaaggc tactcaatga 6180
ccagacgcaa caacgtctgg agtgtagatt tagccggtgg cggagtgcgt caaggccgtg 6240
acacgtatta tgatgtgttc ccaataagcg taaccctgat tacatccgca atggggcggc 6300
aggcgtttct gtcgttcctc gagaaagtcg atggtgggcg gtcaagtttc tggatgcgac 6360
acgacttcgg catgggtatt gaggattatc aagtcaccat tacatccacc gtcgccgagt 6420
ccactgaaga cgggattaac tggacaatta cttttcacgg caaccgctgag aaatcaccgt 6480
tccaggacct cgagaaccag tgccttgtta acaatctgcc ggatttgtat ggttgttatg 6540
gtgacgggct ggggtgtatc cttaaagcct acggaaccgc acaatcaacg tttccacgaa 6600
tttgggaacc gatgcaatga gccaggaatc tgtagaagcc gcctatcgcc gtaagctggc 6660
ctcaaatccc gacggcgaga tggattacat cacattgcaa atcagccacc cgttgttgtc 6720
aaagacgtac tatcttgtgc gcgggttaca ggaactcacg gcaacactgg agacaggcga 6780
aattatcacg ttcgagccaa ccccgatgga ggcgtcgggg gcggctaaca acagtgtatt 6840
ggaccagacg actacgttta ctttaccgga tattctcaat caacttgacg atgagatgga 6900
taaaatccct atgagtaaca ccgagttgcc gaagttcgtc ttccgtcgtt acgtcagcac 6960
agacctgtct tatccggctg acggtcctgt catgtatgag ttgcaggcca tcaaccagga 7020
gaagggcgag ttctccgcgg atgttggtac acctatgctg aaccagcgaa gcactggtat 7080
actgatgaca cctaaagaga taccgttatt acgcgcgtcg ttgaccacat gaatattaac 7140
gactacacgg gcataccta cgactttcgc aagcgcaatt gctggcatca cgtgcgcatt 7200
gtccgcgcgt atgccgggtt agaaacccct cgcgttgacg ttacaagccc atcggcaatt 7260
aacgaagcgt ttgacgaagg ccaccgtgac acgaaggggc ttacaaaaat tgataagcct 7320
gaaaacttct gcgcggtgct tatgggttat cgtcgcgggg gtcgtatcgt gtggcacgct 7380
ggagtttact tcgacgggat ggtgagtcat tgcgagcttg catcccgtca ggtacggctt 7440
gacaggctgg tggacctcag agacacgtac acggagattg aattttggcg ataatcctgc 7500
actacacgcg aaacgctgaa ggcgctttcg accgtacaaa acacgtcggg atgccgatgg 7560
agtttgtcgt taaccgtatt ccctacgcg tgcctgtgcg cgtctatctc ggtgagattg 7620
gcgatgatac agatgtaaca gacgacttca atgcgctcaa agacgaggac gccgtgtacc 7680
acattatcga gggtgcaggc ggtgatatcg gcacgctat cggtagtgta ttcagttca 7740
tccttaagcc aattgccaaa ttgttcgggc taaacacaga agctaacgct aattattccg 7800
ctaccaacaa tcaggctacg tcgcctaaca acagtcttac tgaccgctcg aacaagccac 7860
gtccttatga acgttcttat gacatctgcg ggacagtgca gactataccc aatgacctga 7920
tgcagacgta taaggtgttt aacgccacgg gggcgcttat tgaatatgcg tactatgacg 7980
ccggtcgagg gtatctgcat attgaggaag acggtgtaac tgaggcagat acccgaatca 8040
```

```
gcgagataac tggctcgtcg gtgacggtgt attctcctta cacttcgccg aataacacca    8100
gcacaccaca attgcatatc ggcgacccta tagaccagaa attgtacgtt acatttaaaa    8160
acgccgatgt cgatggcgct gttcttcccg cccctaatga tatcgctata gacgtgcagg    8220
actacactgt ccagcggcag ggaacaaccg gcgttgtagt aggcgatgac gctggtttcg    8280
atgagttttt ggcggtcggg gacctggcat acttcgataa cgtatatgca gatacaaccc    8340
cagggtcttt gggtaatgag gttaacctgg acgggaggta cacggttctt tctgttagtg    8400
aaacgaccct tattgtggac gtcagtacaa atcaatcaat atggaaccag ctaggaacat    8460
ctgtatggtt tataggtgaa gagggcaacc atccttatagg cccggcggat acttacgcgg    8520
cttccctctc tgaatgggcg tacatcaccc gcggaaccgt cgaccgtgtt gtagccaatg    8580
tggctgccag caacggcatg tacaaataca acggcgacta taaccgcgct tcagtgacag    8640
tcgaactgca ataccagatg gtagatgaat tgaaacagcc tgtaggtgac atatttaccg    8700
tacgaggaac cgtaacaggc cggaacacgg attacacagg gattactctt tacggaagtt    8760
taccaactgc ttccagattc cgcgcccgta tgcgtcgtgt ttcggacacc gataaagatt    8820
ttgaaggtac tgttagcgac gaggttactt tcactaatct gtatgggcag tcgctggaca    8880
caaccccccca ctacggcaac cgtactaccg tacactgcgc ccgtaaacaa accccacgtg    8940
cagccgaggt gtccgaaccg gaactgcgca tgattgcaac cgagatgtgc tacaaatact    9000
taggtaacgg cgtattcgat acggtaatga caccgaacac tcaggccgtg cagtcgctaa    9060
tcaggctggc gcgtgaccct gtggtgggta atctggaact gacaacggca aatatgacaa    9120
agttacttgc cgtgcaggaa gaaattgagt cgtattttga cagtgaatta gccgggcagt    9180
tctgctacac attcgacgac tacgacacaa ccatgcaaga catcgttcag accatcgcgg    9240
aagccgtgtt ttgtacggca taccgtaaag gtgctgtatat tatgctgcga ttcgaccgtc    9300
ctgttgcggg gcctgagatg gttttcaccc accgcagcaa aacgaccggt acggagaaat    9360
ggacgcgcac gttcaacgat tcgacaacct acgatagcct gtcgttctcg tacattgacc    9420
cggatacaaa cgtacaggag acgatttata tcccggaaga actcggcgcg aacaccgagg    9480
agtacgaatc gaagggtgta cgtaactatc agcaagcgta ctggctggcg tggcgtcgct    9540
accagcgcaa cacgttaagt aaagttgtcg tagagttcga agtaccggaa gaaggcgctc    9600
tcgctactcc cggcggcgta atcagtgtgg ttaaaggctc gcgtatccgcg ccgcaggatg    9660
gttatgttgt tgccgtcaat ggccttacgc tgacgctgtc tcagcctgtt acgtttactc    9720
ctggtgatga ccattccatc attcttaaga agcgcgacgg ctctgtgcag agtattttctg    9780
ttatcaaagg aagccacgac cgcgaagtga ttatgctctc cgcgccggag gaggcaatct    9840
acacggggaa tagtgcgcta aaaactgagt tttcattcgg caacgaagca aggcataatg    9900
ctcagaagat agttgtttct tcaatcgacc ccggcgacga ccgcacgtc aagattacgg    9960
gctacaacta tgatgacgga ttctatataa acgacgcgt cgcgcatac ggcagcggtt   10020
tctccgacgg attcagcaat ggttttaatt aaagaggact ctatatgtca agccgatgcg   10080
gtgacgtttt aagcctggcg gatttacaaa ccgccaagaa acaccccaatt tttgaagcgt   10140
aggttatcac cggtaaatcc ggcggggttg ctggtggcgc cgatattgat tacgcgacca   10200
accctgttac cgggcagacc cagaagacgc tccctgccgt gttgcgtgac gctggttttt   10260
ctcctgtatc gtgggacttt tccaccggcg gtacgttaac cgctaatgac cgcgacaaag   10320
tggtgtatga ccctgtaagc aagacgtggt actcgtatac cgggactctg ccggttgttg   10380
tccccgcatc gtttaacccg gttggtaacg ctaactggaa gccgcagact gaccggatt   10440
tgcgcaatga tttatccagc acagacatg cgacattagg tgatgccatg gtcggcgtcc   10500
gacaaccatt taccgacgct gtcggcagga cgcaacacga taaaaataga gaagtagttt   10560
ccgttctgga cttctatttta ggtactgacc tgattacac aaacgcccttt aaccgagcgc   10620
ttacagctag taacgggggtg cttgtaccgc aaggggagta tagtacgtcg ctactctccc   10680
accccgacatg ctctctattc ggaacagggg gtggggttttt aaaacaatca aacgattctg   10740
gaaaccactt aatctttgat aaacctgcag gagggctact tagcaccctg agtattgtag   10800
gaaataaggc aacggactcc acacagggtc agcaggtttc cttcgccggt gggcaggacg   10860
ttactattaa aggtattgat tttaaaaatg caaagggaac tggattaagt ttaatagcat   10920
accctagcga tgggggtccg tctggataca ttgtaagcgg catacggggc gactactccg   10980
ggtatgctac aaataaaaaa gcggggtgcg tgctgtttga ttccgcaagt aatactaaa   11040
tcaacgatgt tatcgcccga aactacccccc aattcggggc ggttgagttg aaaacagatg   11100
ctaaatgtaa tgttgttagt ggcgtcattg gcaaagctg tcagcacgtt gtttataatg   11160
gcaccgagac gaccaatgcc cctagcagta atattatcag taatgttgtt gctaataacg   11220
ctaagtatgc cgctgtggtc accggcaagg gttcaggtaa tctggtgaca aatgttgtag   11280
ctgattactc ctcctccgag gccacgcaag cacacgcgt tacattacaa ggcaactata   11340
atgccgctga taatattcta atggttgggt gcagcggaac taatagttta gggcaaacgc   11400
aaaccgcgac ttctattagg tttttagcg gagctagtaa taactacgca tcggttttcc   11460
ctatgtatag tgcttccggg gttgttacac tagcgacagg gactaccccgt aactttgtgg   11520
aagtaaagca ccctggaccc aagaacagtc ttcttagttc actatctact ataaccggtg   11580
tctctagcat tgatggtact accgccagta acgtgtgaca cgccccgct ataggacaat   11640
acataggtc catgtccggt aagtttgagt ggttcactaa gtatatagat acttctgcat   11700
tgccttttgt gacagctgat aaattcagac taatttccga tggggccaca tctttggcta   11760
ttggtggagg tacgacctct cagataaaat tactcacatc tgatagtact tctcgaacta   11820
tttctctggt tgatggtgat ttacgcttag cctctgacgc atcggcgtat attcaaatag   11880
ccccgacggc tattcacca tccagcgcaa acaccgacgc tatcgggtcg gcaagtcgcg   11940
cttttgtccgg cggattcact caaacagcgt ttacggttac gtctgacgag agagccaaga   12000
cactacccct ggaattaact gacgctatgt tagacgcttg ggctgaagtt aattttagttc   12060
aatataagta cctggatagg gttgcagaga aggggaggga tgcagctagg tggcactttg   12120
gagtagtagc ccaacgagca attgaggcgt ttaccccgca cgggttggac gctgactaagt   12180
acggtttcct gtgctacgat aagtgggaag cgtctccgga aattattgat gaggaatctg   12240
gggaagtatt aacaaaagct acggcggcgg gggagcgta tggtattcgt tatgatgagg   12300
tattgatatt agaggctgcg ttacagcgac gtaaagcagc tcagttagag aaaaggatta   12360
tagcgcttga gacattagtg gctaccctga caaacagtta aataaacaag gccccaaacg   12420
gggccttttc tctactcttc tgataacttc tccagtacaa acgccagtg cgcattagcg   12480
gcgtctcttt gctgacgtag ccgcagaacc tcttcttcga gttccttgat acgttttttgc   12540
aatgctggaa tcgggctat gatgttcatc tggtaaattt cctcgcaaga tacgttattt   12600
cttcttcaca aagttcatca aggtcgttag atacaaatcc tctggtgaat gttttgctga   12660
actttaatcc agctttatca ttgtcgccag cgcacaccca gtcatacggc aaagtgtaca   12720
tttgctgccg taggtctgtt gatatatttg accccagtgc gcttacagca ttgaacccgc   12780
```

```
aattcatcaa ggctacggct ttgaatatgc tttcggtaac aaataccacc ccgctttccg   12840
gcaaatactc aagcccccat aaacacggcc ttgttgttct ggtaaagtac cgcgcgtctt   12900
tagggttttt acagttcttt tcggcatgtg gtttgtaatg ctggtatccg cgaagcctac   12960
cgtcaaaccc ccacaggtaa aacgtagcta ctccaggggc taagactacc tggagacggt   13020
cagcgtcaaa cccacgcgcc aacagatgag ctttaagtag aaactcttcg aaatccatca   13080
tttcttacct cgtctcttca tgtaattaag caactcttcc tgtaccgatt tcttctcgtc   13140
ggtacgcgcg gcgacaacct cgtccagagt gtctttagca actatgtgat aaaggaaacac  13200
cgggcgctcg tgacccgcct gtttctggcg gactgggcct atgcgctcaa caacctgcaa   13260
atagtgctca aggttccagc cttgcgagat gaacgccaga tgatgacccc cgtcctgtaa   13320
attcaaacca tgcccggctg acgcaggatg cacgcataaa atctcgattt ccccacggtt   13380
ccacgcttcc atctgcttgt tccccctagc gcctttggcg aacgcctgtg cctgtgggaa   13440
tcgcttaagg atacgctcca gttcgtgttt aaactgatag gctaccagca acggcgcacc   13500
ctgcaactcc tcaacaatcg actcgagcgc atccagtttc gtgtcgtgca ctttctccca   13560
gtctttggtc gcttcgccat ccggccctga cacatacacg gcaccagatg caatctgcaa   13620
gcactttgag gtcttcgccg cagcgttagc cgcttcaact tccccgctct ccagttctgc   13680
gaataacttc tcctccatat ctatgtacgc ctgacgcgct ttcttcggca ggtctatttc   13740
caccggtacg ataacaggcg cttcacaacc aaaccactcg gcagggtcta tggtcaggct   13800
gatgtctttc atcttctgat gaatctcatt atccgcaccc ggtcgtgcat gatactgcgg   13860
ggccatagcc gatttacctt tctgtaccga gttaaaccag cggtcggtga atgctgtgta   13920
cgaagagccg aggcgctcgc cagcgtcgat aaaccagttc tgaccccaca agtctttgag   13980
gccgtttggt gacggtgtgc ctgtcaggtt gatgaaacgc ttaaccttte cgaacgcaac   14040
cttgctgagc gccttttgccc gcttgctacc acccgaaccg ctgcggaacg atttaagctt   14100
cgtgctttca tcggcaacga taaccgtaaa aggccagtcg tctttgccgt agtagtcaat   14160
tagccactcg ataacttcgt agttagtgca caccacgtta gcatctgact ccagcgctgc   14220
gatgcggcgc ttctccgaac cagttgcatc tacgacacgg agacaaggga attgccattt   14280
ctcttgttca gcgggccacg taccggatgc aacacgacgg ggggcgagga ttaacacgga   14340
gtcatcttct gtaagctgcc cgttgcgaaa caggcgatta agcacccaca tagttgagga   14400
ggttttgccc cctcccatgc cgcaccagat attacagcgc ggatgctgta gcatgaacga   14460
agtcatgagc ttctgatatt cgcgcccttg aaacttactc attttgccac cagaactaac   14520
tctttacgcc cgaacgctgt aacattgcct gttacatctt cgataaccag tttaccgttc   14580
gactcgacga acactgtatc aacggcaaca ggacgacgtg ttttaacgtt gaaaatcatg   14640
tcacccggta cgatgtcacg tgctggttta cggtcatatt cgtatttcat ctatcaattc   14700
cttatattgt tggtgtaggg ctaactataa tagttcgcta ttaggtcgtc aacctgtttg   14760
aacgaccega cgacaaaaac atttgcacca cgcttacgca tccgctcgtg ctctcgtaac   14820
tggtgcgggt caggcttcgt gctttcgtct ttcttcacct cgacgaacca gacgatgccc   14880
ccagggagaa ttaccagcag gtcgggagcg ccggaacgcc cctcataaga cagtttacgg   14940
acgaggcccc caagggcctc gaatcgctct tttgcgtatt tctgtatttt tccttccggg   15000
gtcatgagcg cagaacccag gttataaatg ccccgcccag aatggcaacg ccaacaaact   15060
taagaaacag gccgtaacag aacatcgcag ctattccgac aactagtaac agcgcgaaca   15120
gggttactat tgtccaaaat acaaacattg tcataataca cacccctcac gtttcgtatg   15180
ctcaatcccg cagcgcggac agattcggca gtcttcttcg tataaccagt aaatttcat   15240
tccagcaccc acaaataaat tgcgatgaac ataacctaata cggcgaccat catgccgtat   15300
tggccctcgt gacagtagac accggccgcg aatcccgcca atcagttta   15360
cttggcattc taacctccgt gattctcatg aaagccgtag cgaacaatcg cagatttccg   15420
ggcacaagcc gcgtcaaata tattgtcatg gtggcccagg aatataagtt taccgtcaac   15480
gaatatccct gctttccatt tatccgcccg tgcgttccag tgcacaccag tgaggcctga   15540
cttgttatct tttctgcgag atgcgtttcg gttattatca atacggggta cttttccgaag  15600
gttgcatgca cgattatcat ccaggatgtg atttatatgg tctacctcat catcaggccc   15660
taaacggtca ttgttataca tctcccacgc gatgcgatta gccctgtaac taacccctct   15720
gacgacgata cagatgtagc ccctcttact tgggctaccg gcttcgtctc cggcgtttat   15780
actgtgtctc ggggaaatact tccatcgtat ctttcccgtg tcaggttcgt agtagaaatg   15840
gtcatgccaa ttaattaaat ctctcataaa tcgcccctca tcatttagca tatctgtaca   15900
tttcgctacc ttccgctaca agagggaagc cttctgccca ctcaggcaac gcgcacatca   15960
atcgttccga ttcagccaca ctgtattccg gcgtatctgg agtttcgcac accagttcat   16020
cgtgtaccga aagcacgatg ggatacccgc catcctcaac cttaatcatc gcatatgcga   16080
gtaaatcccg gcacagcgcc tgaacaatgt tttcgcagge tttgccgccg tgtgtgtaca   16140
gggtagtcca ttggcgggtt aactggtttt caccttgata cttgattcgc acattcgtgt   16200
tcacccgtcc gtcttcatct gtttcctttg tcacactaac cccgattccc ggatacgaga   16260
ggatacggcc agacggcaaac tccatacaca accaccaacc cggaaccttc ctaccggatg   16320
aatcaaattc tacagtacgc catatgcgga tagcccttc ccatttctg cgcaagtgtg    16380
ccccccgccca aaattcacga ccaggattac gcacagcggc taaaattcca tctttaaggt   16440
cgcgccagaa cgctactgtt tccgggtgtg actcgcgcca catacgcttg atagcgtcac   16500
aagtacgcca tacttttta tcaagaatat atgatggcct gtcgtccttt tcacctggat   16560
gcggggggcg cttggcttcc tggatgcgcg cccattcata tcctctcgcg gtggctgacc   16620
agatgtggtc ggggaatgta ccgtccattg tttttgccat ctcaataagg tcaagaccta   16680
agttttggc gaacgtaacg aacgctccga cgccgccttc atagccgagg ccaagctcgc   16740
aagccttgcc tatctgtctg atttccttga gttttttctt aatgtcatcg gggtccatgc   16800
cgaacatctt acccgcggtt acgcagtaaa tatccagtcc ggcgcggaac gtatcgagcg   16860
cggtttcttc tccggccagc cacgctaaac cacggccttc aacgttagag taatcggcaa   16920
cgacaaactt ataccccgct tccgggataa tgcagctacg aaccgtagat gctgttagct   16980
tggctacatc aaaacggcga tgcgctcgac ccttaagtaa cgctgaaatg cctttatcca   17040
gttcatcatc gtgatagtaa cctgcgccca ggttctgcgg ctggaatcct ttaccgccc    17100
atcgcagagt acgtttcgct ccgccgtact gcaagcaacc acgacggcgg tcgtcagaag   17160
aaccgccaa cagcaacggg ttatatttcg ttgacgcggt gcagcagcc cctaggcgca    17220
tttcgataat cgtgcgagcg tcgtccggta aatcatcatc tgccaacagg tcgttaagcc   17280
tcgacttctg tgcattgtgt atgtggtgcg cgggcgcaag ttcacgcaga atcggaagga   17340
agtctttacc ggtaagcgag ccgccgtatt tacgttgagc ttcttcctgt aactgtgcct   17400
tgtgcttctc tacggcttca atcgcggctt ccgccagtgc gacgtcaacc ttaaatccgc   17460
ggtcgttgat taactggtca agttccagta cacggtcttc gaactcggag ttaccccaac   17520
```

```
gcggcagctt atggaagact tcacgcatcg cagtgatgtc gctcacggcg tacctgatga   17580
acatcgccca ctcgtcaggg tgagtttctg cggtgtagcg gcggattttg tagttcttcg   17640
gcgtcggttt agagaaacgc ttaatcagag ccttgccgcg tttatctttc gcgttgtctg   17700
cagacacgcc cagcacttcg cacagcgcat caagagaacc cggcagcgcg tgacggaacg   17760
cccaaatcat agtatcaatg gtgttactta ccggaatatc aaagtcccga cagtgtttca   17820
tgattaggcg atcgaaaagt ccaccgttgt gccacaccat cttgatgcgg ctgttgggct   17880
taacaaggcg gcgcagtgcg cggtgtaaat ccccggcat gtcgctgccg tcggtgcaat   17940
cccatacccg cacaggttcg tcgtcaaaag catatgtaca gataagcact tcggttgacg   18000
ggtgttcggc gtaagcgtaa gaaccgactt tcttcaaatc ggcttctgag aatgtttcaa   18060
agtctaagaa caggtaactc attattttg acccctagta aaaaggccca atgaagggcc   18120
ttagttaaat tgattcagat gttagcggcg gcgacgttcg cggcgcggtg cttcatcttc   18180
ttcgtcgtct tccaggtcat tgacgctcgc agcgacttta gaaccgccga acgctttgcc   18240
ttcgccaacg tatttaatcg ccagcaggtt aacgccgagg actttgtatt tctggctgaa   18300
ccagatttca acgcttacgt tagctaagca tccgctgtaa acctgttcac cttcaatctg   18360
ttcgccgtct acgttgaagt cctgctctac ctgagtctca ccttttttag aggttacaat   18420
cagcggctgt ttctgtgcct tcgctttgaa gtagaagcct tccgggaagt cttcaaacgg   18480
attgtcgcgc tcggcaatgt ctttaatcgc gcatttatcc atgtgcttac cttcaccgta   18540
gttggacttc atccatttct cggcagcggc tgcgcctaac gcttcttcaa ctacagcgta   18600
aacggtgtcg tagagcgcgt cgatttgcgc gtggtcggac ggcaggataa tagtcgcgct   18660
gtactgacct ttagtgattg aaccatcatc attttcacgg tcttttttcgc gttcgaatac   18720
gttaacccaa gcagtgttta ctttacgcag atttaatttc agtcccattt ctcgattcct   18780
cagttttcag tttactccgg gagctgcccg gccagtgatt agaactataa tagctaacta   18840
ttcaggtgtc aacactttat tccaaatctt cttcactaac ctgattccac tcaggacgtt   18900
tgtcatctgc cgttgcgaca catggtgcgc ctggcttacg tgtaatgaag tctttcagtt   18960
catcttcagg cacaacttta accgcttcgg ttggcgtcat gagcacttgc ttcattagcg   19020
ctatgccata cttgccagcc actttctccg tcgtcttcca cacgcgatta ccctgacgac   19080
cttcaaccag cttgtaccca ggcactttct taccggaatg caaagcggca gccatagctt   19140
tctcaacctt atcgatgtgc tggcgcagca acggcaactt ctcatactca gctacgagtt   19200
gttcaggcgt cagttccagc gcaaagtcgt cctccagttc ttccgccagt acagaattaa   19260
ccgtcttgt acgcgcagcg cattgttcag agaaccggca ccactgacaa ccatctaccg   19320
atggcttgaa gtccgacgct ttcaggttct tcttgcctcg gaaatacgca tcaagcgcta   19380
acagcgcgcg tttctgtgcg aacttagcga acagttccag tccttcaacc gagatgtccc   19440
actctgtcgc gcccccagcg taaggctgga agatgaccag acgaacggtt gttatgttat   19500
aacgtctctt gagtcgacga taaaccgga gagcgtaaga cataagctgc ttgtttttctt   19560
tcgcttcgac gcgatgccgc ccggttttca gtcgcgccgat aatgagcatg tgctcgtcgg   19620
tgtttgccag ttcctggaca gcaacgaggt cagcggttcc gaacgtctca acgccttcat   19680
accccggatg caatacctca gtaagattga cacgcatttc cagcttggcg taagtcgcta   19740
cgtctataat cgctttgcaa tagtcggtgt acttgcgcac ctgctcaatc atgtccgccg   19800
taatcagtac cgcgcctttc atcgggctga ttagcgcctt aatctgacct ttgccttcat   19860
ccagtacgta agcgccgact tcacgctcca acggcaacgc agtgccgcgt atataggcgt   19920
tgagatggac ctcagctatg gtgtgcatgg cggttcctaa tacagcggct ttacccgacg   19980
tgttagggat atcttttca cacgccgcg acgcagcgca tgacagccac ttttagcgc   20040
ctgacggtga cgtaaggcg tgtacatcat tattgccgcc tcgttctttt agaatcatta   20100
tttagcctcc tccggtagtt ctggtaaata catccagtgt gttataccca tctctatata   20160
ccgtttcgta tataactgat ttccgttttc atccagccca gcagtaatgt cgtcgaaata   20220
gtcctgtata tgcacaaaat caattccgcc ttccgggaac ccattatcgt cacatttact   20280
tccgtctact gagcaaacta aaacagaatc atcttttgac tctggtagtg cttcgtttac   20340
gctaacccaa ttcatacccct gttctcccac tggtcaatta aatgtcgtgt cttatggtcg   20400
cagtgcatgg cccaccata catcgactcg aagacataaa agtcaggctt ggcgaaagtt   20460
gtgcgcttaa tctgtgacac gtgacggcct atatctttag gccgtggtac ttttcctaag   20520
tacgccatct cttccatctg gtgcgcaccg gacggagcgc gcaatagcca tagcgcctct   20580
gtgttatccc gcctgtcgac ggctcggtag agttggtaaa tcataattcc gaccctcagt   20640
taaagcggcc cgaaggccgc gagatagtta ttccttcttcg aaatacttgt tcttgattgc   20700
tgtcaggcgt tccaggtact caaccaggtc ttcgtctta atcgcggcaa tcttcatctt   20760
cttacctgtg aactcttcca gcagttcatc agaatcatca cacgcggcat cgctaggacc   20820
tccattaatt gcatcgtcga tggcctgaat ctggtcacgc agagacttgt aatcgacttc   20880
ttctttctct tcttccggtt ctggcgcagg ttcctctact ttagctttac gcggcttgcg   20940
ttttggcttc tcttcctccg ccggtttagt gtcaactacg tcttcacctt caaccgggat   21000
ttcttttgtt cttcttcag cgcactcagc taccgcttct ttggtgtacg ataccgtctg   21060
tacttccagc ggcgtggcaa cctgaacaac ttgtttcgca ctgttcgcgg caatcagttc   21120
atgcgcaact acgaaacgtt ccagtaatac taagaatttc tctaacatta tttattctcc   21180
tgtttatttg ggttactcgc cgtcgccttc tgtaaggcta tcgtctatta attcaaattt   21240
accgtttggg tgttgaatag cttcttgccc gcaatggtcg cagacaacaa gtttatcgaa   21300
cccatcaaac tcatccccca ccacgcaaga aagtacaaat ttatgttttg tgcacacttc   21360
ctgcgattct ccgaaaattg ctagaaaacc tttagctatg gctcccgtta ttgtgttcat   21420
atcgcccct ctcgtttggt atgggctaac tataatagcg aactattcac atgtcaatgg   21480
gcttttctaa aataattaat atggtactat tcacatatcg actgactaag gagtaattga   21540
catgcaacca tctgaactag gtatccgtgt agaacaacgc cgtaaagaac tcggcatctc   21600
ccagcgccgt ttggcggccc tgaccggcgt ttcccaggcg gcgattaacc aactggcact   21660
tggagtaact cagggcgtcc gtcaggcaac gctgttcaaa ctggcggaag ttctggaagt   21720
agacgtcaag tggctggcgt taggtgaagg ggcttaaagc ccctttcttt ttatagcaac   21780
ttatcgagtt cttccaaatt cttaatagtg tgtcgcacgt tcaggtactg aatccaggcg   21840
ataaaccacg cacttacagg aaaacttata acaatagtta tcgatataat taatttgaaa   21900
taaatctctgc cagcgtcatg tctaaaatgt ctttaaactc cgcaaaaatc   21960
cccgctgcat acacacaaaa agtccaccag ttgttgctta cagcggaaac acatgtcagg   22020
tatgacgggc ggtatcctgc cttcactgct ttaaacgggt tatctataaa atcgtaaata   22080
ttcattccaa atcctcctct gtcactgtca acatttcatt cggttcgtat attgtctttg   22140
gaatcttgtt atcagttatt ctggtgttca gcctgtaacg acctgggatt atctgattgt   22200
tttcgtcagt acccggaaca agatacccgg cctcaaccat ttttcttaatc ttcccgcgtt   22260
```

```
ctatggcttc tttggagtta aacgcctttg cgttggggtc agactgcgcg agcttattcg   22320
ctgcggatac cgtgatgccc tcgttgccgt tgtaggtccc ctccgccagt tcaaacgccg   22380
cgagtatcgt ggcctcggaa ctgttgacgg cgttctctat ggttttacgt acattttgtt   22440
taccttcgtt agttaaccct tcttccctct ctttctcctc gtcggtcttg aatggttcga   22500
agcccacgg catcaataca agagccttgt gcggctcagg caggtcgagg tttactattg   22560
tgccgtattc ctctgtgcta ccgaggaact caaccgcgcg gtactctttc ggcggcggtg   22620
cttcacggaa ctgtacagac tccagtacca tgccaaccgt cttctgttgc ggaccgtgct   22680
taaatttaga gtggtatacg tttatctgac ggtcggtagc gcgttcgatt gtcagttcca   22740
cgtcgacacc cgcatacaat gctccactgc cgcgggcttt cttcccgccc ttcggagtat   22800
ggtgaacgac accgacgcg gctttagttg catcgcgcac ttctttcagg atggcgataa   22860
ctttacccat accgattgcc gttgatgaac tgttctcgtc gaacttatca atcgtcaggg   22920
ccagcgtctg gttaagggtg tcgaaggcaa ccatgccaat aggttcatcc cctgcgttt    22980
cgcgcatcct gcggattaga gctggaattt ttttatcacc atgcgtagcg agtatttcgc   23040
ccatatcgat gacatgtaca taatctttac cttcctcgcc atattagcc gcgagtgcat    23100
caatacgtgt tcgtgtagct gcaccaccct cgccgtcaat atagaaatgg tggcaacgtt   23160
gggtgtcagc ccccgcaaac cggtaccgg cggcgctcag gtacatcatc cccagcgtat    23220
agaacgattt gtacgtgcca gattcccga cgatatccca gatacaatcc gacggcatgt    23280
accctcaac gacgaaatca gcctttaccg gctccggtaa ctcgtcctcc tctgagtcct    23340
cgtcgtcttc caggtcgtcg aggctgcatg agacagattc acgcgccccc caaccgatgg   23400
cctctgcgca ttcactgaac ggcagcccgg tcgcatcgca cgcgtacttc cacacctctt   23460
tcggtgacag gccttctgtc gccgtaatgt ctgtgtcgtg aatcatggtt acgtttggcg   23520
cttcatacc ctcgcgggg aagcacagca ggaagtcgtc gtcgggtcgc tcggtcacg     23580
tgtagttttc ggcatgttcc ggtgtggctg gcatcttaag gccgcgcggc gtcatgacgc   23640
cgccgtactc aaacgccagt gcttcaaacg cgtctgtaaa cgcggtgcgc agttcttccg   23700
gtatctggta atccgatgcg ctgctaacgt caacggctgg gacgccttcc agtaactcgt   23760
tcgggtcgat caggtcgttg cggcgcgacc agataacggt agcgccgacc ggcggcaggt   23820
acatcggctg cgacagagtg aacccgctgc ggtccgcacc catgcctttg aagaagtgct   23880
ccagcaaccc atgacgaaca cggatgatat caccacctc aactgggcgg gccagcggca   23940
tgacgacgcg aaagcgaggc gactcatcgg tatgtgatgc cgtggtgtag agacacatcg   24000
cccggcggct gcgcttaacc aggcgcaccg cttcctggta ctcttccggt gttgtgcgt    24060
cgaaatccag ataggccagc gacgatttgc ttacagacgc atcgcagcgg tagaaaaaac   24120
ctttacgcgc ttgcttaaag tctccagttt ccgggtcttt tacggtgctg tgcgttgagt   24180
cgcacgcggc ggtgatataa ccgggcgcgg tcttagggtt aatcccgtcg cgaacggcat   24240
cgagcggctg gattaactct ttcaggtcgt ccagtgttgc cgtgtgtgcg gttctgacat   24300
ttatatccttt tttccccgcc cgcgcgttgc ggcgtgacca cgagtaggat aaaattacat   24360
cggacatgtt gtatttcctt cagcaagtaa tttagcctcg gcgctctaac gtcgggcttt   24420
tcttttattc caggtcttct acagtagcgg tcattccgcg aacttcagca actgcgctat   24480
atttcccacc aacatttttc acgacaccag atttaaccag taccttcaac gacccttcaa   24540
taatggcgga actatagtac ttaaaataac tacggcgcaa gtccataacg ctgcacgacc   24600
cttttttacg tgttaatgaa acgactgccg taaatacgcg tgactggaac tcgctcattt   24660
tacattctcc ttaatccacg cttccacttt ctccggtca aacgtacctg gctgacggcg    24720
gcccataatg cggatacaac aatccgggaa cttcccactc tttaaccagt tattcagcgt   24780
gcgacgggta accccgatac gctcagctac ctcattctgt gtcattctca aaccctcatt   24840
atcagttaac gaaactgagt atacattgcg aataatggga aatcaaacat aatcgcacct   24900
attgacatta tgaaaatctt cgtttaaggt gcttttatat cttagttact ttgattcttg   24960
ttcaccttgt aatacccgct tgaaacgcag cggcgcacca cgccagcga agtgttaagc    25020
ggcagattac tgaacatatg aattatcgta acttccttc ctaagtatct ccggttgccc    25080
tgggcaagct ctattctcat cgacggcata tctcttaagt atctgataat taaaagtttc   25140
tatagttgcc gtgagcaagg tagagagtac ttcactccgc tggggtgggc taacgcccac   25200
ccactgcgtt gcgtactctt ttaagaaacg aaagaatcac aacggcaacg taactattct   25260
cttgcacacc ccaacataat aggatactat tcacttatcg aatcgagaca gaggagtgag   25320
ggttatgctt aagaagggtc agttggtccg tagtaaaaag tcgggatgtt tgtactccat   25380
attttccacc aacaacagag gcagtgccac catttgtaaa cttcgcaatg tatttactga   25440
cggccatgca actgtaagcg cggaatattt aacactcatc ggtaacaatt ttaaattcaa   25500
aggggtgaag tgatgcaaat cataattaca gataacacg ttatctacga agaagatggt    25560
gatactctcg agaaaatagg cgtaaatgtg ggtgatgttt tcaatgtact ggattcctgt   25620
gaggatggct ggtggattaa gacaggaaga tacacaatcc cggtaactaa ggcagaagcg   25680
aaggtataca caacggcatc taatcatgat gctcgtgccg acgactctga gggaggttgc   25740
cgtgaataat attttaattg cgggggttgg tatgagtccg tataacgaat tccgcttacg   25800
ccgtctgatt ggcggtctgc gcgccgccga gtttgtgtt gaatgctggg aaaaggcgaa     25860
gtacaccccg tggaagtcgt ggcatttggc tcatgctaag gcggtagcac agtaccgtga   25920
gtacaagtta aacagttttc ttaagcacca cggggttgag ttatgagaga gcatttgaa    25980
cgtcgggccg ttgcagatgg tctgcctgtc aacaagggct cgcggaacga gtaccttagc   26040
gctaagacgc gtctcgcgtg gcggatgtgg aaagctggtc tgcagtatgc gatgaatacg   26100
aggtgagata tgggcgagtg gattaagtgt agcgagcgga tgccagaaaa gaaccagagc   26160
gtacttattt cggtgaattt cgatagctct ctggttgagc cgctaatatg ctccgcacgc   26220
tataccggaa gcacatttcg gcgaggagat gcaacggtta agccgggtaa tggtgttgag   26280
caagcaactc actggatgcc gttacctgag cctccggaag ggtgatgttc aatagtttgg   26340
gattttactg agtgacttac gctgctacac agcagcgtac aactttaact tagtgtcgtc   26400
aaaaagcgac actttcacca aacgcaacaa tcgaagcgac tattgcagga gatgcaacaa   26460
tgaaactgaa tgcatcgta acctggacca gtagaaacgg agaaaagcga ttcgggctta    26520
ttgttgcgtc agacggcagc aagtaccgtg ttatgcgatg cgtcagtgg gcacgacgcc     26580
cgaggtacta ctggattcgt agcgaacgat tatctttaaa acaccaataa aatttacttg   26640
cacactaaga tagaatagac tactattcat ttaccacaac gagaggagag acagaagatg   26700
agtaacaaaa acgaagtatt cgagtacctg attgaccagt tacggcagca cgtaaatagc   26760
cacccataca agcaacagtg cgaagacctg gcacatgagg tgctgtcact taagaatcag   26820
ttacgtgatg cgtcggcgct ggtggctgag ttgcagagcg agttacagca tcaaattgac   26880
atggcggcgt gtgtgcatag atggtctacc gcatatttcg acgagaaagg taaagtcttc   26940
aaggtcgaga gtggggttaa gacagagcaa tccggttgcc aaataggtgg gcatgaatgg   27000
```

```
gtggcgacac tgcaagatga tttccgtaca tgcagcaaat gccatcggga agagctgata   27060
tgaccagcat cttatttatc tgggtactgt ccgcaggcca gatgcaacta gcggcatcag   27120
aaacgtttta ctcaatggag gcgtgccagt aggctgcccg cgctgcagag gacgcgcact   27180
ttctgtttca gggcgacaag ctcaacgatt cagaggtacg cgctatctgc tcacctaagc   27240
gacttggtaa acaggagaag tgattatggt gcagagatat acctacgacc agatattcgg   27300
gtttactcct gatgttgagg gcgtgttagt gctttacgaa gattacgcga aacttgaagc   27360
tgagttacag aaatacaagg accagtaccc tgattacgtc gagtgcgcga actgtgggtc   27420
ggttacacat gtggaggggg tggagtgatg tcgttagcaa ctgacatcct gaaacgaagc   27480
ggcattgcgc cgctgtcacc gagagcgaag acacgtatac acaagcgtcg ccgtaacgtg   27540
ctgtacccag agatacaaga acggcgtaaa gctatccgcg cctgtggatt ccagaacgga   27600
aaggccgtta acctcggtga gtttaaaaca caggaacgcg cagctatcgc taatcggtta   27660
tttaattact ggaaatcgct gggatacgat gatattccat cgaaaccgca gagacgacaa   27720
tacatctggc gtcataaata aaccgttatt aagataattc ctaaccgtgc tatcctccag   27780
ttactgcata cttaatacgc acctggagga ttcatcttgg ataaatttac tgaaacagtg   27840
acggggtggc ttctcgctgc cgcactggtc ggtggattgg tcggactaag acaacataaa   27900
aagtctatat ccgggccgat tgacggactg gtatttcttc tcaccggctt cgcgtgcgcc   27960
atttttcggcg cacctcttgc cgctcaatgg tttggtatta ctggcgagcg cgagatagct   28020
ggcctcggat tcatcattgc tattctctgg atgccaattt attcccgtct ctctggcatt   28080
gtcgccggag aatacatcgc acgtcgcgga ggtggtaatg aatgagttat tctggtttgg   28140
tggtatgctt tcaatgggcg cttcgtccct gttcaacgtg tataacggac acgtgggcga   28200
cgggctgttc gggcgtgtgc tttatattct gactgctatt gtctgcgccg ccggatgtat   28260
ccacctgtta cagggcagca tgtcaccgac gctgcctgag acattaatca cattagttgc   28320
gctgcgtcag attcgtcagg cgtggctgtc gtacggagga cataagcgtg tctcgaaaca   28380
ttagcaacaa tggcatcaaa ttccaccgcc cgttcgaggg gttccgcgga actgcgtatc   28440
gtgctacgcc aaatgagaag tacctgacta ttgggtacgg tcattatggg ccagacgtaa   28500
cgccaggcaa gaccatcacc ccgggacaag gcctcctgtt actgaatcgt gatatggcca   28560
aggcagtagc ggcggttgat gctgcagcgc accattcatt gacacaggca cagttcgacg   28620
cagtgtgcga cctggtgtat aacgggggtg ccggtgtgat tgcggctact actggacacag   28680
gtaaggcact gcgttctggt gatattgcaa cgctgcgggc taagctggcg ctgttcatca   28740
accagaacgg caaaccgtta ctaggcctgc gtcgccgtac cgccggtcgt ctggcgctgt   28800
tcgacggtaa accgtggcag gaggctgagg ctatcgggcg cgcggtgaaa ggttgacaca   28860
taagactaat ccgacgatac ttaaatcacc tcctgctcca tccctctgct ctccagtttt   28920
atcccggccc tgacccagcc gggattttt tttatctatt ttctgtgatg actagttgac   28980
tattcctc gacccttatta tatttactc atcgacaacg agaacggagt agagaaagatg   29040
agtaacttcc ataatgaaca tgtgatgcag ttctatcgca ataatctgaa aactaaaggg   29100
gttttttggga aatgaaaatc acagataccg aagcattcga agacgcgcaa ctgatgcac   29160
gcatcgccgt tggcaacctt agcggtaata tcccggccga cgcgttctgg gccgccgcga   29220
tgcaggcact gaaagcagct tatgcaggag agaagaaatg agcgaacaag gtcaagtaag   29280
ccaaccatta cgagtaggcc ataaagtcag tcacacccg ttccccgacac gcgaggaact   29340
gatgaaacgt aacagtttcc cggggccgga caagaacaag tatctcaatc gcatgtgggg   29400
agagcgtaaa gaatgaccga ccgtgaatac gaaaagatga tggtggaggc tgttaacggc   29460
ggcgtagaca tcggccatgt gatgcacgtc ctgaatacta aaatcgcggt agccgagcaa   29520
atggtggagt cgctttatga gacacgcgt gaactgatta accgcttcaa ccttaacaag   29580
gcctcgggtg atgggtatga aagcgcctga accgtagtt attgatgcg tcctgtggaa   29640
accatactcg gttaaccaca tcgacgccga cgggaagaag tttagcttct acatttttgg   29700
caattagccg tgagcacgcc gcttgtgtgg ttgactatat acgggaaacg gcgtggcttg   29760
gtgatgagat agtgggtga gagtatgagt ctagaggtgg ttattggcct tgtagcagca   29820
ggttattttta tcggcgtatt gattgggttt atgtgggta gagacagtgt tcagtgacat   29880
caacgcagca atcgaagagg caatctggcc ccgatacaac ggagagcagc agcggcactt   29940
ctgcctggtg caacgcggca acatggtcgc cgtagtgcag gaccgcgata acaaatatcc   30000
gaatgcgatg tggacgacga ggaatttctt atgatgatta ccagcattcc taaccttgct   30060
aaagaatttg gcacgatggc ggagacgtgc cgacaaacag gcctcaacga aatgacgatt   30120
gcgaagtaca gcaaagacgt gaaatgcgat cgccatgtaa tttataataa ccgccttatg   30180
acgcacgtta agacaagccc ggtgctattc acacgccgcg gtatcactaa aactgaacag   30240
cgcattgcta aaggggagag cggggaatga ttgagattt gagggctaca aatgctgctg   30300
gcgacctggt gttttggctg gcctttctcg gcgtactgat aaaacaaccg actttgttta   30360
acagtattcc ttgctatctg tggtggccta tgtttttagg catgggtgta tcaggagtag   30420
ctggcgtcct tttgtggttt ttcaaatgag actgctaatc atccctaacg cctgggctat   30480
tgccgtagct aacgaccatt acggcggcga cggtaaaaga gcaccagcac acggcctata   30540
taactgatac aagccctcta cggagggctt ttctgtacat cccgcccaat ccccttatat   30600
aatcccttta gacgcgtagg gcgcgtctgg tgcgctctga tggtcagacg catatgcaag   30660
gggattctat gaagctgaaa cttaagcagc catcaccaga ggtggtgcaa gctgcacatg   30720
aagaagccgt tagcgcaaac cgtcgccgta aacgaccgcg cggcaaacag agcctttatc   30780
aatcatcccg taattctgcg gcattgtggg acccggacta ttgcgatgca ctaatcgagt   30840
tcttcgaccg cacgtcgtgg gagcttgtgc ctacgtctaa gggtgacgaa cgcccgctga   30900
ttcaggataa accaccgtca ctggcccgct tcgccttaca catcggagtc actatcccga   30960
ttattaagct ttggctgcgt gagattcccg catttgcaga agcctgggag acagcacagg   31020
cgctggaaga ggcatacttc actgaaacgg gggccgcggg catctctgct acgtttgctg   31080
ccgcgaaact gggcctgaat aaaaacagttg tcgccgaaga agtacgcgag gagccaatca   31140
gcgaagtaac aattaaggtg gtgtccggtg aacgttaata tcacggcaac ggagccgcaa   31200
ggcgcgtttc tcggtatgca ttgcaagttt ccggcattcg tagctggctt cggtacgggt   31260
aaatccgaag ttatgtgcaa ctctgcacta ctcgacagca tggaaggtgg tagcgattct   31320
atcatcgcca tgtatgagcc gacttatgac ctggtgcgcc tcatccttgc accgcgtatg   31380
gaagaaaagc tcaccgactg gggtatccgg tacaaataca acaagtctga caacataatc   31440
tatacgtctt ccggacaatt tgggggattt gttctgcgta cacttgataa tccagcacga   31500
atcgttggct acgaatcgtt tcgtgcgaaa atcgacgagt tggacaccct taacatggag   31560
cacgccgagc acgcgtggaa caaagtcatc gcccgtaacc gccagttgcc gcggacatat   31620
aaacctatta caccgaaacc tgctaatacc gtttccgtgt tcactacccc ggaaggattc   31680
cgtttcgtac atgaccgctg ggtagtcaaa aagaatccag gctacgagat gattcaggcg   31740
```

```
tccaccctgt ctaacccgtt cctgccagaa gattatgtgc agtcgttacg cgacacatac   31800
ccaggtcagt tgattgacgc ctacatcaac ggcgagttcg tcaacctgac ggcggggact   31860
gtctattacg cctatgaccg caggaaaaac agcagccgcg aaacaataaa accaggcgag   31920
actctgtata tcgggcagga ctttaacgta ggccacatgg ctagtacagt ttacgtgcaa   31980
cgtgcaaag tctggcatgc agtcgccgag ttggtggata tgttcgatac gcccgatgtg   32040
gtgagagccg taacagacg ctggaaaagt aagggccact atatcgttat gtacccagac   32100
gcaagcggta aaaccgtaa aagtaacaac gccagcacat ctgatattgc ccagttacag   32160
caggccggct tcgaagtgcg cgctaaatcg acaaacccac cggttaaaga ccgcgtagcg   32220
gcgatgaata aggcgcttga atctggtatg gtcatgatta atgaacagge ttgccctgtt   32280
accgcacgat gcctggagca acaggcttac gacaagaacg gcgaaccgga taaatcaggc   32340
ggtgtggacc accagaatga tggaaccaca taccctatcg cgtatgaaat gccgattcgc   32400
aaaccagtta ttaacgtccc ggtgactttc gcactttaag aggattattc aatgttaact   32460
atgaacggtc agaatcaggg tgttaagaca aaacaccggg aatggctgca tcacttcgat   32520
aaatggcaga aggtacgcca cgctcttgaa ggcgacctta tccgctatct gcgcaacgtc   32580
gggaagaacg agcctgacca gacctacgca gcacagcgac aggaagaata cgagaacggc   32640
gctatctgct acaatttcac caaacgcacg ctggtgggga tgacgggtc agtgatgcgc   32700
aaagaccctg agcagattat cccgcctgaa cttgagtacc tgttgcgcaa tgctgatggt   32760
tccggtgtcg gcctgtgca gcacgcgcag gatacgctaa tggagattga ctcgatggcg   32820
cgtggcgggt tgctggtgga cgccccggag acagccgcgg caacggcggc agaacagaac   32880
gcgggattat taaacccggt catcgctttc tataccgcag agaacatcat caactggcga   32940
ctaactcgcg ttgttccgt taaccgcgtg acgatggtcg tgctgcgcga ggtgtgggaa   33000
tactcagaac cgggttcaga gttcgaaaca aagttcgggtg agcagtatcg cgttctcgat   33060
ttgattgacg ggcgctaccg ccagcgcatt taccgcttcg acgccgaagg tggcacacag   33120
gatgaagtaa tagagatatt cccggaactt ggcgaacagt tgcgcggcaa aatcccgttc   33180
acgttcattg gggcgggcaa caatgatgca accattgacg atgcgccttt gctgccgtta   33240
gccgagctta atattggaca tttccgcaac agcgcagaca atgaggaatc cagcttcgtt   33300
gtagggcagc ccacgttgtt catcgcccca ggcgagaaca tgagcatgga acaatggaaa   33360
gaagccaacc ctcacggcgt gcgcatgggg tcgcgttctg gccataacat cggtcacggc   33420
ggaaatgcgt ttctggttca ggcggagag aacaacctcg ccaagcagaa catgctggat   33480
aaagagaatc aggccatcca gattggggcg cagcttatca ctccgacgca gcaaatcacc   33540
gcagaatcgg cccgcctgca acgtggtgcg gatacgtcag tcatggcgac aattgcgcgt   33600
aatgtaagca tggcgtacac cgatgcgttt cgctggggttg ctgcgatgct tggattgcgt   33660
gaagacaccg agattgagtt caaactgaat atggagttct tcctgcaacc gatgaccgct   33720
caggaccgct ctcagtggat ggcggacatt aacgcgggcc tgttaccagc tactgcttac   33780
tacgcggcat tgcgtaaggc tggtgtaacc gactgacgg acgaggacat tcagaacgct   33840
atcgaggatg cgccgctgcc gattggcggg gctactccgg tagagggaga gattccgcag   33900
tcggcgcagc aacaggacac tgctcagcgg taagttcgcc tatagccccg aaaggggctt   33960
tcatatagta tgctattaac tttagcgcca cagggtttat ctatgagctt acttacatct   34020
ctaatcagcc accagatatg gctgcaacgc accgcatccg gtgaagtgaa agacctcacg   34080
ccgttcattc aggagataag ggatgaaatc aaacgcagg tgctgttatt cggtgacgac   34140
gggcgaagca ctgcccgact gaataaattg ttacgcgacc ttgaagaagc actggtgggg   34200
cttacgggcg actggcagac aaagctgaca gaagaccttta aggaactggc ggcgtatgag   34260
gctgagtgga acgtaaagac actgaccgcc aacgtagacg cggaaatttgt tacgcctacc   34320
gctgagcagg tatgggccgc tgccgagttt caaccattat cattgagcga caagcccgtt   34380
gatttccacca agctgatgtc tggatggggt gaaacggaag tagcacgtct tgtaactgga   34440
gttaagatgg gctttgtgca aggtcaaacc acacggcaga ttgttaagaa tgttgttggc   34500
gctggtggac tagccgacat ctcagaacgt aacgcgacta cggtaatccg caccgcgctg   34560
tcccacgtat ccaacgaggc ccgtaacgag acgtaccgcc agaacgacga catcatcgag   34620
aaatatgagt gggtgtcaac tttggacagc cgtaccagca cgatttgcag ggccagagac   34680
ggaatgacgt gggaaatcgg taaaggtccg atgccgccag cccatccgaa ttgtcgaagc   34740
accacggcc cggtaatcag ttcagagttc gacttcctcg ataaaggcgc aaaacgcgcg   34800
gctaaaggcg cggaaggtgg cactcaggta agccagacga ccacttacta cgagttcctt   34860
aaacaacaac cggcgtggtt tcaggaccag cgctcggcc cggtgcgagg taagattttc   34920
cgtaacagcg gtatatcgcc ggaagagttt cgcgtaatat ctgtagatgg tttcgggaat   34980
ccgctcacgc ttaagcagat ggcggaactc gataaacgtg ttgctgatta tctgaaaggg   35040
gaataatgat gggcttttc aaagtaactg acgtaccgtc tcgtcgcgta gtccagtacg   35100
cccgcgtgtc tggctctggc gagaacgtgg tatttattga ggacgaaagt gtactcggta   35160
caccggtaga tgatatgccg tttgcagata aaaccgtat tgcgttgccc gccgctggta   35220
tgctttatga aattccgtat ctggcggacg ctggccgtgt gtatttctct gcgcaaccgc   35280
aggacgctga actggcgggc ggcagccgaa ccatcactgt cgaggttaag gcaggcaaag   35340
cgccgtattc tctgacctgg tacaaagacg gtaaggaagt ggtgaatgcg cctgaggagg   35400
ctctgtctct gacggttaat gcggtcgcg aatacttcgt taaagttact gatgccgatg   35460
gggtagaggc cgtcagtaaa gcggcgaagg ttactaagcc ggaatgataa aaagcccgc   35520
tatgggcgtt tattttata tgaacatcgc ggtgatgcc gcagccgata cccacaaaac   35580
aaaataaaac atcacactat ttgtcatttg catttctcgt cgtatgttg ttgtaactgc   35640
gacagacgat taccggctgt catctcgtcc atagaaggcc cggcgccgt gtccataaag   35700
aacagcggaa caatcaggaa tgcgcctgta acaccgagta caacgttagt acctatttgc   35760
ttattaacac ggtgcgtagc gttggcttga gcttgttttg tcgtggcgat tctcgatagt   35820
aactgattac atgttgccgt tgtatccccc gcctgataaa cctgtaaagc cgggtctggc   35880
aacgacctta cgcaaccact caaacaaacg gctacaacac ctgctactgc taatttaata   35940
tatttcatag ttcacaccat tacccgtgtc aatgtcacca ataccactac aagcccaaag   36000
aaacatcacc gcatcaactg caattactac tgaataacg actaacatga cggcctcccc   36060
ggttcgatag aatgaatagt acccctattat attggggtgc gcaaactatt tatttacgta   36120
ttcctattat tccagttat tccaccgaat tgtaaatgtt ggaataaact attcgaatag ttgactttta   36180
actaaaaatg tgataagctc cacctgagct tgtgaagtaat gaacaagcga ccgcggcgcg   36240
ggcaggtaac ggagcgggac gtaagtcctg agtgtagtta cgctgacgcg ttcggaaggg   36300
ccatactcta ttgcttgtgt aaaaagtaac tggtttactg agattacgcc gtttctatgt   36360
ttaaatgata aggactagcg ccctgcttta aggcagggct ttacttatcg agaaggggaa   36420
aacatgaatc ttaaagcaac cgtcgtagca ggagcatgtt tcatcatcct ggcttacaca   36480
```

```
cacggcattt atcagtaccg cagcggctgg cacgaaggcc gcgctaatct cgtttcgcag  36540
caacagcaaa aagcacaggc tgagttagct aagaaaacac aacggcagca gcaggacgaa  36600
tcaaaggccg ccgccgccga caacgaaggc aagacgaaat cagaggtgat tacccgtgaa  36660
gtcgttaaat acattaaaac gccaggtcgc agcgtgtgca ctttcgacga tgctcgcgtc  36720
ctgctcaagt cccacgccgt cgcaaacgct aattccatta ccggatacga cgatgatgca  36780
gcctccgtgc aaactggcag cgccaagtag cgacgctgac gaggatttag ctatcgacgt  36840
tcagaacgct gaatgcgtac ggcagctgcg gctgaaagtg ttcatgttgc aggattacgt  36900
gaggaatatt ctggaatagt tgccttgcat gttggaataa tttattcttg acatgtaaat  36960
ccgggtggcc cgggttccaa cgtccagggg acatactgac tatgaatcgt tttttacgtt  37020
atccgttcca ggaagaagct ggggtagaag ataaagctgg tggcggtgac gcgccgaaaa  37080
tgttcaccgc tgaagaagtt caggcgctga ttgagaaaga agttgccggg cttaaggcta  37140
atcaggaagc attgttggcg gagaagaaag aagccgctcg caaagcaaaa gaggccgaag  37200
aagaacggca gcgcgcgcac caggaggcgt taaaagccgc tggtaagatg gatgagttcg  37260
aaaagacgat tcgtagccag tatgacccgg tgttagccga gaaagacggt cgcatctcca  37320
gaatggcaga gcgtatcctc ggcagcgaac gtaaagcggt gctaggctct ttcgcgggtg  37380
actttattac cccagaagca gtggacattc ttgcgccgtt cgttaagact gagttcgaag  37440
gcgatgatgt ggttactaag tttgttggtg cagacggtaa cgtaatcacg actgacccgg  37500
aacagttccg caaatacctg cgcgaacaca aggcgttttc gcatttgatc aaagcaaatg  37560
cagcttccgg cggcgggcct tccggtagca aaggcggcgg ggccgcacca gcgtttaaag  37620
acatgagtga agcagagcgt ttagccctgt ataaatcgaa ccctgccgaa tttgaacggc  37680
aacttaaagc cctgaggaaa taataatggc aattaccact atcggcgata tcgtaactgg  37740
caacatcccg gtcctggcgt cttatatgac cgaggaccgg gtagaaaaaa ccgcgttctt  37800
ccagtctggt attctcaccc cgaccccata cgccgccgag attgcccgcg gcccgtccaa  37860
cgtcgctaat attcctttct ggaaagcgat tgatacctct atcgagccga actactcgaa  37920
cgacgtatac ccggacatcg ccaccccgcg taacgtgcag accggcgaga tgatggcgcg  37980
cgttgcgtac ctgaacgaag gtttcggtca ggcggatttg accgttgaac tgaccagcca  38040
gaacccgctg caatccgtag cgtcacgtct ggataacttc tggcagcgtc aggcacaacg  38100
ccgtctgatt gctaccgcgc tcgggctgta caatgacaac gtagctgcta ccgatgctta  38160
ccacgagcgg aatgacatgg taatcgacgt gtctgctact ctgggcttcg atgcgggcgc  38220
gttcatcgac gctacccaga ctatgggcga tgctctgatg gcaacggcg gtgaagtgct  38280
ggggctatc gcgatgcata gcttcgttta tgcgcaggca cgtaagcagc agcttatcga  38340
cttcatccgt gacgcggaca acaacaccat gttcgccacc taccaggct accgcgtgat  38400
tgttgacgac agcatgaccg tagtcggcac tggcccgacc agtaagttca tctccatcat  38460
cttcggcaac ggcgctatcg gttacggtga aggttctccg tccaacccgc tggaatacga  38520
gcgcgaagcg tcccgccgca acggcggcgg cgttgaaacc ctgtggaccc gtaagacctg  38580
gttgctacat ccgtttggtt acagcttcac cagtgcagta atcactggca acggcaccga  38640
gactaccccg cgctctgctt cctggcagga cctggcgaac gcctccaact ggaaccgtgt  38700
ggttgaccgc aagcacgtac cgattgcctt cctggtaact ggtgtcggtg cttaaggtta  38760
agctataatc gagagggact tcggtcccta ttttcattta ctaagaggta aattatggct  38820
aagaccggaa aaggcttacc gcgcagcctt cagaatgtag acttcagcgt cattgatatc  38880
ccccgtcgct cctgctacta cccgcaaagt tggtgggggtt aaaaaggcgg cccaggtcgg  38940
cttccctgtg gccattaccg ccgccgccgg ggtgcagtcc gccgcggcac cgactaagga  39000
agagttcaac gtgcttgtgg cggagtacga caaactgcga caacgatgtta tcgcgctgcg  39060
caataccgta ggaactctag tgaccgcgct taaaaacgca ggaactgtaa gctaaaggag  39120
cttaaaaatg gttgatgtaa tcaaacgtcg cattaccggt gtttcagccg ataccgtagg  39180
cgctaaaatc gatatggcaa atatctcgcc agcgtctttt tctgccgcgc ttgcggctac  39240
caccgcagtt acggtggggc agactatgac tcttaccgta gtggtaactg gcggtctgaa  39300
gccgtattcc taccagtggt acaaagataa caacgccatc gacggagcca ccgcagctac  39360
ctatgcgaag gcgtccacta ctaccgcaga ttcaggcacg tataaagtgg ttgttcacga  39420
tgtgtatggt aatattatct ccagcagcac cgtagcaact gtgtcttaat acaacggccc  39480
ttcgggccg taataaggaa aggtcatggc agataaattac gtaatccgcg aaaagtatac  39540
ccacgttgat atcgttgacg gacaggtgat gcctgttcgc ggtgtggtag aagcggatga  39600
actggttgca acccaaccag acaatgaaga agcgcacaac aacggcgtg gtactaagcg  39660
tcgtcgccgt aagtcagagg aataatttat gccgctaatc gtggaaactg gggtgatcgt  39720
cccaaatgcc gacagttaca ttagtctggc tgacgcccgc gcgttagcgg ctaattatgg  39780
ccttgagctg ccggaagacg ataccgcagc agaggtggcc ttacgcaacg gtgctactta  39840
tgtagggctt gcagaaccgc agatgtgcgt tcgtcgagta tccgccgaac agtctcttgc  39900
ataccccgc accggcgtta cgttaaacgg gttcccggtg tcaacaacg ccattccgaa  39960
acaggtgatt cttgcgcagg taatcgctgc cgctacatat ggcgagggca ccgaagtccg  40020
ggctaactca gacggtcgcg ccgtgcagac tgagcgtgcg gagggtgcgg taacagtgac  40080
ctacttcaac aatggcaaca gtggcgctac gaccgcgatt accgctgctg acgacgcttt  40140
acgcccgtta ttgtgtggcg tcttaacaa tggtttctcg tttaacgtgt accggggtta  40200
aaaatggcga agactaaatc agagatattc acgctaatcg gttccgagct accggacaac  40260
acgaccgaca ttattacgcc tgcgaagttg cgcggggtat taacccagat ggctgactca  40320
cctatttacg ccactccggg tgttaaagag gttgaagttc tccgcgctgc gtcgacagta  40380
gcgcaagcgc ctaccgcagt agatacgcg ttgcaggtat cgttcggctc tgctcagggt  40440
agtgcatctg acccggtaat gattaatgct gcggggctgg ttacattcaa caccgcgggt  40500
aactatgccg ttcgcatcaa gttacaggcc ggtcgctccg gcgctagcgg aacgtctatc  40560
ctgttctcgc gtatcctcat caggccgct cagtacggct caccagcagc tacgaaactt  40620
gttagctcgg aaaccaccat ccctattgaa tcccgtgtag tgattaaccc aaccgccggg  40680
caaacattcg ccgttcagat tatgcgagat agcgccggga ctaacttcgg aggcgtatac  40740
ccgcaggtgc tactgtaac tgcatggggc acggcaccgt ccgcgctact ggttatttcg  40800
agactggagg ctgcctgatg agcactgctt tcagtaaacg tatgcaaggc gtgggtacac  40860
gcctgctaac caaattcggc acacggtat ctttggttcg cgctgcgtcg aaagtgtggg  40920
acgaagttct cggtgagtac atctcggtccg ccgatgaagt tctgccgttg aaagccgtgc  40980
ctgttccggt taacgcaggt ttggttaacg gcacaaccat tcaggccgga gacatgatt g  41040
tcaaagccga ttgcagcgtc gttccgaaga tggaggacaa ggtgcaattc ggcggcgagc  41100
aatggtccgt cgtagccatt gagaagaagg tggttaacga tgatgttgtg gcctacttta  41160
ttcaggtgag aaaatgagtt tcgcgctgga cgtctctaag ttcgtggaaa aggcgaagaa  41220
```

-continued

```
gaaccctgag aaggtgatgc gtcaggtgtc tatcaagctg ttttccgcta ttataaaggc  41280
gagtccggta gatactggtc ggtttcgcat gaactggatg gcatctggcg gtactcctgc  41340
ttccgggatt acggatgcta cggataaatc aggaaacaca gcaaccggaa acgctacaag  41400
tttcgtgctg aaagccaccg actggcatga gttcacgctg acaaataacc tgccgtatgc  41460
acaacggctg gagtatggct ggtcgcaaca ggccccgaca ggattcgtca ggactaacgt  41520
gtcccgcttc cagcaactca ttaacgaaga agctagcaag gtgagatgat gggctacttt  41580
gaggacttaa caaaagcgtt tgatgtgccg ctggtagcct tcggaaccac caacggaatc  41640
aaggtagcgc ttgaaaacat cgacgcgccg acgtcaacag atacgccgta tctggcaagt  41700
tacatgttgc tggcggatac cgagcaggct gatttattct tcacggaaca acgcgccggt  41760
gtctatcaga tagacattaa ctacgcatcg gtgaaaggta gcgcgccaat caataaaatg  41820
gcagacttac ttaacacggc gtttaaatca ggtaaggcat tttcgcgtaa cgacatctgc  41880
gccgaggttc aatcggttag cctggggcag ctgattgtag aaaacggatg ggccaaacga  41940
ccattgtcaa ttaactttat tgcattcacc aagaggctgt gaatatggct acaacttctt  42000
ttaagggcgc gaataccgcg caattctatg tggcggaaac taccccctggc gtaacaccga  42060
ctaacccggt atggtcgccg ttgcgtaaca cgggcggcgt tcccgctgta acccgcgatg  42120
cactgacttc caacgaactg gacggcagcc gtgaaactac atccatccga accggtaaca  42180
agcaggttag cggggagtat gccatcgaac ttagctctcg tagccaggat gatttccttg  42240
cgggagcgat gacttctacg tggaaagctg gggtagagat tactgcgcc gaaattacgg  42300
tcgccccagc aggtaaaaca ttcacccgcg ctgctggtaa cttcattact gacggtgtag  42360
aagttggcga ccttattgcg ttcaccgact taaccggcga caacgcaaaa ccgtttatcg  42420
tgaccgcggt ttccgctctg gtagttacgg gcgcaggtat tcagcacacg ctgacagcag  42480
agacagtaac cactgacgca aaaactggcg acaagctgga aaccggtaac gcgtgtaaga  42540
cgttctccat cctgacgtgg ttcaaggggc agtgtggtaa cctggacgcg tacatgctga  42600
ccaaaggtgt ggaaatctct ggctttaccg tagagcaggc ggttaacgcc atggtcaccg  42660
gcagcttccc gttcatcggc ctgagtcagg agattcttac cgcgccgccg tctggctctg  42720
atttctctca ggttacgttc accgatgagc c                                 42751

SEQ ID NO: 2              moltype = AA   length = 162
FEATURE                   Location/Qualifiers
REGION                    1..162
                          note = synthetic_EC340
source                    1..162
                          mol_type = protein
                          organism = synthetic construct
SEQUENCE: 2
VSRNISNNGI KFTAAFEGFR GTAYRATPNE KYLTIGYGHY GPDVTPGKTI TPGQGLLLLN   60
RDMAKAVAAV DAAAHHSLTQ AQFDAVCDLV YNAGAGVIAA TTGTGKALRS GDIATLRAKL  120
ALFINQNGKP LLGLRRRTAG RLALFDGKPW QEAEAIGRAV KG                     162

SEQ ID NO: 3              moltype = DNA   length = 489
FEATURE                   Location/Qualifiers
misc_feature              1..489
                          note = synthetic_gene encoding EC340
source                    1..489
                          mol_type = other DNA
                          organism = synthetic construct
SEQUENCE: 3
gtgtctcgaa acattagcaa caatggcatc aaattcaccg ccgcgttcga ggggttccgc   60
ggaactgcgt atcgtgctac gccaaatgag aagtacctga ctattgggta cggtcattat  120
gggccagacg taacgccagg caagaccatc accccgggac aaggcctcct gttactgaat  180
cgtgatatgg ccaaggcagt agcggcggtt gatgctgcag cgcaccattc attgacacag  240
gcacagttcg acgcagtgtg cgacctggtg tataacgcgg gtgccggtgt gattgcggct  300
actactggca caggtaaggc actgcgttct ggtgatattg caacgctgcg ggctaagctg  360
gcgctgttca tcaaccagaa cggcaaaccg ttactaggcc tgcgtcgccg taccgccggt  420
cgtctggcgc tgttcgacgg taaaccgtgg caggaggctg aggctatcgg gcgcgcggtg  480
aaaggttga                                                          489

SEQ ID NO: 4              moltype = DNA   length = 35
FEATURE                   Location/Qualifiers
misc_feature              1..35
                          note = synthetic_primer1
source                    1..35
                          mol_type = other DNA
                          organism = synthetic construct
SEQUENCE: 4
aaggatccgt gtctcgaaac attagcaaca atggc                              35

SEQ ID NO: 5              moltype = DNA   length = 25
FEATURE                   Location/Qualifiers
misc_feature              1..25
                          note = synthetic_primer2
source                    1..25
                          mol_type = other DNA
                          organism = synthetic construct
SEQUENCE: 5
aactcgagac ctttcaccgc gcgcc                                         25

SEQ ID NO: 6              moltype = AA   length = 162
FEATURE                   Location/Qualifiers
```

```
REGION                  1..162
                        note = synthetic_mtEC340
source                  1..162
                        mol_type = protein
                        organism = synthetic construct
SEQUENCE: 6
VSRNISNNGI KFTAAFEGFR GTAYRATPNE KYLTIGYGSY GPHVEPGKTI TPGQGLLLLN    60
RDMAKAVAAV DAVAHHSLTQ SQFDAVCDLV YNAGAGVIAA ATGTGKALRS GDVATLRAKL   120
ALFINQNGKP LLGLRRRTAG RLALFDGKPW QEAEAIGRAV KG                      162

SEQ ID NO: 7            moltype = AA  length = 171
FEATURE                 Location/Qualifiers
REGION                  1..171
                        note = synthetic_Met+mtEC340+His tag
source                  1..171
                        mol_type = protein
                        organism = synthetic construct
SEQUENCE: 7
MVSRNISNNG IKFTAAFEGF RGTAYRATPN EKYLTIGYGS YGPHVEPGKT ITPGQGLLLL    60
NRDMAKAVAA VDAVAHHSLT QSQFDAVCDL VYNAGAGVIA AATGTGKALR SGDVATLRAK   120
LALFINQNGK PLLGLRRRTA GRLALFDGKP WQEAEAIGRA VKGLEHHHHH H            171

SEQ ID NO: 8            moltype = AA  length = 37
FEATURE                 Location/Qualifiers
REGION                  1..37
                        note = synthetic_Cecropin A
source                  1..37
                        mol_type = protein
                        organism = synthetic construct
SEQUENCE: 8
KWKLFKKIEK VGQNIRDGII KAGPAVAVVG QATQIAK                             37

SEQ ID NO: 9            moltype = AA  length = 38
FEATURE                 Location/Qualifiers
REGION                  1..38
                        note = synthetic_Met+Cecropin A
source                  1..38
                        mol_type = protein
                        organism = synthetic construct
SEQUENCE: 9
MKWKLFKKIE KVGQNIRDGI IKAGPAVAVV GQATQIAK                            38

SEQ ID NO: 10           moltype = AA  length = 215
FEATURE                 Location/Qualifiers
REGION                  1..215
                        note = synthetic_Met+Cecropin A+GGGGS3 linker+mtEC340
source                  1..215
                        mol_type = protein
                        organism = synthetic construct
SEQUENCE: 10
MKWKLFKKIE KVGQNIRDGI IKAGPAVAVV GQATQIAKGG GGSGGGGSGG GGSVSRNISN    60
NGIKFTAAFE GFRGTAYRAT PNEKYLTIGY GSYGPHVEPG KTITPGQGLL LLNRDMAKAV   120
AAVDAVAHHS LTQSQFDAVC DLVYNAGAGV IAAATGTGKA LRSGDVATLR AKLALFINQN   180
GKPLLGLRRR TAGRLALFDG KPWQEAEAIG RAVKG                              215

SEQ ID NO: 11           moltype = AA  length = 223
FEATURE                 Location/Qualifiers
REGION                  1..223
                        note = synthetic_Met+Cecropin A+GGGGS3 linker+mtEC340+His
                            tag
source                  1..223
                        mol_type = protein
                        organism = synthetic construct
SEQUENCE: 11
MKWKLFKKIE KVGQNIRDGI IKAGPAVAVV GQATQIAKGG GGSGGGGSGG GGSVSRNISN    60
NGIKFTAAFE GFRGTAYRAT PNEKYLTIGY GSYGPHVEPG KTITPGQGLL LLNRDMAKAV   120
AAVDAVAHHS LTQSQFDAVC DLVYNAGAGV IAAATGTGKA LRSGDVATLR AKLALFINQN   180
GKPLLGLRRR TAGRLALFDG KPWQEAEAIG RAVKGLEHHH HHH                     223

SEQ ID NO: 12           moltype = DNA  length = 516
FEATURE                 Location/Qualifiers
misc_feature            1..516
                        note = synthetic_gene encoding mtEC340
source                  1..516
                        mol_type = other DNA
                        organism = synthetic construct
SEQUENCE: 12
atggttagcc gtaacatctc gaataacggc attaaattta cggctgcatt tgagggcttt    60
cgcgggaccg cctaccgtgc aaccccaaat gaaaaatatc ttaccattgg gtatggcagc   120
```

```
tatggaccgc acgttgaacc gggtaaaact attacgccgg gtcaaggttt actgttatta    180
aatcgtgata tggcaaaagc cgtggcagca gtcgacgctg tagcgcatca ttccttaacc    240
cagagtcagt tcgatgccgt gtgcgattta gtgtataatg ctggtgccgg tgtgattgcg    300
gctgcgactg gcacaggcaa agcactgcgc tctggtgatg ttgcgacctt acgtgcaaaa    360
ttggcgttgt tcattaacca aaatggcaag cctctgttag gtttacgccg tcgtacggca    420
ggacggttag ccctctttga cggtaaaccg tggcaggaag cggaggccat ggtcgcgcc    480
gtcaagggtc tcgagcacca ccaccaccac cactga                              516

SEQ ID NO: 13          moltype = DNA  length = 672
FEATURE                Location/Qualifiers
misc_feature           1..672
                       note = synthetic_gene encoding LNT113
source                 1..672
                       mol_type = other DNA
                       organism = synthetic construct
SEQUENCE: 13
atgaaatgga aactgtttaa aaaaattgaa aaagtgggcc agaacattcg cgatggcatt    60
attaaagcgg gcccggcggt ggcggtggtg ggccaggcga cccagattgc gaaaggcggt    120
ggtggttctg gtggtggcgg ctccggtggc ggcggtagtg ttagccgtaa catctcgaat    180
aacggcatta aatttacggc tgcatttgag ggctttcgcg ggaccgccta ccgtgcaacc    240
ccaaatgaaa aatatcttac cattgggtat ggcagctatg gaccgcacgt tgaacccggt    300
aaaactatta cgccggtca aggtttactg ttattaaatc gtgatatgg caaaagccggt    360
gcagcagtcg acgctgtagc gcatcattcc ttaacccaga gtcagttcga tgccgtgtgc    420
gatttagtgt ataatgctgg tgccggtgtg attgcggctg cgactggcac aggcaaagca    480
ctgcgctctg gtgatgttgc gaccttacgt gcaaaattgg cgttgttcat taaccaaaat    540
ggcaagcctc tgttaggttt acgccgtcgt acggcaggac ggttagccct ctttgacggt    600
aaaccgtggc aggaagcgga ggccattggt cgcgccgtca agggtctcga gcaccaccac    660
caccaccact ga                                                         672

SEQ ID NO: 14          moltype = AA  length = 161
FEATURE                Location/Qualifiers
source                 1..161
                       mol_type = protein
                       organism = synthetic construct
SEQUENCE: 14
MSRGISDNGL KFTAAWEDFR GTAYRATPSE KYLTIGYGSY DPHVYEGQKI TKGQGLLLLN    60
RDMAKAVAAV AAVHHSLTQ AQFDAVCDLV YNAGAGVISA TTGTGKALRA GDIATLRAKL    120
ALFINQNGKP LLGLRRRTAG RLALFDGKPW QEAEAIGRAA K                        161

SEQ ID NO: 15          moltype = AA  length = 162
FEATURE                Location/Qualifiers
source                 1..162
                       mol_type = protein
                       organism = synthetic construct
SEQUENCE: 15
MSRNISDNGL HFTAAFEGFR GTAYRATPNE KYLTIGYGSY GPHVYEGQKI TKGQGLLLLN    60
RDMAKAVAAV DAAHHSLTQ AQFDAVCDLV YNAGAGVIAA ATGTGKALRS GDVATLRAKL    120
ALFINQNGKP LLGLRRRTAG RLALFDGKPW QEAEAIGRAV KG                       162

SEQ ID NO: 16          moltype = AA  length = 162
FEATURE                Location/Qualifiers
source                 1..162
                       mol_type = protein
                       organism = synthetic construct
SEQUENCE: 16
MSRNISDNGL HFCAAFEGFR GTAYRATPNE KYLTIGYGHY GPDVTPGKTI TPGQGLLLLN    60
RDMAKAVAAV DAAHHSLTQ AQFDAVCDLV YNAGAGVIAS TTGAGKALRS GDTATLRAKL    120
ALFINQNGKP LLGLRRRTAG RLALFDGKPW QEAEAIGREV EG                       162

SEQ ID NO: 17          moltype = AA  length = 161
FEATURE                Location/Qualifiers
source                 1..161
                       mol_type = protein
                       organism = synthetic construct
SEQUENCE: 17
MRNSNNGIK FTAAFEGFRG TAYRATPNEK YLTIGYGHYG PDVTPGKTIT PGQGLLLLNR     60
DMAKAVAAVD AAHRSLTQS QFDAVCDLVY NAGAGVIAAT TGTGKALRSG DIATLRTKLA    120
LFINQNGKPL LGLRRRTAGR LALFDGKPWQ EAEAIGRAVK G                        161

SEQ ID NO: 18          moltype = AA  length = 162
FEATURE                Location/Qualifiers
source                 1..162
                       mol_type = protein
                       organism = synthetic construct
SEQUENCE: 18
MSRNISDNGL HFTAAFEGFR GTAYRATPNE KYLTIGYGHY GPDVTPGKTI TPGQGLLLLN    60
RDMAKAVAAV DAAHHSLTQ AQFDAVCDLV YNAGAGVVAA TTGTGKALRS GDVATLRAKL    120
ALFINQNGKP LLGLRRRTAG RLALFDGKPW QEAEAIGRAV KG                       162
```

```
SEQ ID NO: 19              moltype = AA    length = 162
FEATURE                    Location/Qualifiers
source                     1..162
                           mol_type = protein
                           organism = synthetic construct
SEQUENCE: 19
MSRNISDNGL HFTAAFEGFR GTAYRATPNE KYLTIGYGHY GPDVTPGKTI TPGQGLLLLN    60
RDMAKAVAAV DAAAHHSLTQ AQFDAVCDLV YNAGAGVIAA TTGTGKALRS GDVTTLRAKL   120
ALFINQNGKP ILGLRRRTAG RLALFDGKPW QEAEAIGRAV KG                      162

SEQ ID NO: 20              moltype = AA    length = 167
FEATURE                    Location/Qualifiers
source                     1..167
                           mol_type = protein
                           organism = synthetic construct
SEQUENCE: 20
MGDISVSRNI SDNGLHFTAA FEGFRGTAYR ATPNEKYLTI GYGHYGPDVT PGKTITPGQG    60
LLLLNRDMAK AVAAVDAAAH HSLTQAQFDA VCDLVYNAGA GVIAATTGTG KALRSGDIAT   120
LRAKLALFIN QNGKPLLGLR RRTAGRLALF DGKPWQEAEA IGRAVKG                 167

SEQ ID NO: 21              moltype = AA    length = 162
FEATURE                    Location/Qualifiers
source                     1..162
                           mol_type = protein
                           organism = synthetic construct
SEQUENCE: 21
MSRNISDNGL HFTAAFEGFR GTAYRATPNE KYLTIGYGHY GPDVTPGKTI TPGQGLLLLN    60
RDMAKAVAAV DAAAHHSLTQ AQFDAVCDLV YNAGAGVIAA TTGTGKALRS GDITTLRAKL   120
ALFINQNGKP LLGLRRRTAG RLALFDGKPW QEAEAIGRAV KG                      162

SEQ ID NO: 22              moltype = AA    length = 6
FEATURE                    Location/Qualifiers
source                     1..6
                           mol_type = protein
                           organism = synthetic construct
SEQUENCE: 22
GSGSGS                                                                6

SEQ ID NO: 23              moltype = AA    length = 10
FEATURE                    Location/Qualifiers
source                     1..10
                           mol_type = protein
                           organism = synthetic construct
SITE                       5..10
                           note = residues 5-10 may be absent or present
SEQUENCE: 23
GGGGGGGGGG                                                           10

SEQ ID NO: 24              moltype = AA    length = 25
FEATURE                    Location/Qualifiers
source                     1..25
                           mol_type = protein
                           organism = synthetic construct
SITE                       6..25
                           note = residues 6-10 or 11-15 or 16-20 or 21-25 may be
                            absent or present
SEQUENCE: 24
GGGGSGGGGS GGGGSGGGGS GGGGS                                          25

SEQ ID NO: 25              moltype = AA    length = 25
FEATURE                    Location/Qualifiers
source                     1..25
                           mol_type = protein
                           organism = synthetic construct
SITE                       6..25
                           note = residues 6-10 or 11-15 or 16-20 or 21-25 may be
                            absent or present
SEQUENCE: 25
EAAAKEAAAK EAAAKEAAAK EAAAK                                          25

SEQ ID NO: 26              moltype = AA    length = 25
FEATURE                    Location/Qualifiers
source                     1..25
                           mol_type = protein
                           organism = synthetic construct
SEQUENCE: 26
EAAAKEAAAK EAAAKEAAAK GGGGS                                          25

SEQ ID NO: 27              moltype = AA    length = 15
```

```
FEATURE            Location/Qualifiers
source             1..15
                   mol_type = protein
                   organism = synthetic construct
SEQUENCE: 27
GGGGSGGGGS GGGGS                                                      15

SEQ ID NO: 28      moltype = AA  length = 6
FEATURE            Location/Qualifiers
source             1..6
                   mol_type = protein
                   organism = synthetic construct
SEQUENCE: 28
HHHHHH                                                                 6
```

The invention claimed is:

1. A polypeptide, comprising the amino acid sequence of SEQ ID NO: 2, wherein
   1) the 39th residue in the amino acid sequence of SEQ ID NO: 2 is substituted with serine;
   2) the 43rd residue in the amino acid sequence of SEQ ID NO: 2 is substituted with histidine;
   3) the amino acid corresponding to the 45th residue in the amino acid sequence of SEQ ID NO: 2 is substituted with glutamic acid;
   4) the amino acid corresponding to the 73rd residue in the amino acid sequence of SEQ ID NO: 2 is substituted with valine;
   5) the amino acid corresponding to the 101st residue in the amino acid sequence of SEQ ID NO: 2 is substituted with alanine; and
   6) the amino acid corresponding to the 113rd residue in the amino acid sequence of SEQ ID NO: 2 is substituted with valine.

2. The polypeptide according to claim 1, wherein the amino acid corresponding to the 81st residue in the amino acid sequence of SEQ ID NO: 2 is further substituted with serine.

3. The polypeptide according to claim 1, comprising the amino acid sequence of SEQ ID NO: 6.

4. The polypeptide according to claim 1, further comprising Cecropin A at N-terminus or C-terminus.

5. The polypeptide according to claim 4, wherein the Cecropin A comprises the amino acid sequence of SEQ ID NO: 8 or SEQ ID NO: 9.

6. The polypeptide according to claim 4, comprising the amino acid sequence of SEQ ID NO: 10.

7. The polypeptide according to claim 1, having antibiotic activity against gram-negative bacterium.

8. The polypeptide according to claim 4, having antibiotic activity against gram-negative bacterium.

9. A polynucleotide encoding the polypeptide of claim 1 or encoding a fusion polypeptide comprising the polypeptide of claim 1 and Cecropin A.

10. A bacteriophage, comprising a polynucleotide encoding the polypeptide of claim 1 or encoding a fusion polypeptide comprising the polypeptide of claim 1 and Cecropin A.

11. The bacteriophage according to claim 10, comprising the nucleic acid sequence of SEQ ID NO: 1.

12. A method for inhibiting growth of gram negative bacterium or killing gram negative bacterium, comprising administering a pharmaceutically effective dose of at least one selected from the group consisting of:

the polypeptide of claim 1;
a fusion polypeptide comprising the polypeptide of claim 1 and Cecropin A;
a polynucleotide encoding the polypeptide of claim 1 or encoding a fusion polypeptide comprising the polypeptide of claim 1 and Cecropin A,
a recombinant vector comprising said polynucleotide encoding the polypeptide of claim 1 or encoding the fusion polypeptide comprising the polypeptide of claim 1 and Cecropin A, and
a recombinant cell comprising said polynucleotide encoding the polypeptide of claim 1 or encoding a fusion polypeptide comprising the polypeptide of claim 1 and Cecropin A, or a recombinant cell comprising said recombinant vector comprising the polynucleotide encoding the polypeptide of claim 1 or encoding the fusion polypeptide comprising the polypeptide of claim 1 and Cecropin A.

13. The method according to claim 12, further comprising administering a pharmaceutically effective dose of a polymyxin-based antibiotic.

14. The method according to claim 13, wherein the polymyxin-based antibiotic is polymyxin B, colistin or a combination thereof.

15. The method according to claim 12, wherein the gram-negative bacterium is at least one selected from the group consisting of *Pseudomonas* sp. bacterium, *Acinetobacter* sp. bacterium, *Escherichia* sp. bacterium, *Enterobacter* sp. bacterium and *Klebsiella* sp. bacterium.

16. A method for preventing or treating infection of gram negative bacterium or disease caused by gram negative bacterium, comprising administering a pharmaceutically effective dose of at least one selected from the group consisting of:

the polypeptide of claim 1;
a fusion polypeptide comprising the polypeptide of claim 1 and Cecropin A;
a polynucleotide encoding the polypeptide of claim 1 or encoding a fusion polypeptide comprising the polypeptide of claim 1 and Cecropin A,
a recombinant vector comprising said polynucleotide encoding the polypeptide of claim 1 or encoding the fusion polypeptide comprising the polypeptide of claim 1 and Cecropin A, and
a recombinant cell comprising said polynucleotide encoding the polypeptide of claim 1 or encoding a fusion polypeptide comprising the polypeptide of claim 1 and Cecropin A, or a recombinant cell comprising said recombinant vector comprising the polynucleotide encoding the polypeptide of claim 1 or encoding the fusion polypeptide comprising the polypeptide of claim 1 and Cecropin A.

17. The method according to claim 16, further comprising administering a pharmaceutically effective dose of a polymyxin-based antibiotic.

18. The method according to claim 17, wherein the polymyxin-based antibiotic is polymyxin B, colistin or a combination thereof.

19. The method according to claim 16, wherein the gram negative bacterium is *Pseudomonas* sp. bacterium, and the disease caused by *Pseudomonas* sp. bacterium is skin infection, bedsore, pneumonia, bacteremia, septicemia, endocarditis, meningitis, otitis externa, otitis media, keratitis, osteomyelitis, enteritis, peritonitis or cystic fibrosis;

the gram negative bacterium is *Acinetobacter* sp. bacterium, and the disease caused by *Acinetobacter* sp. bacterium is skin infection, pneumonia, bacteremia or septicemia; or the gram negative bacterium is *Escherichia* sp. bacterium, and the disease caused by *Escherichia* sp. bacterium is enteritis, Crohn's disease, ulcerative colitis, bacillary dysentery, urinary tract infection, skin infection, bacteremia or septicemia.

\* \* \* \* \*